(12) United States Patent
Shih et al.

(10) Patent No.: US 7,951,596 B2
(45) Date of Patent: May 31, 2011

(54) NUCLEIC ACID NANOTUBE LIQUID CRYSTALS AND USE FOR NMR STRUCTURE DETERMINATION OF MEMBRANE PROTEINS

(75) Inventors: William M. Shih, Cambridge, MA (US); Shawn M. Douglas, Boston, MA (US); James J. Chou, Cambridge, MA (US)

(73) Assignee: Dana Farber Cancer Instittute, Boston, MA (US)

( * ) Notice: Subject to any disclaimer, the term of this patent is extended or adjusted under 35 U.S.C. 154(b) by 863 days.

(21) Appl. No.: 11/732,352

(22) Filed: Apr. 3, 2007

(65) Prior Publication Data

US 2011/0089944 A1   Apr. 21, 2011

Related U.S. Application Data

(60) Provisional application No. 60/793,788, filed on Apr. 21, 2006, provisional application No. 60/904,266, filed on Feb. 28, 2007.

(51) Int. Cl.
*C12Q 1/68* (2006.01)
*G01N 24/00* (2006.01)
*C07H 21/02* (2006.01)

(52) U.S. Cl. ............................. 436/6; 436/173; 536/23.1

(58) Field of Classification Search ........................ None
See application file for complete search history.

(56) References Cited

OTHER PUBLICATIONS

Clore et al. Measurement of Residual Dipolar Couplings of Macromolecules Aligned in the Nematic Phase of a Colloidal Suspension of Rod-Shaped Viruses. Journal of the American Chemical Society (1998) 120: 10571-10572.*
Brandes et al. Magnetic Ordering of DNA Liquid Crystals. Biochemistry (1986) 25: 5890-5895.*
Rothemund et al. Design and Characterization of Programmable DNA Nanotubes. Journal of the American Chemical Society (2004) 126: 16344-16352).*
DeAngelis et al. High-Resolution NMR Spectroscopy of Membrane Proteins in Aligned Bicelles. Journal of the American Chemical Society (2004) 126: 15340-15341.*
Zhou et al. Nanostructures of Complexes Formed by Calf Thymus DNA Interacting with Cationic Surfactants. Biomacromolecules (2004) 5: 1256-1261.*
Rothemund, "Design and construction of arbitrary two-dimensional DNA shapes", Book of Abstracts: Albany 2005, vol. 22, No. 6, Jun. 2005.
Tycko, "Solid-state NMR as a probe of amyloid fibril structure", Current Opinion in Chemical Biology 2000, 4: 500-506.
Chou et al., "A simple apparatus for generating stretched polyacrylamide gels, yielding uniform alignment of proteins and detergent micelles", Journal of Biomolecular NMR, 21: 377-382, 2001.
Oxenoid et al., "The structure of phospholamban pentamer reveals a channel-like architecture in membranes", Proceedings of The National Academy of Sciences, PNAS, Aug. 2, 2005, vol. 102, No. 31, pp. 10870-10875.
Girvin et al., "Solution Structure of the Transmembrane $H^+$-Transporting subunit c of the $F_1 F_O$ ATP Synthase", Biochemistry, vol. 37, No. 25, Jun. 23, 1998, pp. 8817-8824.
Roosild et al., "NMR Structure of Mistic, a Membrane-Integrating Protein for Membrane Protein Expression", Science, vol. 307, Feb. 25, 2005, pp. 1317-1321.
Caffrey, "Membrane protein crystallization", Journal of Structural Biology, 142 (2003) 108-132.
Ohi et al., "Negative Staining and Image Classification—Powerful Tools in Modern Electron Microscopy", Biological Procedures Online, vol. 6, No. 1, Mar. 19, 2004, pp. 23-34.
Rothemund, "Folding DNA to create nanoscale shapes and patterns", Nature, vol. 440, Mar. 16, 2006, pp. 297-302.
Chou et al., "Micelle-Induced Curvature in a Water-Insoluble HIV-1 Env Peptide Revealed by NMR Dipolar Coupling Measurement in Stretched Polyacrylamide Gel", J. Am. Chem. Soc., vol. 124, No. 11, 2002, pp. 2450-2451.
Liu et al., "Approaching The Limit: Can One DNA Oligonucleotide Assemble into Large Nanostructures?", Angew. Chem. Int. Ed. 2006, 45, 1942-1945.
Mathieu et al., "Six-Helix Bundles Designed from DNA", Nano Letters, 2005, vol. 5, No. 4, pp. 661-665.
Lorigan, et al., "Solid-State NMR Spectroscopic Studies of an Integral Membrane Protein Inserted into Aligned Phospholipid Bilayer Nanotube Arrays", Journal of the American Chemical Society, Aug. 2004, vol. 126, No. 31, pp. 9504-9505.

* cited by examiner

*Primary Examiner* — M P Woodward
*Assistant Examiner* — Angela M Bertagna
(74) *Attorney, Agent, or Firm* — Edwards Angell Palmer & Dodge LLP; Elizabeth Spar; Kathleen Williams

(57) ABSTRACT

Compositions and methods for preparing nucleic acid nanotubes using DNA origami techniques are described, which provide for nanotubes of predictable and uniform length. The nucleic acid nanotubes thus formed are suitable as liquid crystal preparations enabling liquid-crystal NMR spectroscopy of proteins solubilized in detergent.

2 Claims, 42 Drawing Sheets

FIG. 4A

```
!/usr/bin/python import sys
import string sys.stdout.write('\n\n\n')

This function returns the complementary sequence

def comp(raw_sequence):
        uppercase = {'a':'A', 'A':'A', 'c':'C', 'C':'C', 'g':'G', 'G':'G',
't':'T', 'T':'T'}
        complement = {'a':'T', 'A':'T', 'c':'G', 'C':'G', 'g':'C', 'G':'C',
't':'A', 'T':'A'}
        antisense_sequence_array = []
        for letter in raw_sequence:
                if letter in uppercase:
                        antisense_sequence_array.insert(0, complement[letter])
        antisense_sequence = ''.join(antisense_sequence_array)
        return antisense_sequence

# This function returns the sequence with all unnecessary characters stripped
out

def stripped_seq(raw_sequence):
        uppercase = {'a':'A', 'A':'A', 'c':'C', 'C':'C', 'g':'G', 'G':'G',
't':'T', 'T':'T'}
        sense_sequence_array = []
        for letter in raw_sequence:
                if letter in uppercase:
                        sense_sequence_array.append(uppercase[letter])
        sense_sequence = ''.join(sense_sequence_array)
        return sense_sequence

# This program generates a six-helix bundle with bilateral pseudosymmetry
# 1. Create intermediate strands
# 2. Generate tokens
# 3. Generate oligos

```

FIG. 4B

```
# read in clonal strand sequence
input_file = file('p7308.txt', 'r')
CSS = stripped_seq(input_file.read())
CSS = CSS[-467:] + CSS[:-467]
input_file.close()

# Generate intermediate strands
num_LH_repeats = 13
num_RH_repeats = 14
start_marker = 0
fragment_ra = []
RH_overhang_length_ra = [26, 26, 40, 40, 2, 2]
LH_overhang_length_ra = [16, 16, 2, 2, 40, 40]
RC_length_ra = [20, -2, -2, 26, 26, 21]
LC_length_ra = [22,  44,  44, 16, 16, 21]

for RH_fragment_num in range(6):
      end_marker  = start_marker + RC_length_ra[RH_fragment_num]
      end_marker += num_RH_repeats*42
      end_marker += RH_overhang_length_ra[RH_fragment_num]
      fragment_ra.append(CSS[start_marker:end_marker])
      start_marker = end_marker for LH_fragment_num in range(6):
      end_marker = start_marker + LC_length_ra[5 - LH_fragment_num]
      end_marker += num_LH_repeats*42
      end_marker += LH_overhang_length_ra[5 - LH_fragment_num]
      fragment_ra.append(CSS[start_marker:end_marker])
      start_marker = end_marker I_strand_seq_ra = []
for I_strand_num in range(6):
      if I_strand_num%2 == 0:
            strand_seq = fragment_ra[11 - I_strand_num] +
fragment_ra[I_strand_num]
            upstream_fragment   =
strand_seq[LH_overhang_length_ra[I_strand_num]:]
            downstream_fragment =
strand_seq[:LH_overhang_length_ra[I_strand_num]]
      else:
            strand_seq = fragment_ra[I_strand_num] + fragment_ra[11 -
I_strand_num]
            upstream_fragment   = strand_seq[-
LH_overhang_length_ra[I_strand_num]:]
            downstream_fragment = strand_seq[:-
LH_overhang_length_ra[I_strand_num]]
      I_strand_seq_ra.append(upstream_fragment + downstream_fragment)

output_file = file('WS_strands_6hb_v5.txt', 'w')
for strand in I_strand_seq_ra:
      output_file.write(strand + '\n')
      sys.stdout.write(str(len(strand)) + '\n')
output_file.close()
```

FIG. 4C

```
# Generate token array
token_ra = []
num_strand_tokens = len(I_strand_seq_ra[0])/7
for I_strand_num in range(6):
        start_marker = 0
        sub_token_ra = []
        for token_num in range(num_strand_tokens):
                end_marker = start_marker + 7 sub_token_ra.append(comp(I_strand_seq_ra[I_strand_num][start_marker:end_ma
rker]))
                start_marker = end_marker
        token_ra.append(sub_token_ra)

# Generate oligos
ITN_ra = [4, 4, 0, 2, 2, 0]              # initial token number oligo_ra = []
num_strand_oligos = num_strand_tokens/6
for I_strand_num in range(6):
        SO = int((I_strand_num%2 - 0.5)*(-2))
        TN = ITN_ra[I_strand_num]

sub_oligo_ra = []
        for oligo_num in range(num_strand_oligos):
                oligo_seq  = token_ra[(I_strand_num + SO*2)%6][TN + 1]
                oligo_seq += token_ra[(I_strand_num + SO*2)%6][TN]
                oligo_seq += token_ra[(I_strand_num + SO)%6][num_strand_tokens - TN
- 1]
                oligo_seq += token_ra[(I_strand_num + SO)%6][num_strand_tokens - TN
- 2]
                oligo_seq += token_ra[I_strand_num][TN + 1]
                oligo_seq += token_ra[I_strand_num][TN]
                sub_oligo_ra.append(oligo_seq)
                TN += 6
        oligo_ra.append(sub_oligo_ra)

# Sort oligos by putting connecting oligos at the end of the list
sorted_oligo_ra = []
connector_oligo_ra = []
for I_strand_num in range(6):
        if I_strand_num%2 == 0:
                sorted_oligo_ra += oligo_ra[I_strand_num][:-1]
                connector_oligo_ra += oligo_ra[I_strand_num][-1:]
        else:
                connector_oligo_ra += oligo_ra[I_strand_num][:1]
                sorted_oligo_ra += oligo_ra[I_strand_num][1:]
sorted_oligo_ra += connector_oligo_ra
```

FIG. 4D

```
# Generate head-cap oligos
head_cap_oligo_ra = []
head_cap_oligo_ra.append(comp(I_strand_seq_ra[1][:16]) +
comp(I_strand_seq_ra[0][-16:]))
head_cap_oligo_ra.append(comp(I_strand_seq_ra[4][-40:]))
head_cap_oligo_ra.append(comp(I_strand_seq_ra[5][:40]))

# Generate tail-cap oligos
tail_cap_oligo_ra = []
tail_cap_oligo_ra.append(comp(I_strand_seq_ra[0][-42:-16]))
tail_cap_oligo_ra.append(comp(I_strand_seq_ra[1][16:42]))
tail_cap_oligo_ra.append(comp(I_strand_seq_ra[2][-42:-2]))
tail_cap_oligo_ra.append(comp(I_strand_seq_ra[3][2:42]))

sorted_oligo_ra += head_cap_oligo_ra + tail_cap_oligo_ra output_file = file('WS_6hb_v5_oligos.txt', 'w')
num_oligos = 0
for oligo in sorted_oligo_ra:
        output_file.write(oligo + '\n')
        num_oligos += 1
output_file.close()
```

FIG. 5A

```python
!/usr/bin/env python import sys
import string

# This program generates a six-helix bundle with bilateral pseudosymmetry
# 1. Create intermediate strands
# 2. Generate tokens
# 3. Generate oligos

# This function returns the complementary sequence
complement = string.maketrans('ACGTacgt','TGCAtgca')
def comp(s):
  return s.translate(complement)[::-1]

# This function returns the sequence with all unnecessary characters stripped out
def stripped_seq(raw_sequence):
    return ''.join([c for c in raw_sequence if c in string.letters])

# read in clonal strand sequence
input_file = file('p7308.txt', 'r')
CSS = stripped_seq(input_file.read())
CSS = CSS[-467:] + CSS[:-467]
input_file.close()

# Generate intermediate strands
num_LH_repeats = 13
num_RH_repeats = 14
start_marker = 0
fragment_ra = []
RH_overhang_length_ra = [26, 26, 40, 40, 2, 2]
LH_overhang_length_ra = [16, 16, 2, 2, 40, 40]
RC_length_ra = [20, -2, -2, 26, 26, 21]
LC_length_ra = [22,  44,  44, 16, 16, 21]

for RH_fragment_num in range(6):
        end_marker  = start_marker + RC_length_ra[RH_fragment_num]
        end_marker += num_RH_repeats*42
        end_marker += RH_overhang_length_ra[RH_fragment_num]
        fragment_ra.append(CSS[start_marker:end_marker])
        start_marker = end_marker for LH_fragment_num in range(6):
        end_marker  = start_marker + LC_length_ra[5 - LH_fragment_num]
        end_marker += num_LH_repeats*42
        end_marker += LH_overhang_length_ra[5 - LH_fragment_num]
        fragment_ra.append(CSS[start_marker:end_marker])
        start_marker = end_marker I_strand_seq_ra = []
for I_strand_num in range(6):
        if I_strand_num%2 == 0:
                strand_seq = fragment_ra[11 - I_strand_num] + fragment_ra[I_strand_num]
                upstream_fragment    = strand_seq[LH_overhang_length_ra[I_strand_num]:]
                downstream_fragment  = strand_seq[:LH_overhang_length_ra[I_strand_num]]
        else:
                strand_seq = fragment_ra[I_strand_num] + fragment_ra[11 - I_strand_num]
                upstream_fragment    = strand_seq[-LH_overhang_length_ra[I_strand_num]:]
                downstream_fragment  = strand_seq[:-LH_overhang_length_ra[I_strand_num]]
        I_strand_seq_ra.append(upstream_fragment + downstream_fragment)
```

FIG. 5B

```
# Print intermediate strands
# output_file = file('WS_strands_6hb_v5.txt', 'w')
for strand in I_strand_seq_ra:
output_file.write(strand + '\n')
sys.stdout.write(str(len(strand)) + '\n')
output_file.close()

# Generate token array
token_ra = []
num_strand_tokens = len(I_strand_seq_ra[0])/7
for I_strand_num in range(6):
        start_marker = 0
        sub_token_ra = []
        for token_num in range(num_strand_tokens):
                end_marker = start_marker + 7 sub_token_ra.append(comp(I_strand_seq_ra[I_strand_num][start_marker:end_marker]))
                start_marker = end_marker
        token_ra.append(sub_token_ra)

# Generate oligos
ITN_ra = [4, 4, 0, 2, 2, 0]                      # initial token number oligo_ra = []
num_strand_oligos = num_strand_tokens/6
for I_strand_num in range(6):
        SO = int((I_strand_num%2 - 0.5)*(-2))
        TN = ITN_ra[I_strand_num]

sub_oligo_ra = []
        for oligo_num in range(num_strand_oligos):
                oligo_seq  = token_ra[(I_strand_num + SO*2)%6][TN + 1]
                oligo_seq += token_ra[(I_strand_num + SO*2)%6][TN]
                oligo_seq += token_ra[(I_strand_num + SO)%6][num_strand_tokens - TN - 1]
                oligo_seq += token_ra[(I_strand_num + SO)%6][num_strand_tokens - TN - 2]
                oligo_seq += token_ra[I_strand_num][TN + 1]
                oligo_seq += token_ra[I_strand_num][TN]
                sub_oligo_ra.append(oligo_seq)
                TN += 6
        oligo_ra.append(sub_oligo_ra)

# Sort oligos by putting connecting oligos at the end of the list
sorted_oligo_ra = []
connector_oligo_ra = []
for I_strand_num in range(6):
        if I_strand_num%2 == 0:
                sorted_oligo_ra += oligo_ra[I_strand_num][:-1]
                connector_oligo_ra += oligo_ra[I_strand_num][-1:]
        else:
                connector_oligo_ra += oligo_ra[I_strand_num][:1]
                sorted_oligo_ra += oligo_ra[I_strand_num][1:]
sorted_oligo_ra += connector_oligo_ra

# Generate head-cap oligos
head_cap_oligo_ra = []
head_cap_oligo_ra.append(comp(I_strand_seq_ra[1][:16]) + comp(I_strand_seq_ra[0][-16:]))
head_cap_oligo_ra.append(comp(I_strand_seq_ra[4][-40:]))
head_cap_oligo_ra.append(comp(I_strand_seq_ra[5][:40]))

# Generate tail-cap oligos
tail_cap_oligo_ra = []
tail_cap_oligo_ra.append(comp(I_strand_seq_ra[0][-42:-16]))
tail_cap_oligo_ra.append(comp(I_strand_seq_ra[1][16:42]))
tail_cap_oligo_ra.append(comp(I_strand_seq_ra[2][-42:-2]))
tail_cap_oligo_ra.append(comp(I_strand_seq_ra[3][2:42]))

sorted_oligo_ra += head_cap_oligo_ra + tail_cap_oligo_ra
sorted_oligo_ra += head_cap_oligo_ra output_file = file('front_monomer_oligos.txt', 'w')
num_oligos = 0
for oligo in sorted_oligo_ra:
        output_file.write(oligo + '\n')
        num_oligos += 1
output_file.close()
```

FIG. 6A

```python
!/usr/bin/env python import sys
import string

# This program generates a six-helix bundle with bilateral pseudosymmetry
# 1. Create intermediate strands
# 2. Generate tokens
# 3. Generate oligos

# This function returns the complementary sequence
complement = string.maketrans('ACGTacgt','TGCAtgca')
def comp(s):
   return s.translate(complement)[::-1]

# This function returns the sequence with all unnecessary characters stripped out
def stripped_seq(raw_sequence):
   return ''.join([c for c in raw_sequence if c in string.letters])

# read in clonal strand sequence
input_file = file('p7308.txt', 'r')
CSS = stripped_seq(input_file.read())
CSS0 = CSS[-467:] + CSS[:-467]
CSS1 = CSS[-467 + 100:] + CSS[:-467 + 100]
CSS = ''
input_file.close()

# Generate intermediate strands
num_LH_repeats = 13
num_RH_repeats = 14
start_marker = 0
fragment_ra0 = []
fragment_ra1 = []
RH_overhang_length_ra = [26, 26, 40, 40, 2, 2]
LH_overhang_length_ra = [16, 16, 2, 2, 40, 40]
RC_length_ra = [20, -2, -2, 26, 26, 21]
LC_length_ra = [22,  44,  44, 16, 16, 21]

for RH_fragment_num in range(6):
        end_marker  = start_marker + RC_length_ra[RH_fragment_num]
        end_marker += num_RH_repeats*42
        end_marker += RH_overhang_length_ra[RH_fragment_num]
        fragment_ra0.append(CSS0[start_marker:end_marker])
        fragment_ra1.append(CSS1[start_marker:end_marker])
        start_marker = end_marker for LH_fragment_num in range(6):
        end_marker = start_marker + LC_length_ra[5 - LH_fragment_num]
        end_marker += num_LH_repeats*42
        end_marker += LH_overhang_length_ra[5 - LH_fragment_num]
        fragment_ra0.append(CSS0[start_marker:end_marker])
        fragment_ra1.append(CSS1[start_marker:end_marker])
        start_marker = end_marker strand_ra = []

for strand_num in range(6):
        if strand_num%2 == 0:
                strand0 = fragment_ra0[11 - strand_num] + fragment_ra0[strand_num]
                strand1 = fragment_ra1[11 - strand_num] + fragment_ra1[strand_num]
                strand_ra.append(strand0[-42 - RH_overhang_length_ra[strand_num]:] +
strand1[:42 + LH_overhang_length_ra[strand_num]])
        else:
                strand0 = fragment_ra0[strand_num] + fragment_ra0[11 - strand_num]
```

FIG. 6B

```
            strand1 = fragment_ra1[strand_num] + fragment_ra1[11 - strand_num]
            strand_ra.append(strand1[-42 - LH_overhang_length_ra[strand_num]:] +
strand0[:42 + RH_overhang_length_ra[strand_num]])

for strand in strand_ra:
            sys.stdout.write(strand + '\n')

token_ra = []
for strand_num in range(6):
        sub_token_ra = []
        num_tokens = 9
        for token_num in range(num_tokens):
                if strand_num%2 == 0:

sub_token_ra.append(comp(strand_ra[strand_num][token_num*14:token_num*14 + 14]))
                else:
                        sub_token_ra.insert(0,
comp(strand_ra[strand_num][token_num*14:token_num*14 + 14]))
        token_ra.append(sub_token_ra)

oligo_ra = []
num_zones = 9
for zone_num in range(num_zones):
        oligo  = token_ra[(zone_num*2 - 1)%6][zone_num]
        oligo += token_ra[(zone_num*2 + 0)%6][zone_num]
        oligo += token_ra[(zone_num*2 + 1)%6][zone_num]
        oligo_ra.append(oligo)
        oligo  = token_ra[(zone_num*2 + 4)%6][zone_num]
        oligo += token_ra[(zone_num*2 + 3)%6][zone_num]
        oligo += token_ra[(zone_num*2 + 2)%6][zone_num]
        oligo_ra.append(oligo)

output_file = file('front_rear_connector_oligos.txt', 'w')
for oligo in oligo_ra[6:-6]:
        output_file.write(oligo + '\n')
output_file.close()

input_file = file('front_monomer_oligos.txt', 'r')
lines = input_file.readlines()
input_file.close()
v5_oligo_ra = [stripped_seq(line) for line in lines]

input_file = file('rear_monomer_oligos.txt', 'r')
lines = input_file.readlines()
input_file.close()
v6_oligo_ra = [stripped_seq(line) for line in lines]

for oligo_num in range(18):
        if v5_oligo_ra.count(oligo_ra[oligo_num]) == 1:
                sys.stdout.write('Oligo ' + str(oligo_num) + ' present in v5 oligo
array.\n')
        elif v6_oligo_ra.count(oligo_ra[oligo_num]) == 1:
                sys.stdout.write('Oligo ' + str(oligo_num) + ' present in v6 oligo
array.\n')
        else:
                sys.stdout.write(oligo_ra[oligo_num] + '\n')
```

FIG. 7A

```python
!/usr/bin/env python import sys
import string

# This function returns the complementary sequence
complement = string.maketrans('ACGTacgt','TGCAtgca')
def comp(s):

return s.translate(complement)[::-1]

# This function returns the sequence with all unnecessary characters stripped out
def stripped_seq(raw_sequence):
    return ''.join([c for c in raw_sequence if c in string.letters])

# read in clonal strand sequence
input_file = file('p7308.txt', 'r')
CSS = stripped_seq(input_file.read())
CSS0 = CSS[-467:] + CSS[:-467]
CSS1 = CSS[-467 + 100:] + CSS[:-467 + 100]
CSS = ''
input_file.close()

# Generate intermediate strands
num_LH_repeats = 13
num_RH_repeats = 14
start_marker = 0
fragment_ra0 = []
fragment_ra1 = []
RH_overhang_length_ra = [26, 26, 40, 40, 2, 2]
LH_overhang_length_ra = [16, 16, 2, 2, 40, 40]
RC_length_ra = [20, -2, -2, 26, 26, 21]
LC_length_ra = [22, 44, 44, 16, 16, 21]

for RH_fragment_num in range(6):
        end_marker  = start_marker + RC_length_ra[RH_fragment_num]
        end_marker += num_RH_repeats*42
        end_marker += RH_overhang_length_ra[RH_fragment_num]
        fragment_ra0.append(CSS0[start_marker:end_marker])
        fragment_ra1.append(CSS1[start_marker:end_marker])
        start_marker = end_marker for LH_fragment_num in range(6):
        end_marker  = start_marker + LC_length_ra[5 - LH_fragment_num]
        end_marker += num_LH_repeats*42
        end_marker += LH_overhang_length_ra[5 - LH_fragment_num]
        fragment_ra0.append(CSS0[start_marker:end_marker])
        fragment_ra1.append(CSS1[start_marker:end_marker])
        start_marker = end_marker strand_ra = []

for strand_num in range(6):
        if strand_num%2 == 0:
                strand0 = fragment_ra0[11 - strand_num] + fragment_ra0[strand_num]
                strand1 = fragment_ra1[11 - strand_num] + fragment_ra1[strand_num]
                strand_ra.append(strand0[-42 - RH_overhang_length_ra[strand_num]:] + strand1[:42 + LH_overhang_length_ra[strand_num]])
        else:
                strand0 = fragment_ra0[strand_num] + fragment_ra0[11 - strand_num]
                strand1 = fragment_ra1[strand_num] + fragment_ra1[11 - strand_num]
                strand_ra.append(strand1[-42 - LH_overhang_length_ra[strand_num]:] + strand0[:42 + RH_overhang_length_ra[strand_num]])

for strand in strand_ra:
        sys.stdout.write(strand + '\n')
```

FIG. 7B

```
token_ra = []
for strand_num in range(6):
        sub_token_ra = []
        num_tokens = 9
        for token_num in range(num_tokens):
                if strand_num%2 == 0:

sub_token_ra.append(comp(strand_ra[strand_num][token_num*14:token_num*14 + 14]))
                        else:
                                sub_token_ra.insert(0,
comp(strand_ra[strand_num][token_num*14:token_num*14 + 14]))
        token_ra.append(sub_token_ra)

oligo_ra = []
num_zones = 9
for zone_num in range(num_zones):
        oligo  = token_ra[(zone_num*2 - 1)%6][zone_num]
        oligo += token_ra[(zone_num*2 + 0)%6][zone_num]
        oligo += token_ra[(zone_num*2 + 1)%6][zone_num]
        oligo_ra.append(oligo)
        oligo  = token_ra[(zone_num*2 + 4)%6][zone_num]
        oligo += token_ra[(zone_num*2 + 3)%6][zone_num]
        oligo += token_ra[(zone_num*2 + 2)%6][zone_num]
        oligo_ra.append(oligo)

output_file = file('front_rear_connector_oligos.txt', 'w')
for oligo in oligo_ra[6:-6]:
        output_file.write(oligo + '\n')
output_file.close()

input_file = file('front_monomer_oligos.txt', 'r')
lines = input_file.readlines()
input_file.close()
v5_oligo_ra = [stripped_seq(line) for line in lines]

input_file = file('rear_monomer_oligos.txt', 'r')
lines = input_file.readlines()
input_file.close()
v6_oligo_ra = [stripped_seq(line) for line in lines]

for oligo_num in range(18):
        if v5_oligo_ra.count(oligo_ra[oligo_num]) == 1:
                sys.stdout.write('Oligo ' + str(oligo_num) + ' present in v5 oligo
array.\n')
        elif v6_oligo_ra.count(oligo_ra[oligo_num]) == 1:
                sys.stdout.write('Oligo ' + str(oligo_num) + ' present in v6 oligo
array.\n')
        else:
                sys.stdout.write(oligo_ra[oligo_num] + '\n')
```

FIG. 8

AGGATCCCCGGGTACCGGCTAGTACCCGTATA

ATATTTTAGTTAATTTCATCTTCTGACCTAAATTTAATGG

TTTGAAATACCGACCGTGTGATAAATAAGGCGTTAAATAA

FIG. 9

GGATGTAAATGCTGTTCCATATAACAGTTTAAATATGCAACT

TTATATAACTATGAACGCATAACCGATACACCCTCAGCAGCG

AAAGTACGGTGTACTTTTGCGGATCGTTATTCGGTCGCTGA

FIG. 10

CGCTGGAAGTTTCAATGCAAATCCAATCCGGCTTAGGTTGGG

GGCTTGCAGGGACGACCTTTTTAACCTCGCAAGACAAAGAAC

GAGTTAAAGGCCGCGGCCAGTGCCAAGCACGACGTTGTAAAA

FIG. 11

CTTTTGATAAGAGGTCATTTTTGCGG

GGATTAGAGAGTACCTTTAATTGCTC

TGAATTTCTTAAACAGCTTGATACCGATAGTTGCGCCGAC

GAGCCTTTAATTGTATCGGTTTATCAGCTTGCTTTCGAGG

FIG. 12A

M13 DNA Scaffold Strand

AATGCTACTACTATTAGTAGAATTGATGCCACCTTTTCAGCTCGCGCCCCAAATGAAAA
TATAGCTAAACAGGTTATTGACCATTTGCGAAATGTATCTAATGGTCAAACTAAATCTA
CTCGTTCGCAGAATTGGGAATCAACTGTTATATGGAATGAAACTTCCAGACACCGTACT
TTAGTTGCATATTTAAAACATGTTGAGCTACAGCATTATATTCAGCAATTAAGCTCTAA
GCCATCCGCAAAAATGACCTCTTATCAAAAGGAGCAATTAAAGGTACTCTCTAATCCTG
ACCTGTTGGAGTTTGCTTCCGGTCTGGTTCGCTTTGAAGCTCGAATTAAAACGCGATAT
TTGAAGTCTTTCGGGCTTCCTCTTAATCTTTTTGATGCAATCCGCTTTGCTTCTGACTA
TAATAGTCAGGGTAAAGACCTGATTTTTGATTTATGGTCATTCTCGTTTTCTGAACTGT
TTAAAGCATTTGAGGGGGATTCAATGAATATTTATGACGATTCCGCAGTATTGGACGCT
ATCCAGTCTAAACATTTTACTATTACCCCCTCTGGCAAAACTTCTTTTGCAAAAGCCTC
TCGCTATTTTGGTTTTTATCGTCGTCTGGTAAACGAGGGTTATGATAGTGTTGCTCTTA
CTATGCCTCGTAATTCCTTTTGGCGTTATGTATCTGCATTAGTTGAATGTGGTATTCCT
AAATCTCAACTGATGAATCTTTCTACCTGTAATAATGTTGTTCCGTTAGTTCGTTTTAT
TAACGTAGATTTTTCTTCCCAACGTCCTGACTGGTATAATGAGCCAGTTCTTAAAATCG
CATAAGGTAATTCACAATGATTAAAGTTGAAATTAAACCATCTCAAGCCCAATTTACTA
CTCGTTCTGGTGTTTCTCGTCAGGGCAAGCCTTATTCACTGAATGAGCAGCTTTGTTAC
GTTGATTTGGGTAATGAATATCCGGTTCTTGTCAAGATTACTCTTGATGAAGGTCAGCC
AGCCTATGCGCCTGGTCTGTACACCGTTCATCTGTCCTCTTTCAAAGTTGGTCAGTTCG
GTTCCCTTATGATTGACCGTCTGCGCCTCGTTCCGGCTAAGTAACATGGAGCAGGTCGC
GGATTTCGACACAATTTATCAGGCGATGATACAAATCTCCGTTGTACTTTGTTTCGCGC
TTGGTATAATCGCTGGGGGTCAAAGATGAGTGTTTTAGTGTATTCTTTTGCCTCTTTCG
TTTTAGGTTGGTGCCTTCGTAGTGGCATTACGTATTTTACCCGTTTAATGGAAACTTCC
TCATGAAAAAGTCTTTAGTCCTCAAAGCCTCTGTAGCCGTTGCTACCCTCGTTCCGATG
CTGTCTTTCGCTGCTGAGGGTGACGATCCCGCAAAAGCGGCCTTTAACTCCCTGCAAGC
CTCAGCGACCGAATATATCGGTTATGCGTGGGCGATGGTTGTTGTCATTGTCGGCGCAA
CTATCGGTATCAAGCTGTTTAAGAAATTCACCTCGAAAGCAAGCTGATAAACCGATACA
ATTAAAGGCTCCTTTTGGAGCCTTTTTTTTGGAGATTTTCAACGTGAAAAAATTATTAT
TCGCAATTCCTTTAGTTGTTCCTTTCTATTCTCACTCCGCTGAAACTGTTGAAAGTTGT
TTAGCAAAATCCCATACAGAAAATTCATTTACTAACGTCTGGAAAGACGACAAAACTTT
AGATCGTTACGCTAACTATGAGGGCTGTCTGTGGAATGCTACAGGCGTTGTAGTTTGTA
CTGGTGACGAAACTCAGTGTTACGGTACATGGGTTCCTATTGGGCTTGCTATCCCTGAA
AATGAGGGTGGTGGCTCTGAGGGTGGCGGTTCTGAGGGTGGCGGTTCTGAGGGTGGCGG
TACTAAACCTCCTGAGTACGGTGATACACCTATTCCGGGCTATACTTATATCAACCCTC
TCGACGGCACTTATCCGCCTGGTACTGAGCAAAACCCCGCTAATCCTAATCCTTCTCTT
GAGGAGTCTCAGCCTCTTAATACTTTCATGTTTCAGAATAATAGGTTCCGAAATAGGCA
GGGGGCATTAACTGTTTATACGGGCACTGTTACTCAAGGCACTGACCCCGTTAAAACTT
ATTACCAGTACACTCCTGTATCATCAAAAGCCATGTATGACGCTTACTGGAACGGTAAA
TTCAGAGACTGCGCTTTCCATTCTGGCTTTAATGAGGATTTATTTGTTTGTGAATATCA
AGGCCAATCGTCTGACCTGCCTCAACCTCCTGTCAATGCTGGCGGCGGCTCTGGTGGTG
GTTCTGGTGGCGGCTCTGAGGGTGGTGGCTCTGAGGGTGGCGGTTCTGAGGGTGGCGGC
TCTGAGGGAGGCGGTTCCGGTGGTGGCTCTGGTTCCGGTGATTTTGATTATGAAAAGAT
GGCAAACGCTAATAAGGGGGCTATGACCGAAAATGCCGATGAAAACGCGCTACAGTCTG
ACGCTAAAGGCAAACTTGATTCTGTCGCTACTGATTACGGTGCTGCTATCGATGGTTTC
ATTGGTGACGTTTCCGGCCTTGCTAATGGTAATGGTGCTACTGGTGATTTTGCTGGCTC
TAATTCCCAAATGGCTCAAGTCGGTGACGGTGATAATTCACCTTTAATGAATAATTTCC
GTCAATATTTACCTTCCCTCCCTCAATCGGTTGAATGTCGCCCTTTTGTCTTTGGCGCT

FIG. 12B

M13 DNA Scaffold Strand

```
GGTAAACCATATGAATTTTCTATTGATTGTGACAAAATAAACTTATTCCGTGGTGTCTT
TGCGTTTCTTTTATATGTTGCCACCTTTATGTATGTATTTTCTACGTTTGCTAACATAC
TGCGTAATAAGGAGTCTTAATCATGCCAGTTCTTTTGGGTATTCCGTTATTATTGCGTT
TCCTCGGTTTCCTTCTGGTAACTTTGTTCGGCTATCTGCTTACTTTTCTTAAAAGGGC
TTCGGTAAGATAGCTATTGCTATTTCATTGTTTCTTGCTCTTATTATTGGGCTTAACTC
AATTCTTGTGGGTTATCTCTCTGATATTAGCGCTCAATTACCCTCTGACTTTGTTCAGG
GTGTTCAGTTAATTCTCCCGTCTAATGCGCTTCCCTGTTTTATGTTATTCTCTCTGTA
AAGGCTGCTATTTTCATTTTTGACGTTAAACAAAAATCGTTTCTTATTTGGATTGGGA
TAAATAATATGGCTGTTTATTTTGTAACTGGCAAATTAGGCTCTGGAAAGACGCTCGTT
AGCGTTGGTAAGATTCAGGATAAAATTGTAGCTGGGTGCAAAATAGCAACTAATCTTGA
TTTAAGGCTTCAAAACCTCCCGCAAGTCGGGAGGTTCGCTAAAACGCCTCGCGTTCTTA
GAATACCGGATAAGCCTTCTATATCTGATTTGCTTGCTATTGGGCGCGGTAATGATTCC
TACGATGAAAATAAAAACGGCTTGCTTGTTCTCGATGAGTGCGGTACTTGGTTTAATAC
CCGTTCTTGGAATGATAAGGAAAGACAGCCGATTATTGATTGGTTTCTACATGCTCGTA
AATTAGGATGGGATATTATTTTTCTTGTTCAGGACTTATCTATTGTTGATAAACAGGCG
CGTTCTGCATTAGCTGAACATGTTGTTTATTGTCGTCGTCTGGACAGAATTACTTTACC
TTTTGTCGGTACTTTATATTCTCTTATTACTGGCTCGAAAATGCCTCTGCCTAAATTAC
ATGTTGGCGTTGTTAAATATGGCGATTCTCAATTAAGCCCTACTGTTGAGCGTTGGCTT
TATACTGGTAAGAATTTGTATAACGCATATGATACTAAACAGGCTTTTTCTAGTAATTA
TGATTCCGGTGTTTATTCTTATTTAACGCCTTATTTATCACACGGTCGGTATTTCAAAC
CATTAAATTTAGGTCAGAAGATGAAATTAACTAAAATATATTTGAAAAAGTTTTCTCGC
GTTCTTTGTCTTGCGATTGGATTTGCATCAGCATTTACATATAGTTATATAACCCAACC
TAAGCCGGAGGTTAAAAAGGTAGTCTCTCAGACCTATGATTTTGATAAATTCACTATTG
ACTCTTCTCAGCGTCTTAATCTAAGCTATCGCTATGTTTTCAAGGATTCTAAGGGAAAA
TTAATTAATAGCGACGATTTACAGAAGCAAGGTTATTCACTCACATATATTGATTTATG
TACTGTTTCCATTAAAAAAGGTAATTCAAATGAAATTGTTAAATGTAATTAATTTTGTT
TTCTTGATGTTTGTTTCATCATCTTCTTTTGCTCAGGTAATTGAAATGAATAATTCGCC
TCTGCGCGATTTTGTAACTTGGTATTCAAAGCAATCAGGCGAATCCGTTATTGTTTCTC
CCGATGTAAAAGGTACTGTTACTGTATATTCATCTGACGTTAAACCTGAAAATCTACGC
AATTTCTTTATTTCTGTTTTACGTGCAAATAATTTTGATATGGTAGGTTCTAACCCTTC
CATTATTCAGAAGTATAATCCAAACAATCAGGATTATATTGATGAATTGCCATCATCTG
ATAATCAGGAATATGATGATAATTCCGCTCCTTCTGGTGGTTTCTTTGTTCCGCAAAAT
GATAATGTTACTCAAACTTTTAAAATTAATAACGTTCGGGCAAAGGATTTAATACGAGT
TGTCGAATTGTTTGTAAAGTCTAATACTTCTAAATCCTCAAATGTATTATCTATTGACG
GCTCTAATCTATTAGTTGTTAGTGCTCCTAAAGATATTTTAGATAACCTTCCTCAATTC
CTTTCAACTGTTGATTTGCCAACTGACCAGATATTGATTGAGGGTTTGATATTTGAGGT
TCAGCAAGGTGATGCTTTAGATTTTTCATTTGCTGCTGGCTCTCAGCGTGGCACTGTTG
CAGGCGGTGTTAATACTGACCGCCTCACCTCTGTTTTATCTTCTGCTGGTGGTTCGTTC
GGTATTTTTAATGGCGATGTTTAGGGCTATCAGTTCGCGCATTAAAGACTAATAGCCA
TTCAAAAATATTGTCTGTGCCACGTATTCTTACGCTTTCAGGTCAGAAGGGTTCTATCT
CTGTTGGCCAGAATGTCCCTTTTATTACTGGTCGTGTGACTGGTGAATCTGCCAATGTA
AATAATCCATTTCAGACGATTGAGCGTCAAAATGTAGGTATTTCCATGAGCGTTTTCC
TGTTGCAATGGCTGGCGGTAATATTGTTCTGGATATTACCAGCAAGGCCGATAGTTTGA
GTTCTTCTACTCAGGCAAGTGATGTTATTACTAATCAAAGAAGTATTGCTACAACGGTT
AATTTGCGTGATGGACAGACTCTTTTACTCGGTGGCCTCACTGATTATAAAAACACTTC
TCAGGATTCTGGCGTACCGTTCCTGTCTAAAATCCCTTTAATCGGCCTCCTGTTTAGCT
```

FIG. 12C

M13 DNA Scaffold Strand

CCCGCTCTGATTCTAACGAGGAAAGCACGTTATACGTGCTCGTCAAAGCAACCATAGTA
CGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATT
TAGTGCTTTACGGCACCTCGACCCCAAAAAACTTGATTTGGGTGATGGTTCACGTAGTG
GGCCATCGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTCTTTTGA
TTTATAAGGGATTTTGCCGATTTCGGAACCACCATCAAACAGGATTTTCGCCTGCTGGG
GCAAACCAGCGTGGACCGCTTGCTGCAACTCTCTCAGGGCCAGGCGGTGAAGGGCAATC
AGCTGTTGCCCGTCTCACTGGTGAAAAGAAAAACCACCCTGGCGCCCAATACGCAAACC
GCCTCTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGGCACCC
CAGGCTTTACACTTTATGCTTCCGGCTCGTATGTTGTGTGGAATTGTGAGCGGATAACA
ATTTCACACAGGAAACAGCTATGACCATGATTACGAATTCGAGCTCGGTACCCGGGGAT
CCTTATACGGGTACTAGCCATGCGTATACGGTCGCTAGCGGACTTGCCTCGCTATCAAA
GGTCTAGAGTCGACCTGCAGGCATGCAAGCTTGGCACTGGCCGTCGTTTTACAACGTCG
TGACTGGGAAAACCCTGGCGTTACCCAACTTAATCGCCTTGCAGCACATCCCCCTTTCG
CCAGCTGGCGTAATAGCGAAGAGGCCCGCACCGATCGCCCTTCCCAACAGTTGCGCAGC
CTGAATGGCGAATGGCGCTTTGCCTGGTTTCCGGCACCAGAAGCGGTGCCGGAAAGCTG
GCTGGAGTGCGATCTTCCTGAGGCCGATACTGTCGTCGTCCCCTCAAACTGGCAGATGC
ACGGTTACGATGCGCCCATCTACACCAACGTGACCTATCCCATTACGGTCAATCCGCCG
TTTGTTCCCACGGAGAATCCGACGGGTTGTTACTCGCTCACATTTAATGTTGATGAAAG
CTGGCTACAGGAAGGCCAGACGCGAATTATTTTTGATGGCGTTCCTATTGGTTAAAAAA
TGAGCTGATTTAACAAAAATTTAATGCGAATTTTAACAAAATATTAACGTTTACAATTT
AAATATTTGCTTATACAATCTTCCTGTTTTTGGGGCTTTTCTGATTATCAACCGGGGTA
CATATGATTGACATGCTAGTTTTACGATTACCGTTCATCGATTCTCTTGTTTGCTCCAG
ACTCTCAGGCAATGACCTGATAGCCTTTGTAGATCTCTCAAAAATAGCTACCCTCTCCG
GCATTAATTTATCAGCTAGAACGGTTGAATATCATATTGATGGTGATTTGACTGTCTCC
GGCCTTTCTCACCCTTTTGAATCTTTACCTACACATTACTCAGGCATTGCATTTAAAAT
ATATGAGGGTTCTAAAAATTTTTATCCTTGCGTTGAAATAAAGGCTTCTCCCGCAAAAG
TATTACAGGGTCATAATGTTTTTGGTACAACCGATTTAGCTTTATGCTCTGAGGCTTTA
TTGCTTAATTTTGCTAATTCTTTGCCTTGCCTGTATGATTTATTGGATGTT

FIG. 13A

```
AGTAATAAAAGGGACTGTTTCCTGTGTGCCTTTGATAGCGAG
AAATGGATTATTTAAACATACGAGCCGGACGGCCAGTGCCAA
AACGCTCATGGAAATAATGAGTGAGCTATGGGTAACGCCAGG
AATATCCAGAACAACCCGCTTTCCAGTCCGCCAGCTGGCGAA
ACTTGCCTGAGTAGTGAATCGGCCAACGAACTGTTGGGAAGG
ATTAACCGTTGTAGCGCCAGGGTGGTTTGCCGGAAACCAGGC
ATCAGTGAGGCCACCTGATTGCCCTTCAGGAAGATCGCACTC
AGACAGGAACGGTAGCGGTCCACGCTGGTGCATCTGCCAGTT
ATCAGAGCGGGAGCGATGGTGGTTCCGAATGGGATAGGTCAC
GGTTGCTTTGACGAGAATAGCCCGAGATCCGTCGGATTCTC
ACACCCGCCGCGCTAAGAGTCCACTATTTGTAGCCAGCTTTC
AGGGCGCTGGCAAGCGAAAAACCGTCTACCAATAGGAACGCC
GTGGCGAGAAAGGATCACCCAAATCAAGAAAATTCGCATTAA
GGGAGCCCCGATTCTAAATCGGAACCCTGTATAAGCAAATA
AAGAACTGGCTCATCGGAACAACATTATTACCCCGGTTGATA
TAATTTCAACTTTATTTAGGAATACCACATCGATGAACGGTA
GAGAAACACCAGAAAAGGAATTACGAGGGCTATCAGGTCAT
CGTAACAAAGCTGCCTCGTTTACCAGACATTAATGCCGGAGA
GAGTAATCTTGACATTTTGCAAAAGAAGCAAATCACCATCAA
CGGTGTACAGACCATTTAGACTGGATAGTGTAGGTAAAGATT
TAAGGGAACCGAACATTCATTGAATCCCTTTAGAACCCTCAT
CTCCATGTTACTTACGAGAATGACCATATTTTGCGGGAGAAG
TTGTATCATCGCCTATTATAGTCAGAAGAGCTAAATCGGTTG
CCCAGCGATTATACAGGAAGCCCGAAAGCAAAGAATTAGCAA
CGAAAGAGGCAAAATTCAAAGCGAACCAAATAGTAGTAGCAT
GGGTAAAATACGTAATTAGAGAGTACCTTTCATTTGGGGCGC
TTGAGGACTAAAGATTTTGCGGATGGCTAGATACATTTCGCA
AAAGACAGCATCGGTAGCTCAACATGTTTGATTCCCAATTCT
TTACCAGCGCCAAATTAGTTTGACCATTTAGAGCTTAATTGC
AATAAGTTTATTTTTGTTTAGCTATATTTTAATTGCTCCTTT
ATAAAGGTGGCAACGCATCAATTCTACTGACCGGAAGCAAAC
TCCTTATTACGCAGTCATACAGGCAAGGACTTCAAATATCGC
CAATAATAACGGAAGCCTCAGAGCATAACAAAGCGGATTGCA
CAGATAGCCGAACATGACCCTGTAATACAATCAAAAATCAGG
AGCAATAGCTATCTCAAGGATAAAAATTCCTCAAATGCTTTA
AATTGAGTTAAGCCATGCCTGAGTAATGCGTCCAATACTGCG
AGAGGGTAATTGAGAGGCCGGAGACAGTTTTTGCCAGAGGGG
CGCATTAGACGGGAGTTCTAGCTGATAAGACGATAAAAACCA
AATAGCAGCCTTTAGAGAGATCTACAAAGCATAGTAAGAGCA
ATCCAAATAAGAAAGAGCAAACAAGAGAATTCAACTAATGCA
AATTTGCCAGTTACATGTCAATCATATGTACAGGTAGAAAGA
TCCTGAATCTTACCAAAAACAGGAAGATTAAAATCTACGTTA
AAATCAAGATTAGTGTTAATATTTTGTTTTTTTTGGGGTCGA
GTTTTAGCGAACCTAGCTCATTTTTTAATCAGGGCGATGGCC
TCAGATATAGAAGGGCGTCTGGCCTTCCAAAGAACGTGGACT
TTTTCATCGTAGGATGAGCGAGTAACAAAGGGTTGAGTGTTG
AACCAAGTACCGCAGCGGATTGACCGTAAATCGGCAAAATCC
ATAATCGGCTGTCTGCGCATCGTAACCGTTTGCCCCAGCAGG
```

FIG. 13B

```
ATAATATCCCATCCCAGTATCGGCCTCACCGCCTGGCCCTGA
CGCGCCTGTTTATCGCACCGCTTCTGGTTTCTTTTCACCAGT
TCCAGACGACGACACATTCAGGCTGCGCCGCGGGGAGAGGCG
ATAAGAGAATATAACCTCTTCGCTATTAGGGAAACCTGTCGT
ACGCCAACATGTAACAAGGCGATTAAGTACTCACATTAATTG
CGCTCAACAGTAGGGACGTTGTAAAACGAAGCATAAAGTGTA
GTATCATATGCGTTAGGTCGACTCTAGAAAATTGTTATCCGC
GAATAAACACCGGAGACCGTATACGCATGAGCTCGAATTCGT
AAACTTTTTCAAATCCTGAAAGCGTAAGGAGATAGAACCCTT
AAATGCTGATGCAATGGCTATTAGTCTTCCAGTCACACGACC
CTTTTTAACCTCCGTCGCCATTAAAAATCGCTCAATCGTCTG
GTCAATAGTGAATTACAGAGGTGAGGCGATTGCAACAGGAAA
CTTGAAAACATAGCCCACGCTGAGAGCCTCGGCCTTGCTGGT
CTTCTGTAAATCGTCCTTGCTGAACCTCTTAGTAATAACATC
GGAAACAGTACATATCAGTTGGCAAATCTGTCCATCACGCAA
TTAATTACATTTAATCTAAAATATCTTTGAAGTGTTTTTATA
TGAGCAAAAGAAGACCGTCAATAGATAAATTAAAGGGATTTT
GTTACAAAATCGCGTTTACAAACAATTCCTTTCCTCGTTAGA
GGAGAAACAATAACACGTTATTAATTTTAGGGCGCGTACTAT
TTAACGTCAGATGAGGAACAAAGAAACCTGCGCGTAACCACC
GCACGTAAAACAGATCCTGATTATCAGAAAGGAGCGGGCGCT
TGAATAATGGAAGGTTGTTTGGATTATAGAAAGCCGGCGAAC
AGTAACAGTGCCCGGAAAGTATTAAGAGCGTTGGGAAGAAAA
AGGAGTGTACTGGTATTAGCGGGGTTTTCCTTATGCGATTTT
TTTACCGTTCCAGTGAGAGGGTTGATATGGCTTGAGATGGTT
TAAATCCTCATTAAGTACTCAGGAGGTTAGGCTTGCCCTGAC
TTGAGGCAGGTCAGCTCAGAACCGCCACATTACCCAAATCAA
ACCAGAACCACCACGATAGCAAGCCCAACTGACCTTCATCAA
CTCAGAACCGCCACTTCGTCACCAGTACAGAGGACAGATGAA
ACCAGAGCCACCACACAGCCCTCATAGTCAGACGGTCAATCA
CTTATTAGCGTTTGTTTCCAGACGTTAGAAATCCGCGACCTG
AGACTGTAGCGCGTTAAACAACTTTCAAAGTACAACGGAGAT
ACCGTAATCAGTAGAACAACTAAAGGAAACTCATCTTTGACC
AGCAAGGCCGGAAAAATCTCCAAAAAAAGCACCAACCTAAAA
GGAATTAGAGCCAGCGGTTTATCAGCTTAGTTTCCATTAAAC
CATTAAAGGTGAATTGATACCGATAGTTCGGCTACAGAGGCT
TGAATATAATGCTGAACGAGGGTAGCAAGCGCCGACAATGAC
TGATAAGAGGTCATCTTTTTCATGAGGAGCTTTCGAGGTGAA
TCCAACAGGTCAGGATGCCACTACGAAGAGGCTCCAAAAGGA
GTTTTAATTCGAGCGAATACACTAAAACTTGCGAATAATAAT
TCAAAAAGATTAAGCAAGCGCGAAACAACAGTTTCAGCGGAG
TCTTTACCCTGACTGATAAATTGTGTCGTAAATGAATTTTCT
AACAGTTCAGAAAAGCCGGAACGAGGCGTAGCGTAACGATCT
GAATCGTCATAAATTGACCAACTTTGAAAAACTACAACGCCT
GTAATAGTAAATGGGCGCATAGGCTGGTAGGAACCCATGTA
AAATAGCGAGAGGCAGAACCGGATATTCCCTCAGAGCCACCA
ACACTATCATAACCTCATTCAGTGAATATAGTACCGCCACCC
GATACATAACGCCACGAGTAGTAAATTGAAGTATAGCCCGGA
```

FIG. 13C

```
TTCATCAGTTGAGAATCATTGTGAATTAGCTCAGTACCAGGC
ATAAAACGAACTAATATACCAGTCAGGAGCTGAGACTCCTCA
GGTGCCGTAAAGCATAGAGCTTGACGGGCTTTTCGGAACCTA
CACTACGTGAACCAAGGGAAGAAAGCGATGATGGCAATTCAT
CCAACGTCAAAGGGTGTAGCGGTCACGCACCAGAAGGAGCGG
TTCCAGTTTGGAACTAATGCGCCGCTACAAAAGTTTGAGTAA
CTTATAAATCAAAAGCACGTATAACGTGGACAACTCGTATTA
CGAAAATCCTGTTTTAAACAGGAGGCCGTACATTTGAGGATT
GAGAGTTGCAGCAACGCCAGAATCCTGAAGGAGCACTAACAA
GAGACGGGCAACAGCGAGTAAAGAGTCAACAGTTGAAAGGA
GTTTGCGTATTGGGCAATACTTCTTTGAAAATATCAAACCCT
GCCAGCTGCATTAAAAGAACTCAAACTAAGCAGCAAATGAAA
CGTTGCGCTCACTGTATTACCGCCAGCCGTCAGTATTAACAC
AAGCCTGGGGTGCCTACCTACATTTTGAACCGAACGAACCAC
TCACAATTCCACACCATTGGCAGATTCATAATGCGCGAACTG
AATCATGGTCATAGCATTCTGGCCAACAAATACGTGGCACAG
GCAAGTCCGCTAGCATCATAATTACTAGCAAAGAACGCGAGA
GCTTGCATGCCTGCATACAAATTCTTACATATAACTATATGT
GTTTTCCCAGTCACGCTTAATTGAGAATGTCTGAGAGACTAC
AGGCGGATGTGCTGTTTAGGCAGAGGCAAGACGCTGAGAAGA
GCGATCGGTGCGGGAGTACCGACAAAAGTTTCCCTTAGAATC
AAAGCGCCATTCGCATAAACAACATGTTAGTGAATAACCTTG
CAGCCAGCTTTCCGAACAATAGATAAGTTTACCTTTTTTAAT
TGAGGGGACGACGATAATTTACGAGCATTCAAGAAAACAAAA
GTTGGTGTAGATGGTTCCTTATCATTCCTCATTTCAATTACC
CGTGGGAACAAACGCTCATCGAGAACAAGCTTTGAATACCAA
ATCAACATTAAATGATCATTACCGCGCCTACCTTTTACATCG
ATCAAAAATAATTCCTTATCCGGTATTCGTAGATTTTCAGGT
ATTTTTGTTAAATCCCCGACTTGCGGGATATCAAAATTATTT
TTTAAATTGTAAACTGCTATTTTGCACCGCCCCCTGCCTATC
ATCAGAAAAGCCCCAACGCTAACGAGCGGGGTCAGTGCCTTG
ATCGTAAAACTAGCAAAATAAACAGCCAGCTTTTGATGATAC
TGCCTGAGAGTCTGCGATTTTTTGTTTAGCGCAGTCTCTGAA
GGGTAGCTATTTTTCAGAGAGAATAACATATTCACAAACAAA
TATGATATTCAACCGAATTAACTGAACAGCATTGACAGGAGG
CAAAAGGGTGAGAACGCTAATATCAGAGCCCTCAGAGCCGCC
ATATTTTAAATGCACAATAATAAGAGCATCAGAGCCGCCACC
CCTTTATTTCAACGTACCGAAGCCCTTTTCAAAATCACCGGA
TACCAAAAACATTAAAGTTACCAGAAGGTCGGTCATAGCCCC
AATTAAGCAATAAATACCCAAAAGAACTTTGCCTTTAGCGTC
TAACATCCAATAAATATGTTAGCAAACGCCATCGATAGCAGC
GAGCTGAAAAGGTGATATAAAAGAAACGGCACCATTACCATT
AATGGTCAATAACCGTCACAATCAATAGACTTGAGCCATTTG
GCGAACGAGTAGATGACAAAAGGGCGACTGACGGAAATTATT
AACAACCATCGCCCGGGAAGGTAAATATATTCAACCGATTGA
TTTCTTAAACAGCTTATCACCGTCACCGAAAATTCATATGGT
GCCTTTAATTGTATCAAAATCACCAGTACAAAGACACCACGG
TTTTTCACGTTGAACGTCACCAATGAAATAGAAAATACATAC
```

FIG. 13D

```
TGAGAATAGAAAGGCGACAGAATCAAGTGGCATGATTAAGAC
GTATGGGATTTTGCTTTCATCGGCATTTAAACCGAGGAAACG
AAAGTTTTGTCGTCCCATCTTTTCATAATTAAGAAAAGTAAG
GTAGCATTCCACAGCGGAACCGCCTCCCAGAAACAATGAAAT
CCGTAACACTGAGTCCTCAGAGCCACCAAGATAACCCACAAG
CCCTCATTTTCAGGCAGAGCCGCCGCCACCCTGAACAAAGTC
TCAGAACCGCCACCACGATTGGCCTTGATAAAACAGGGAAG
ATAGGTGTATCACCAGCCAGAATGGAAACGTCAAAATGAA
GGATAAGTGCCGTCAAGCGTCATACATGTATTATTTATCCCA
AGAGAAGGATTAGGAATAAGTTTTAACGTCTTTCCAGAGCCT
TTATTCTGAAACATTATAAACAGTTAATCAGCTACAATTTTA
CAATATAATCCTGAGTTAGAACCTACCAGGTTTTGAAGCCTT
AATTATCATCATATAATAAGAAATTGCTAAGAACGCGAGGC
CATTATCATTTGCATATACAGTAACAGCAATAGCAAGCAAA
AATCCTTTGCCCGAGGATTCGCCTGATTGCAAGCCGTTTTA
TAGAAGTATTAGACCAGAGGCGAATTATAAGAACGGGTATTA
CTAATAGATTAGAGTGATGAAACAAACAGTAGAAACCAATCA
ATTGAGGAAGGTTACAATTTCATTTGAACCTGAACAAGAAAA
CAATCAATATCTGGAATCAATATATGTGCAGCTAATGCAGAA
AATCTAAAGCATCACGCTATTAATTAATGTAAAGTAATTCTG
CGCCTGCAACAGTGGATAGCTTAGATTATTTTCGAGCCAGTA
CAGCAGAAGATAAATATCAAAATCATAGCGCCATATTTAACA
ATAGCCCTAAAACAGCTTAGGTTGGGTTCAGTATAAAGCCAA
ACAATATTTTGAAATCCAATCGCAAGAAAAAGCCTGTTTA
CTGTTAAAGGCCGCGATCCCCGGGTACCGGCTAGTACCCGTA
GGTTTGAAATACCGTTCCATATAACAGTTTAAATATGCAACT
TAAATTTAATGGGAACGCATAACCGATACACCCTCAGCAGCG
AAAGTACGGTGTAGTTTTGCGGGATCGTTATTCGGTCGCTGA
TACTGGAAGTTTCAACCGTGTGATAAATTTCATCTTCTGACC
GGCTTGCAGGGAGAATATTTAGTTAATAAGGCGTTAAATAA
AGGATCCCCGGGTACCGGCTAGTACCCGTATA
ATATTTAGTTAATTTCATCTTCTGACCTAAATTTAATGG
TTTGAAATACCGACCGTGTGATAAATAAGGCGTTAAATAA
CTGGAAGTTTCATTCCATATAACAGT
TTAAATATGCAACTAAAGTACGGTGT
GTTAAAGGCCGCTTTTGCGGGATCGTCACCCTCAGCAGCG
ACGCATAACCGATATATTCGGTCGCTGAGGCTTGCAGGGA
```

FIG. 14

TATACGGGTACTAGCCATGCGTATACGGTCGCTAGCGGACTTGCCTCGCTATCAAAGGT

FIG. 15

TCGAGCTCGGTACCCGGGGATCCTTATACG

CGCATGGCTAGTACCCGTATAAGGATCCCC

GGTACTAGCCATGCGTATACGGTCGCTAGC

TAGCGAGGCAAGTCCGCTAGCGACCGTATA

GGACTTGCCTCGCTATCAAAGGTCTAGAGT

CATGCCTGCAGGTCGACTCTAGACCTTTGA

FIG. 16A

```
AATGCTACTACTATTAGTAGAATTGATGCCACCTTTTCAGCTCGCGCCCCAAATGAAAA
TATAGCTAAACAGGTTATTGACCATTTGCGAAATGTATCTAATGGTCAAACTAAATCTA
CTCGTTCGCAGAATTGGGAATCAACTGTTATATGGAATGAAACTTCCAGACACCGTACT
TTAGTTGCATATTTAAAACATGTTGAGCTACAGCATTATATTCAGCAATTAAGCTCTAA
GCCATCCGCAAAAATGACCTCTTATCAAAAGGAGCAATTAAAGGTACTCTCTAATCCTG
ACCTGTTGGAGTTTGCTTCCGGTCTGGTTCGCTTTGAAGCTCGAATTAAAACGCGATAT
TTGAAGTCTTTCGGGCTTCCTCTTAATCTTTTTGATGCAATCCGCTTTGCTTCTGACTA
TAATAGTCAGGGTAAAGACCTGATTTTTGATTTATGGTCATTCTCGTTTTCTGAACTGT
TTAAAGCATTTGAGGGGGATTCAATGAATATTTATGACGATTCCGCAGTATTGGACGCT
ATCCAGTCTAAACATTTTACTATTACCCCTCTGGCAAAACTTCTTTTGCAAAAGCCTC
TCGCTATTTTGGTTTTTATCGTCGTCTGGTAAACGAGGGTTATGATAGTGTTGCTCTTA
CTATGCCTCGTAATTCCTTTTGGCGTTATGTATCTGCATTAGTTGAATGTGGTATTCCT
AAATCTCAACTGATGAATCTTTCTACCTGTAATAATGTTGTTCCGTTAGTTCGTTTTAT
TAACGTAGATTTTTCTTCCCAACGTCCTGACTGGTATAATGAGCCAGTTCTTAAAATCG
CATAAGGTAATTCACAATGATTAAAGTTGAAATTAAACCATCTCAAGCCCAATTTACTA
CTCGTTCTGGTGTTTCTCGTCAGGGCAAGCCTTATTCACTGAATGAGCAGCTTTGTTAC
GTTGATTTGGGTAATGAATATCCGGTTCTTGTCAAGATTACTCTTGATGAAGGTCAGCC
AGCCTATGCGCCTGGTCTGTACACCGTTCATCTGTCCTCTTTCAAAGTTGGTCAGTTCG
GTTCCCTTATGATTGACCGTCTGCGCCTCGTTCCGGCTAAGTAACATGGAGCAGGTCGC
GGATTTCGACACAATTTATCAGGCGATGATACAAATCTCCGTTGTACTTTGTTTCGCGC
TTGGTATAATCGCTGGGGGTCAAAGATGAGTGTTTTAGTGTATTCTTTTGCCTCTTTCG
TTTTAGGTTGGTGCCTTCGTAGTGGCATTACGTATTTTACCCGTTTAATGGAAACTTCC
TCATGAAAAAGTCTTTAGTCCTCAAAGCCTCTGTAGCCGTTGCTACCCTCGTTCCGATG
CTGTCTTTCGCTGCTGAGGGTGACGATCCCGCAAAAGCGGCCTTTAACTCCCTGCAAGC
CTCAGCGACCGAATATATCGGTTATGCGTGGGCGATGGTTGTTGTCATTGTCGGCGCAA
CTATCGGTATCAAGCTGTTTAAGAAATTCACCTCGAAAGCAAGCTGATAAACCGATACA
ATTAAAGGCTCCTTTTGGAGCCTTTTTTTGGAGATTTTCAACGTGAAAAAATTATTAT
TCGCAATTCCTTTAGTTGTTCCTTTCTATTCTCACTCCGCTGAAACTGTTGAAAGTTGT
TTAGCAAAATCCCATACAGAAAATTCATTTACTAACGTCTGGAAAGACGACAAAACTTT
AGATCGTTACGCTAACTATGAGGGCTGTCTGTGGAATGCTACAGGCGTTGTAGTTTGTA
CTGGTGACGAAACTCAGTGTTACGGTACATGGGTTCCTATTGGGCTTGCTATCCCTGAA
AATGAGGGTGGTGGCTCTGAGGGTGGCGGTTCTGAGGGTGGCGGTTCTGAGGGTGGCGG
TACTAAACCTCCTGAGTACGGTGATACACCTATTCCGGGCTATACTTATATCAACCCTC
TCGACGGCACTTATCCGCCTGGTACTGAGCAAAACCCCGCTAATCCTAATCCTTCTCTT
GAGGAGTCTCAGCCTCTTAATACTTTCATGTTTCAGAATAATAGGTTCCGAAATAGGCA
GGGGGCATTAACTGTTTATACGGGCACTGTTACTCAAGGCACTGACCCCGTTAAAACTT
ATTACCAGTACACTCCTGTATCATCAAAAGCCATGTATGACGCTTACTGGAACGGTAAA
TTCAGAGACTGCGCTTTCCATTCTGGCTTTAATGAGGATTTATTTGTTTGTGAATATCA
AGGCCAATCGTCTGACCTGCCTCAACCTCCTGTCAATGCTGGCGGCGGCTCTGGTGGTG
GTTCTGGTGGCGGCTCTGAGGGTGGTGGCTCTGAGGGTGGCGGTTCTGAGGGTGGCGGC
TCTGAGGGAGGCGGTTCCGGTGGTGGCTCTGGTTCCGGTGATTTTGATTATGAAAAGAT
GGCAAACGCTAATAAGGGGGCTATGACCGAAAATGCCGATGAAAACGCGCTACAGTCTG
```

FIG. 16B

```
ACGCTAAAGGCAAACTTGATTCTGTCGCTACTGATTACGGTGCTGCTATCGATGGTTTC
ATTGGTGACGTTTCCGGCCTTGCTAATGGTAATGGTGCTACTGGTGATTTTGCTGGCTC
TAATTCCCAAATGGCTCAAGTCGGTGACGGTGATAATTCACCTTTAATGAATAATTTCC
GTCAATATTTACCTTCCCTCCCTCAATCGGTTGAATGTCGCCCTTTTGTCTTTGGCGCT
GGTAAACCATATGAATTTTCTATTGATTGTGACAAAATAAACTTATTCCGTGGTGTCTT
TGCGTTTCTTTTATATGTTGCCACCTTTATGTATGTATTTTCTACGTTTGCTAACATAC
TGCGTAATAAGGAGTCTTAATCATGCCAGTTCTTTTGGGTATTCCGTTATTATTGCGTT
TCCTCGGTTTCCTTCTGGTAACTTTGTTCGGCTATCTGCTTACTTTTCTTAAAAAGGGC
TTCGGTAAGATAGCTATTGCTATTTCATTGTTTCTTGCTCTTATTATTGGGCTTAACTC
AATTCTTGTGGGTTATCTCTCTGATATTAGCGCTCAATTACCCTCTGACTTTGTTCAGG
GTGTTCAGTTAATTCTCCCGTCTAATGCGCTTCCCTGTTTTTATGTTATTCTCTCTGTA
AAGGCTGCTATTTTCATTTTTGACGTTAAACAAAAAATCGTTTCTTATTTGGATTGGGA
TAAATAATATGGCTGTTTATTTTGTAACTGGCAAATTAGGCTCTGGAAAGACGCTCGTT
AGCGTTGGTAAGATTCAGGATAAAATTGTAGCTGGGTGCAAAATAGCAACTAATCTTGA
TTTAAGGCTTCAAAACCTCCCGCAAGTCGGGAGGTTCGCTAAAACGCCTCGCGTTCTTA
GAATACCGGATAAGCCTTCTATATCTGATTTGCTTGCTATTGGGCGCGGTAATGATTCC
TACGATGAAAATAAAAACGGCTTGCTTGTTCTCGATGAGTGCGGTACTTGGTTTAATAC
CCGTTCTTGGAATGATAAGGAAAGACAGCCGATTATTGATTGGTTTCTACATGCTCGTA
AATTAGGATGGGATATTATTTTTCTTGTTCAGGACTTATCTATTGTTGATAAACAGGCG
CGTTCTGCATTAGCTGAACATGTTGTTTATTGTCGTCGTCTGGACAGAATTACTTTACC
TTTTGTCGGTACTTTATATTCTCTTATTACTGGCTCGAAAATGCCTCTGCCTAAATTAC
ATGTTGGCGTTGTTAAATATGGCGATTCTCAATTAAGCCCTACTGTTGAGCGTTGGCTT
TATACTGGTAAGAATTTGTATAACGCATATGATACTAAACAGGCTTTTTCTAGTAATTA
TGATTCCGGTGTTTATTCTTATTTAACGCCTTATTTATCACACGGTCGGTATTTCAAAC
CATTAAATTTAGGTCAGAAGATGAAATTAACTAAAATATATTTGAAAAAGTTTTCTCGC
GTTCTTTGTCTTGCGATTGGATTTGCATCAGCATTTACATATAGTTATATAACCCAACC
TAAGCCGGAGGTTAAAAAGGTAGTCTCTCAGACCTATGATTTTGATAAATTCACTATTG
ACTCTTCTCAGCGTCTTAATCTAAGCTATCGCTATGTTTTCAAGGATTCTAAGGGAAAA
TTAATTAATAGCGACGATTTACAGAAGCAAGGTTATTCACTCACATATATTGATTTATG
TACTGTTTCCATTAAAAAAGGTAATTCAAATGAAATTGTTAAATGTAATTAATTTTGTT
TTCTTGATGTTTGTTTCATCATCTTCTTTTGCTCAGGTAATTGAAATGAATAATTCGCC
TCTGCGCGATTTTGTAACTTGGTATTCAAAGCAATCAGGCGAATCCGTTATTGTTTCTC
CCGATGTAAAAGGTACTGTTACTGTATATTCATCTGACGTTAAACCTGAAAATCTACGC
AATTTCTTTATTTCTGTTTTACGTGCAAATAATTTTGATATGGTAGGTTCTAACCCTTC
CATTATTCAGAAGTATAATCCAAACAATCAGGATTATATTGATGAATTGCCATCATCTG
ATAATCAGGAATATGATGATAATTCCGCTCCTTCTGGTGGTTTCTTTGTTCCGCAAAAT
GATAATGTTACTCAAACTTTTAAAATTAATAACGTTCGGGCAAAGGATTTAATACGAGT
TGTCGAATTGTTTGTAAAGTCTAATACTTCTAAATCCTCAAATGTATTATCTATTGACG
GCTCTAATCTATTAGTTGTTAGTGCTCCTAAAGATATTTTAGATAACCTTCCTCAATTC
CTTTCAACTGTTGATTTGCCAACTGACCAGATATTGATTGAGGGTTTGATATTTGAGGT
TCAGCAAGGTGATGCTTTAGATTTTTCATTTGCTGCTGGCTCTCAGCGTGGCACTGTTG
CAGGCGGTGTTAATACTGACCGCCTCACCTCTGTTTTATCTTCTGCTGGTGGTTCGTTC
```

FIG. 16C

```
GGTATTTTTAATGGCGATGTTTTAGGGCTATCAGTTCGCGCATTAAAGACTAATAGCCA
TTCAAAAATATTGTCTGTGCCACGTATTCTTACGCTTTCAGGTCAGAAGGGTTCTATCT
CTGTTGGCCAGAATGTCCCTTTTATTACTGGTCGTGTGACTGGTGAATCTGCCAATGTA
AATAATCCATTTCAGACGATTGAGCGTCAAAATGTAGGTATTTCCATGAGCGTTTTTCC
TGTTGCAATGGCTGGCGGTAATATTGTTCTGGATATTACCAGCAAGGCCGATAGTTTGA
GTTCTTCTACTCAGGCAAGTGATGTTATTACTAATCAAAGAAGTATTGCTACAACGGTT
AATTTGCGTGATGGACAGACTCTTTTACTCGGTGGCCTCACTGATTATAAAAACACTTC
TCAGGATTCTGGCGTACCGTTCCTGTCTAAAATCCCTTTAATCGGCCTCCTGTTTAGCT
CCCGCTCTGATTCTAACGAGGAAAGCACGTTATACGTGCTCGTCAAAGCAACCATAGTA
CGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATT
TAGTGCTTTACGGCACCTCGACCCCAAAAAACTTGATTTGGGTGATGGTTCACGTAGTG
GGCCATCGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTCTTTTGA
TTTATAAGGGATTTTGCCGATTTCGGAACCACCATCAAACAGGATTTTCGCCTGCTGGG
GCAAACCAGCGTGGACCGCTTGCTGCAACTCTCTCAGGGCCAGGCGGTGAAGGGCAATC
AGCTGTTGCCCGTCTCACTGGTGAAAGAAAAACCACCCTGGCGCCCAATACGCAAACC
GCCTCTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGGCACCC
CAGGCTTTACACTTTATGCTTCCGGCTCGTATGTTGTGTGGAATTGTGAGCGGATAACA
ATTTCACACAGGAAACAGCTATGACCATGATTACGAATTCGAGCTCGGTACCCGGGGAT
CCTTATACGGGTACTAGCCATGCGTATACGGTCGCTAGCGGACTTGCCTCGCTATCAAA
GGTCTAGAGTCGACCTGCAGGCATGCAAGCTTGGCACTGGCCGTCGTTTTACAACGTCG
TGACTGGGAAAACCCTGGCGTTACCCAACTTAATCGCCTTGCAGCACATCCCCCTTTCG
CCAGCTGGCGTAATAGCGAAGAGGCCCGCACCGATCGCCCTTCCCAACAGTTGCGCAGC
CTGAATGGCGAATGGCGCTTTGCCTGGTTTCCGGCACCAGAAGCGGTGCCGGAAAGCTG
GCTGGAGTGCGATCTTCCTGAGGCCGATACTGTCGTCGTCCCCTCAAACTGGCAGATGC
ACGGTTACGATGCGCCCATCTACACCAACGTGACCTATCCCATTACGGTCAATCCGCCG
TTTGTTCCCACGGAGAATCCGACGGGTTGTTACTCGCTCACATTTAATGTTGATGAAAG
CTGGCTACAGGAAGGCCAGACGCGAATTATTTTTGATGGCGTTCCTATTGGTTAAAAAA
TGAGCTGATTTAACAAAAATTTAATGCGAATTTTAACAAAATATTAACGTTTACAATTT
AAATATTTGCTTATACAATCTTCCTGTTTTTGGGGCTTTTCTGATTATCAACCGGGGTA
CATATGATTGACATGCTAGTTTTACGATTACCGTTCATCGATTCTCTTGTTTGCTCCAG
ACTCTCAGGCAATGACCTGATAGCCTTTGTAGATCTCTCAAAAATAGCTACCCTCTCCG
GCATTAATTTATCAGCTAGAACGGTTGAATATCATATTGATGGTGATTTGACTGTCTCC
GGCCTTTCTCACCCTTTTGAATCTTTACCTACACATTACTCAGGCATTGCATTTAAAAT
ATATGAGGGTTCTAAAAATTTTTATCCTTGCGTTGAAATAAAGGCTTCTCCCGCAAAAG
TATTACAGGGTCATAATGTTTTTGGTACAACCGATTTAGCTTTATGCTCTGAGGCTTTA
TTGCTTAATTTTGCTAATTCTTTGCCTTGCCTGTATGATTTATTGGATGTT
```

FIG.17A

```
AGTAATAAAAGGGACTGTTTCCTGTGTGCCTTTGATAGCGAG
AAATGGATTATTTAAACATACGAGCCGGACGGCCAGTGCCAA
AACGCTCATGGAAATAATGAGTGAGCTATGGGTAACGCCAGG
AATATCCAGAACAACCCGCTTTCCAGTCCGCCAGCTGGCGAA
ACTTGCCTGAGTAGTGAATCGGCCAACGAACTGTTGGGAAGG
ATTAACCGTTGTAGCGCCAGGGTGGTTTGCCGGAAACCAGGC
ATCAGTGAGGCCACCTGATTGCCCTTCAGGAAGATCGCACTC
AGACAGGAACGGTAGCGGTCCACGCTGGTGCATCTGCCAGTT
ATCAGAGCGGGAGCGATGGTGGTTCCGAATGGGATAGGTCAC
GGTTGCTTTGACGAGAATAGCCCGAGATCCCGTCGGATTCTC
ACACCCGCCGCGCTAAGAGTCCACTATTTGTAGCCAGCTTTC
AGGGCGCTGGCAAGCGAAAAACCGTCTACCAATAGGAACGCC
GTGGCGAGAAAGGATCACCCAAATCAAGAAAATTCGCATTAA
GGGAGCCCCCGATTCTAAATCGGAACCCTGTATAAGCAAATA
AAGAACTGGCTCATCGGAACAACATTATTACCCCGGTTGATA
TAATTTCAACTTTATTTAGGAATACCACATCGATGAACGGTA
GAGAAACACCAGAAAAAGGAATTACGAGGGCTATCAGGTCAT
CGTAACAAAGCTGCCTCGTTTACCAGACATTAATGCCGGAGA
GAGTAATCTTGACATTTTGCAAAAGAAGCAAATCACCATCAA
CGGTGTACAGACCATTTAGACTGGATAGTGTAGGTAAAGATT
TAAGGGAACCGAACATTCATTGAATCCCTTTAGAACCCTCAT
CTCCATGTTACTTACGAGAATGACCATATTTTGCGGGAGAAG
TTGTATCATCGCCTATTATAGTCAGAAGAGCTAAATCGGTTG
CCCAGCGATTATACAGGAAGCCCGAAAGCAAAGAATTAGCAA
CGAAAGAGGCAAAATTCAAAGCGAACCAAATAGTAGTAGCAT
GGGTAAAATACGTAATTAGAGAGTACCTTTCATTTGGGGCGC
TTGAGGACTAAAGATTTTGCGGATGGCTAGATACATTTCGCA
AAAGACAGCATCGGTAGCTCAACATGTTTGATTCCCAATTCT
TTACCAGCGCCAAATTAGTTTGACCATTTAGAGCTTAATTGC
AATAAGTTTATTTTTGTTTAGCTATATTTAATTGCTCCTTT
ATAAAGGTGGCAACGCATCAATTCTACTGACCGGAAGCAAAC
TCCTTATTACGCAGTCATACAGGCAAGGACTTCAAATATCGC
CAATAATAACGGAAGCCTCAGAGCATAACAAAGCGGATTGCA
CAGATAGCCGAACATGACCCTGTAATACAATCAAAAATCAGG
AGCAATAGCTATCTCAAGGATAAAAATTCCTCAAATGCTTTA
AATTGAGTTAAGCCATGCCTGAGTAATGCGTCCAATACTGCG
AGAGGGTAATTGAGAGGCCGGAGACAGTTTTTGCCAGAGGGG
CGCATTAGACGGGAGTTCTAGCTGATAAGACGATAAAAACCA
AATAGCAGCCTTTAGAGAGATCTACAAAGCATAGTAAGAGCA
ATCCAAATAAGAAAGAGCAAACAAGAGAATTCAACTAATGCA
AATTTGCCAGTTACATGTCAATCATATGTACAGGTAGAAAGA
TCCTGAATCTTACCAAAAACAGGAAGATTAAAATCTACGTTA
AAATCAAGATTAGTGTTAATATTTTGTTTTTTTGGGGTCGA
GTTTTAGCGAACCTAGCTCATTTTTTAATCAGGGCGATGGCC
```

FIG. 17B

```
TCAGATATAGAAGGGCGTCTGGCCTTCCAAAGAACGTGGACT
TTTTCATCGTAGGATGAGCGAGTAACAAAGGGTTGAGTGTTG
AACCAAGTACCGCAGCGGATTGACCGTAAATCGGCAAAATCC
ATAATCGGCTGTCTGCGCATCGTAACCGTTTGCCCCAGCAGG
ATAATATCCATCCAGTATCGGCCTCACCGCCTGGCCCTGA
CGCGCCTGTTTATCGCACCGCTTCTGGTTTCTTTTCACCAGT
TCCAGACGACGACACATTCAGGCTGCGCCGCGGGGAGAGGCG
ATAAGAGAATATAACCTCTTCGCTATTAGGGAAACCTGTCGT
ACGCCAACATGTAACAAGGCGATTAAGTACTCACATTAATTG
CGCTCAACAGTAGGGACGTTGTAAAACGAAGCATAAAGTGTA
GTATCATATGCGTTAGGTCGACTCTAGAAAATTGTTATCCGC
GAATAAACACCGGAGACCGTATACGCATGAGCTCGAATTCGT
AAACTTTTTCAAATCCTGAAAGCGTAAGGAGATAGAACCCTT
AAATGCTGATGCAATGGCTATTAGTCTTCCAGTCACACGACC
CTTTTTAACCTCCGTCGCCATTAAAAATCGCTCAATCGTCTG
GTCAATAGTGAATTACAGAGGTGAGGCGATTGCAACAGGAAA
CTTGAAAACATAGCCCACGCTGAGAGCCTCGGCCTTGCTGGT
CTTCTGTAAATCGTCCTTGCTGAACCTCTTAGTAATAACATC
GGAAACAGTACATATCAGTTGGCAAATCTGTCCATCACGCAA
TTAATTACATTTAATCTAAAATATCTTTGAAGTGTTTTATA
TGAGCAAAAGAAGACCGTCAATAGATAAATTAAAGGGATTTT
GTTACAAAATCGCGTTTACAAACAATTCCTTTCCTCGTTAGA
GGAGAAACAATAACACGTTATTAATTTTAGGGCGCGTACTAT
TTAACGTCAGATGAGGAACAAAGAAACCTGCGCGTAACCACC
GCACGTAAAACAGATCCTGATTATCAGAAAGGAGCGGGCGCT
TGAATAATGGAAGGTTGTTTGGATTATAGAAAGCCGGCGAAC
AGTAACAGTGCCCGGAAAGTATTAAGAGCGTTGGGAAGAAAA
AGGAGTGTACTGGTATTAGCGGGGTTTTCCTTATGCGATTTT
TTTACCGTTCCAGTGAGAGGGTTGATATGGCTTGAGATGGTT
TAAATCCTCATTAAGTACTCAGGAGGTTAGGCTTGCCCTGAC
TTGAGGCAGGTCAGCTCAGAACCGCCACATTACCCAAATCAA
ACCAGAACCACCACGATAGCAAGCCCAACTGACCTTCATCAA
CTCAGAACCGCCACTTCGTCACCAGTACAGAGGACAGATGAA
ACCAGAGCCACCACACAGCCCTCATAGTCAGACGGTCAATCA
CTTATTAGCGTTTGTTTCCAGACGTTAGAAATCCGCGACCTG
AGACTGTAGCGCGTTAAACAACTTTCAAAGTACAACGGAGAT
ACCGTAATCAGTAGAACAACTAAAGGAAACTCATCTTTGACC
AGCAAGGCCGGAAAAATCTCCAAAAAAGCACCAACCTAAAA
GGAATTAGAGCCAGCGGTTTATCAGCTTAGTTTCCATTAAAC
CATTAAAGGTGAATTGATACCGATAGTTCGGCTACAGAGGCT
TGAATATAATGCTGAACGAGGGTAGCAAGCGCCGACAATGAC
TGATAAGAGGTCATCTTTTTCATGAGGAGCTTTCGAGGTGAA
TCCAACAGGTCAGGATGCCACTACGAAGAGGCTCCAAAAGGA
GTTTTAATTCGAGCGAATACACTAAAACTTGCGAATAATAAT
```

FIG. 17C

```
TCAAAAAGATTAAGCAAGCGCGAAACAACAGTTTCAGCGGAG
TCTTTACCCTGACTGATAAATTGTGTCGTAAATGAATTTTCT
AACAGTTCAGAAAAGCCGGAACGAGGCGTAGCGTAACGATCT
GAATCGTCATAAATTGACCAACTTTGAAAAACTACAACGCCT
GTAATAGTAAATGGGCGCATAGGCTGGTAGGAACCCATGTA
AAATAGCGAGAGGCAGAACCGGATATTCCCTCAGAGCCACCA
ACACTATCATAACCTCATTCAGTGAATATAGTACCGCCACCC
GATACATAACGCCACGAGTAGTAAATTGAAGTATAGCCCGGA
TTCATCAGTTGAGAATCATTGTGAATTAGCTCAGTACCAGGC
ATAAAACGAACTAATATACCAGTCAGGAGCTGAGACTCCTCA
GGTGCCGTAAAGCATAGAGCTTGACGGGCTTTTCGGAACCTA
CACTACGTGAACCAAGGGAAGAAAGCGATGATGGCAATTCAT
CCAACGTCAAAGGGTGTAGCGGTCACGCACCAGAAGGAGCGG
TTCCAGTTTGGAACTAATGCGCCGCTACAAAAGTTTGAGTAA
CTTATAAATCAAAAGCACGTATAACGTGGACAACTCGTATTA
CGAAAATCCTGTTTTAAACAGGAGGCCGTACATTTGAGGATT
GAGAGTTGCAGCAACGCCAGAATCCTGAAGGAGCACTAACAA
GAGACGGGCAACAGCGAGTAAAAGAGTCAACAGTTGAAAGGA
GTTTGCGTATTGGGCAATACTTCTTTGAAAATATCAAACCCT
GCCAGCTGCATTAAAAGAACTCAAACTAAGCAGCAAATGAAA
CGTTGCGCTCACTGTATTACCGCCAGCCGTCAGTATTAACAC
AAGCCTGGGGTGCCTACCTACATTTTGAACCGAACGAACCAC
TCACAATTCCACACCATTGGCAGATTCATAATGCGCGAACTG
AATCATGGTCATAGCATTCTGGCCAACAAATACGTGGCACAG
GCAAGTCCGCTAGCATCATAATTACTAGCAAAGAACGCGAGA
GCTTGCATGCCTGCATACAAATTCTTACATATAACTATATGT
GTTTTCCCAGTCACGCTTAATTGAGAATGTCTGAGAGACTAC
AGGGGGATGTGCTGTTTAGGCAGAGGCAAGACGCTGAGAAGA
GCGATCGGTGCGGGAGTACCGACAAAAGTTTCCCTTAGAATC
AAAGCGCCATTCGCATAAACAACATGTTAGTGAATAACCTTG
CAGCCAGCTTTCCGAACAATAGATAAGTTTACCTTTTTTAAT
TGAGGGGACGACGATAATTTACGAGCATTCAAGAAAACAAAA
GTTGGTGTAGATGGTTCCTTATCATTCCTCATTTCAATTACC
CGTGGGAACAAACGCTCATCGAGAACAAGCTTTGAATACCAA
ATCAACATTAAATGATCATTACCGCGCCTACCTTTTACATCG
ATCAAAAATAATTCCTTATCCGGTATTCGTAGATTTTCAGGT
ATTTTTGTTAAATCCCCGACTTGCGGGATATCAAAATTATTT
TTTAAATTGTAAACTGCTATTTTGCACCGCCCCCTGCCTATC
ATCAGAAAAGCCCCAACGCTAACGAGCGGGGTCAGTGCCTTG
ATCGTAAAACTAGCAAAATAAACAGCCAGCTTTTGATGATAC
TGCCTGAGAGTCTGCGATTTTTTGTTTAGCGCAGTCTCTGAA
GGGTAGCTATTTTTCAGAGAGAATAACATATTCACAAACAAA
TATGATATTCAACCGAATTAACTGAACAGCATTGACAGGAGG
CAAAAGGGTGAGAACGCTAATATCAGAGCCCTCAGAGCCGCC
```

FIG. 17D

```
ATATTTTAAATGCACAATAATAAGAGCATCAGAGCCGCCACC
CCTTTATTTCAACGTACCGAAGCCCTTTTCAAAATCACCGGA
TACCAAAAACATTAAAGTTACCAGAAGGTCGGTCATAGCCCC
AATTAAGCAATAAATACCCAAAAGAACTTTGCCTTTAGCGTC
TAACATCCAATAAATATGTTAGCAAACGCCATCGATAGCAGC
GAGCTGAAAAGGTGATATAAAGAAACGGCACCATTACCATT
AATGGTCAATAACCGTCACAATCAATAGACTTGAGCCATTTG
GCGAACGAGTAGATGACAAAGGGCGACTGACGGAAATTATT
AACAACCATCGCCCGGGAAGGTAAATATATTCAACCGATTGA
TTTCTTAAACAGCTTATCACCGTCACCGAAAATTCATATGGT
GCCTTTAATTGTATCAAAATCACCAGTACAAAGACACCACGG
TTTTTCACGTTGAACGTCACCAATGAAATAGAAATACATAC
TGAGAATAGAAAGGCGACAGAATCAAGTGGCATGATTAAGAC
GTATGGGATTTTGCTTTCATCGGCATTTAAACCGAGGAAACG
AAAGTTTTGTCGTCCCATCTTTTCATAATTAAGAAAAGTAAG
GTAGCATTCCACAGCGGAACCGCCTCCCAGAAACAATGAAAT
CCGTAACACTGAGTCCTCAGAGCCACCAAGATAACCCACAAG
CCCTCATTTTCAGGCAGAGCCGCCGCCACCCTGAACAAAGTC
TCAGAACCGCCACCACGATTGGCCTTGATAAAACAGGGAAG
ATAGGTGTATCACCAGCCAGAATGGAAAACGTCAAAAATGAA
GGATAAGTGCCGTCAAGCGTCATACATGTATTATTTATCCCA
AGAGAAGGATTAGGAATAAGTTTTAACGTCTTTCCAGAGCCT
TTATTCTGAAACATTATAAACAGTTAATCAGCTACAATTTTA
CAATATAATCCTGAGTTAGAACCTACCAGGTTTTGAAGCCTT
AATTATCATCATATAATAAGAAATTGCTAAGAACGCGAGGC
CATTATCATTTTGCATATACAGTAACAGCAATAGCAAGCAAA
AATCCTTTGCCCGAGGATTCGCCTGATTGCAAGCCGTTTTTA
TAGAAGTATTAGACCAGAGGCGAATTATAAGAACGGGTATTA
CTAATAGATTAGAGTGATGAAACAAACAGTAGAAACCAATCA
ATTGAGGAAGGTTACAATTTCATTTGAACCTGAACAAGAAAA
CAATCAATATCTGGAATCAATATATGTGCAGCTAATGCAGAA
AATCTAAAGCATCACGCTATTAATTAATGTAAAGTAATTCTG
CGCCTGCAACAGTGGATAGCTTAGATTATTTTCGAGCCAGTA
CAGCAGAAGATAAATATCAAAATCATAGCGCCATATTTAACA
ATAGCCCTAAAACAGCTTAGGTTGGGTTCAGTATAAAGCCAA
ACAATATTTTTGAAATCCAATCGCAAGAAAAAGCCTGTTTA
```

FIG. 18A

```
CCATTGCAACAGGATTTGATAGCGAGGCTGCAAGGCGATTAA
TATCGGCCTTGCTGCTAGTACCCGTATAGGCCTCTTCGCTAT
GATTAGTAATAACAGTAATCATGGTCATGCCATTCAGGCTGC
TCTGTCCATCACGCGCTCACAATTCCACCGGCACCGCTTCTG
GAGAAGTGTTTTTATAAAGCCTGGGGTGGACAGTATCGGCCT
CGATTAAAGGGATTTGCGTTGCGCTCACGGGCGCATCGTAAC
TGCTTTCCTCGTTAGTGCCAGCTGCATTCGGCGGATTGACCG
ACAGGGCGCGTACTCGGTTTGCGTATTGTGTGAGCGAGTAAC
GCTGCGCGTAACCAGTGAGACGGGCAACTCGCGTCTGGCCTT
GAAAGGAGCGGGCGGAGAGAGTTGCAGCTCAGCTCATTTTTT
GGGAAAGCCGGCGAGGCGAAAATCCTGTACGTTAATATTTTG
AAATCGGAACCCTACCCTTATAAATCAACCAAAAACAGGAAG
ACCCAAATCAAGTTTGTTCCAGTTTGGAGCATGTCAATCATA
AAAAACCGTCTATCCTCCAACGTCAAAGTGGAGCAAACAAGA
TAAGGCTTGCCCTGACTTTAATCATTGTTTGAGAGATCTACA
TCATTACCCAAATCGCTCATTATACCAGCCGTTCTAGCTGAT
GGCTGACCTTCATCTAATAAAACGAACTAAAGGCCGGAGACA
AAAGAGGACAGATGGATTCATCAGTTGACAATGCCTGAGTAA
CGCAGACGGTCAATCAGATACATAACGCCGCAAGGATAAAAA
CGAAATCCGCGACCCAACACTATCATAATATGACCCTGTAAT
AAAGTACAACGGAGCAAAATAGCGAGAGAAGCCTCAGAGCAT
ACACTCATCTTTGAGGGTAATAGTAAAAAATCATACAGGCAA
AGGCACCAACCTAACGGAATCGTCATAATGGCATCAATTCTA
GAAGTTTCCATTAATAAACAGTTCAGAACCTGTTTAGCTATA
AACGGCTACAGAGGGGTCTTTACCCTGAATTTAGTTTGACCA
GTCACCCTCAGCAGCATCAAAAAGATTACATTCCATATAACA
CGCTGAGGCTTGCAGCGTTTTAATTCGACATGTTTTAAATAT
AATGACAACAACCAACTCCAACAGGTCAATGGCTTAGAGCTT
CGTAGAAAATACATATGCTGTAGCTCAAGCTTCAAAGCGAAC
CTGGCATGATTAAGGTGTCTGGAAGTTTAGAGGAAGCCCGAA
GGAAACCGAGGAAACTGCGAACGAGTAGCTATTATAGTCAGA
TTTTAAGAAAGTACAAATGGTCAATAAAACGAGAATGACCA
CAAGAAACAATGAAGCGAGCTGAAAAGGATATTCATTGAATC
AGAGATAACCCACAATTAACATCCAATATGTTTAGACTGGAT
CACCCTGAACAAAGAAAATTAAGCAATAGCTTTTGCAAAAGA
CATAAAAACAGGGATGTACCAAAACATCCCTCGTTTACCAG
TAACGTCAAAAATGAGCCTTTATTTCAACAAAAGGAATTACG
CATATTATTTATCCATATATTTTAAATGGATTTAGGAATACC
CGTCTTTCCAGAGCTTCAAAAGGGTGAGAACGGAACAACATT
CCCAGCTACAATTTAATATGATATTCAATCAGGACGTTGGGA
GAGGTTTTGAAGCCGAGGGTAGCTATTTGAATTACCTTATGC
TCTAAGAACGCGAGATTGCCTGAGAGTCGGATTGGGCTTGAG
CCCAATAGCAAGCATAATCGTAAAACTAACAAGAGTCCACTA
AAGCAAGCCGTTTTTAATCAGAAAAGCCAAGAATAGCCCGAG
```

FIG. 18B

```
CCAAGAACGGGTATTATTTAAATTGTAATTGATGGTGGTTCC
ATGTAGAAACCAATAAATTTTTGTTAAAAAGCGGTCCACGCT
GTCCTGAACAAGAACCATCAAAAATAATAGCTGATTGCCCTT
TTCAGCTAATGCAGTCATCAACATTAAAGGCGCCAGGGTGGT
AGGTAAAGTAATTCTCCGTGGGAACAAAAATGAATCGGCCAA
CATTTTCGAGCCAGACGTTGGTGTAGATTGCCCGCTTTCCAG
ATCGCCATATTTAATTTGAGGGGACGACCCTAATGAGTGAGC
ACCAGTATAAAGCCTCCAGCCAGCTTTCACAACATACGAGCC
AGAAAAAGCCTGTTGCAAAGCGCCATTCAGCTGTTTCCTGTG
ATAAGGCGTTAAATGGGCGATCGGTGCGAGGATCCCCGGGTA
CTGACCTAAATTTAAAAGGGGATGTGCAAGTCCGCTAGCGA
GCGAGAAAACTTTTGGGTTTTCCCAGTCTTGCATGCCTGCAG
AGGTCTGAGAGACTCTCAATCGTCTGAAAATACCTACATTTT
TAAGACGCTGAGAAAGTCACACGACCAGAATATTACCGCCAG
ATTTTCCCTTAGAAGATAGAACCCTTCTAGAAGAACTCAAAC
TGAGTGAATAACCTAGACAATATTTTTGAGCAATACTTCTTT
AATTACCTTTTTTATGATAGCCCTAAAAACCGAGTAAAAGAG
CATCAAGAAAACAAACCAGCAGAAGATATACGCCAGAATCCT
ATTCATTTCAATTAACCGCCTGCAACAGGCTAAACAGGAGGC
TTGCTTTGAATACCAAAATCTAAAGCATGAGCACGTATAACG
AGTACCTTTTACATCTCAATCAATATCTCTTAATGCGCCGCT
GCGTAGATTTTCAGGAATTGAGGAAGGTAGTGTAGCGGTCAC
CATATCAAAATTATAACTAATAGATTAGGAAGGGAAGAAAGC
GTTTGGATTATACTTTTAGAAGTATTAGTTTAGAGCTTGACG
CTGATTATCAGATGTAAATCCTTTGCCCTGCCGTAAAGCACT
AACAAAGAAACCACAACATTATCATTTTCTACGTGAACCATC
AAGCGCAGTCTCTGACTGGTAATAAGTTAACGAGTAGTAACG
GATATTCACAAACATGCCCGTATAAACAGCTCATTCAGTGAA
CAGCATTGACAGGATATTATTCTGAAACCAAGAACCGGATAT
CACCCTCAGAGCCGCAAGAGAAGGATTACAGGCGCATAGGCT
CCTCAGAGCCGCCAGCGGATAAGTGCCGACTGACCAACTTTG
AATCAAAATCACCGGAATAGGTGTATCATAGCCGGAACGAGG
TTTCGGTCATAGCCCCTCAGAACCGCCACTGATAAATTGTGT
GTTTGCCTTTAGCGCACCCTCATTTTCAACCAAGCGCGAAAC
AACCATCGATAGCATACCGTAACACTGAAAGAATACACTAAA
TAGCACCATTACCACTGTAGCATTCCACTAATGCCACTACGA
CGACTTGAGCCATTCTAAAGTTTTGTCGGACTTTTTCATGAG
ATTGACGGAAATTACTGTATGGGATTTTGGAACGAGGGTAGC
CAAAAGGGCGACATAGTGAGAATAGAAAGCTTTTGCGGGATC
CACAATCAATAGAAATTTTTTCACGTTGCCGATATATTCGGT
CAGACCGGAAGCAATCGCCCACGCATAAAAAATCTCCAAAAA
AGACTTCAAATATCGGGAGTTAAAGGCCGGAACAACTAAAGG
AGCAAAGCGGATTGCGAAAGACAGCATCGCTAAACAACTTTC
TAAATCAAAAATCACTTTGAGGACTAAATCTTTCCAGACGTT
```

FIG.18C

```
CCCCTCAAATGCTTACGGGTAAAATACGAGACAGCCCTCATA
AGCGTCCAATACTGAACGAAAGAGGCAAGTTTCGTCACCAGT
AGTTTTGCCAGAGGCCCCCAGCGATTATGGGATAGCAAGCCC
ACGACGATAAAAACATTTGTATCATCGCCCCTCAGAACCGCC
AGGCATAGTAAGAGTGCTCCATGTTACTCCGTACTCAGGAGG
ACATTCAACTAATGCATAAGGGAACCGATCGAGAGGGTTGAT
ATTACAGGTAGAAAAACGGTGTACAGACGGATTAGCGGGGTT
AGAAAAATCTACGTAAGAGTAATCTTGAATGAAAGTATTAAG
GATTTAAGAACTGAACGTAACAAAGCTGTTAATGCCCCCTG
ATGGTTTAATTTCAACGAGAAACACCAGTTAACGGGGTCAGT
TTAAAGAACGTGGAAGGGCGATGGCCCAGCCATGGCTTTTGA
ATAGGGTTGAGTGTTTTTGGGGTCGAGGGAACGTTATTAATT
GAAATCGGCAAAATAAGGGAGCCCCGAACTTTACAAACAAT
GGTTTGCCCCAGCAACGTGGCGAGAAAGAGCCGTCAATAGAT
CACCGCCTGGCCCTCTAGGGCGCTGGCATATCTAAAATATCT
TTTTCTTTTCACCACCACACCCGCCGCGGGTCAGTTGGCAAA
CGCGCGGGGAGAGGATGGTTGCTTTGACCACCTTGCTGAACC
TCGGGAAACCTGTCGAATCAGAGCGGGATGCCACGCTGAGAG
TAACTCACATTAATTTAGACAGGAACGGAAACAGAGGTGAGG
GGAAGCATAAAGTGTAATCAGTGAGGCCCATCGCCATTAAAA
TGAAATTGTTATCCAAATTAACCGTTGTAATGGCTATTAGTC
CCGAGCTCGAATTCTCACTTGCCTGAGTGACCTGAAAGCGTA
CCGTATACGCATGGGTAATATCCAGAACTAATAAAAGGGACA
GTCGACTCTAGACCAAAACGCTCATGGAATGGATTATTTACA
GTTGGGTAACGCCATCAAATATATTTTATTTATCAAAATCAT
TACGCCAGCTGGCGATGGTTTGAAATACGCGATAGCTTAGAT
GCAACTGTTGGGAAAAGAATAAACACCGGTCGCTATTAATTA
GTGCCGGAAACCAGTAGTATCATATGCGTAAATCAATATATG
CAGGAAGATCGCACAACGCTCAACAGTAAACAATTTCATTTG
CGTGCATCTGCCAGCAACGCCAACATGTGATGATGAAACAAA
TAATGGGATAGGTCTAATAAGAGAATATCGCAGAGGCGAATT
AACCCGTCGGATTCTGTCCAGACGACGAACGGATTCGCCTGA
CCTGTAGCCAGCTTAACGCGCCTGTTTAGAATATACAGTAAC
AACCAATAGGAACGAAATAATATCCCATGAAATAAAGAAATT
TTAAAATTCGCATTCAATAATCGGCTGTGGGTTAGAACCTAC
ATTGTATAAGCAAATAAACCAAGTACCGATATAATCCTGATT
TGTACCCCGGTTGATATTTTCATCGTAGTTATCATCATATTC
GAATCGATGAACGGAATCAGATATAGAAGTAAGCGTCATAGG
AAGGCTATCAGGTCGCGTTTTAGCGAACAAAGCCAGAATGGA
AAATTAATGCCGGATTAAATCAAGATTAAGACGATTGGCCTT
GTCAAATCACCATCTATCCTGAATCTTAACCAGAGCCGCCGC
TGTGTAGGTAAAGACTAATTTGCCAGTTACCCTCAGAGCCAC
TTTTTAGAACCCTCCAATCCAAATAAGAACCGGAACCGCCTC
ACTTTTGCGGGAGAAAAATAGCAGCCTTTGCCATCTTTTCAT
```

FIG. 18D

```
AAAGCTAAATCGGTAGCGCATTAGACGGGTTTTCATCGGCAT
GGCAAAGAATTAGCTCAGAGGGTAATTGAGCGACAGAATCAA
CTAATAGTAGTAGCAGAATTGAGTTAAGAACGTCACCAATGA
TTTTCATTTGGGGCATAGCAATAGCTATAGCAAAATCACCAG
TTAGATACATTTCGAGCAGATAGCCGAAATTATCACCGTCAC
GTTGATTCCCAATTCGCAATAATAACGGGAGGGAAGGTAAAT
GCAACTAAAGTACGACTCCTTATTACGCACCAGCGCCAAAGA
AATTGCTGAATATAACATAAGGTGGCATAAGTTTATTTTGT
AAAGGCTCCAAAAGAAGACACCACGGAAACATATAAAAGAAA
AATTGCGAATAATAAATTCATATGGTTTAGTATGTTAGCAAA
AACAGTTTCAGCGGTCAACCGATTGAGGAATACCCAAAAGAA
AGTAAATGAATTTTTTCATTAAAGGTGACAAAGTTACCAGAA
GTTAGCGTAACGATTGGGAATTAGAGCCCTTACCGAAGCCCT
ACAAACTACAACGCTTAGCAAGGCCGGACCCAATAATAAGAG
AATAGGAACCCATGGCACCGTAATCAGTAGCGCTAATATCAG
ACCCTCAGAGCCACTCAGACTGTAGCGCGAGAATTAACTGAA
TTTAGTACCGCCACCCCTTATTAGCGTTTACAGAGAGAATAA
ATAAGTATAGCCCGGAACCAGAGCCACCAACGATTTTTTGTT
TTGCTCAGTACCAGCCCTCAGAACCGCCACAAAATAAACAGC
AGGCTGAGACTCCTCCACCAGAACCACCCCAACGCTAACGAG
CCTATTTCGGAACCGGTTGAGGCAGGTCGTTGCTATTTTGCA
GCCTTGAGTAACAGAATAAATCCTCATTCTCCGACTTGCGG
TGATACAGGAGTGTAATTTACCGTTCCAGGCTTATCCGGTAT
TTAAAAGTTTGAGTCAGAAGGAGCGGAAGAATCATTACCGCG
TCGACAACTCGTATATGGCAATTCATCACACTCATCGAGAAC
AATACATTTGAGGATCTGAATAATGGAACTTTCCTTATCATT
TTAGGAGCACTAACTTGCACGTAAAACACCTAATTTACGAGC
TCAACAGTTGAAAGGTTTAACGTCAGATTCAACAATAGATAA
TCAAATATCAAACCCGGGAGAAACAATACAATAAACAACATG
CCAGCAGCAAATGAAAGTTACAAAATCGAAAGTACCGACAAA
CGGTCAGTATTAACCCTGAGCAAAAGAAAATTTAGGCAGAGG
ATACCGAACGAACCAATTAATTACATTTGGGCTTAATTGAGA
TTTAATGCGCGAACATGGAAACAGTACATTATACAAATTCTT
AGAATACGTGGCACTGCTTCTGTAAATCGAATCATAATTACT
TTCTGGCCAACAGATCCTTGAAAACATACGACCGTGTGATAA
TTGGCAGATTCACCGAGTCAATAGTGAAGTTAATTTCATCTT
```

NUCLEIC ACID NANOTUBE LIQUID CRYSTALS AND USE FOR NMR STRUCTURE DETERMINATION OF MEMBRANE PROTEINS

RELATED APPLICATIONS

This application claims the benefit of priority to U.S. Provisional Application Ser. No. 60/793,788, filed Apr. 21, 2006, and U.S. Provisional Application Ser. No. 60/904,266, filed Feb. 28, 2007.

TECHNICAL FIELD

The invention generally relates to nucleic acid nanotubes. More particularly the invention relates to compositions and methods for making nucleic acid nanotubes that are suitable for performing liquid-crystal NMR spectroscopy of detergent-solubilized membrane proteins.

BACKGROUND

Structure determination of membrane proteins is an important challenge for biomedical science. About thirty percent of expressed proteins span lipid bilayers, yet structures of only about one hundred membrane proteins have been resolved. Membrane proteins are encoded by 20-35% of genes but represent fewer than one percent of known protein structures to date. Knowledge of their structures will be enormously insightful for cell biology. Furthermore, membrane proteins are important as drug targets. The slow rate of membrane-protein structure determination represents a significant bottleneck for both basic and applied bioscience discovery. This bottleneck largely derives from difficulties in forming well-ordered three-dimensional crystals of membrane proteins. Solution NMR presents an attractive alternative for the study of membrane proteins, as high-resolution structural information can be obtained for proteins up to 80 kD in size without the need for crystallization. Residual dipolar couplings (RDC's), commonly measured for biological macromolecules weakly aligned by liquid-crystalline media, are important global angular restraints for NMR structure determination. For membrane proteins greater than 15-kDa in size, Nuclear-Overhauser-effect (NOE)-derived distance restraints are difficult to obtain, and RDC's could serve as the main reliable source of NMR structural information. In many of these cases, RDC's would enable full structure determination that otherwise would be impossible. However, none of the existing liquid-crystalline media used to align water-soluble proteins are compatible with the detergents required to solubilize membrane proteins.

For solution NMR, macromolecules must be solubilized in water to facilitate fast tumbling; the faster the tumbling, the better the spectra. To promote water solubility, membrane proteins must be complexed with detergent micelles. The micelle-protein complex is considerably larger than the protein alone, and tumbling is relatively slow as a result. This increase in effective size is especially problematic for α-helical membrane proteins greater than 15 kD in size, where resonance peaks are closely spaced and become irresolvable with the fast coherence relaxation of slowly tumbling macromolecules. In order to obtain information about the internuclear angles, each protein must be made to tumble in a weakly ordered regime. The appropriate weak ordering, about 0.1%, can be achieved by dissolving the protein in an appropriate concentration of a suitable alignment material. For example, water-soluble proteins can be aligned weakly by a suitable amount with ~1.5-2% Pfl filamentous phage, which forms a liquid crystal at that concentration. The easiest method for weak alignment of proteins is through mixing the protein with a liquid-crystalline medium, such as Pfl filamentous phage, DMPC/DHPC bicelles, C12E5 polyethylene glycol, or cellulose crystallites. However, none of these media are compatible with detergent-solubilized membrane proteins.

The general applicability of solution NMR spectroscopy to structural characterization of intact α-helical membrane proteins has been demonstrated by the structure determination of the 15-kDa Mistic protein and the 30-kDa pentameric phospholamban, as well as the complete assignment of backbone resonances and secondary structures of the 44-kDa trimeric diacylglycerol kinase and the 68-kDa tetrameric KcsA potassium channel. Despite such progress, full-scale structure determination of α-helical membrane proteins remains challenging and rare. Due to the large fraction of methyl-bearing residues in membrane proteins and to the added molecular weight of detergent micelles, the low chemical-shift dispersion of α-helical proteins is obscured by resonance overlap and line broadening, making assignment of side-chain methyl resonances extremely difficult. Without side-chain chemical shifts, it is impossible to obtain a sufficient number of long-range NOE-derived distance restraints for folding secondary segments into the correct tertiary structure. Therefore, development of alignment media for accurate RDC measurements from α-helical membrane proteins would enhance significantly the capability of solution NMR in structure determination of this important class of targets.

The most effective method for weak alignment involves mixing the protein of interest with large particles that form stable liquid crystals at low concentration (~1.5-5% w/v). Liquid crystals that have been used to align water-soluble proteins include DMPC/DHPC-bicelle liquid crystals, filamentous phage particles, ternary mixtures of cetylpyridinium Cl/Br, hexanol, and sodium Cl/Br, binary mixtures of polyethylene glycol and hexanol, and cellulose crystallites. However, none could be applied to membrane proteins due to incompatibility with the zwitterionic or anionic detergents typically used to solubilize membrane proteins for structural study. The only method currently available for weak alignment of membrane proteins involves the use of strained (radially or axially compressed) polyacrylamide gels. However, dissolving protein-micelle complexes to high concentration in gels is notoriously difficult due to the inhomogeneous pore size of randomly cross-linked gel matrices. Thus the measured RDC's are of limited accuracy.

Nucleic acid nanotube liquid crystals can extend the advantages of weak alignment to NMR structure determination of a broad range of detergent-solubilized membrane proteins. Alignment media comprised of 800 nm heterodimer DNA nanotubes should be broadly useful for providing global structural restraints in solution NMR studies of membrane proteins. As a large number of helical membrane proteins of great biomedical interest are between 20-30 kDa in size—well below the current size limitation of solution NMR spectroscopy—new experimental systems for obtaining NMR structural information in the presence of detergents are of fundamental importance. DNA nanotechnology, which affords versatile molecular design and sub-nanometer-scale precision, has been pursued as a route towards building host lattices to position guest macromolecules for crystallographic structural studies. The present invention employs solution NMR instead of crystallographic methods, and validates the potential of DNA nanotechnology for imposing order on target macromolecules to acquire atomic-resolution structural information.

SUMMARY OF THE INVENTION

The invention is related to novel compositions and methods for preparing liquid crystalline solutions of nucleic acid nanotubes suitable for performing liquid-crystal NMR spectroscopy of proteins, including detergent-solubilized membrane proteins. By virtue of being constructed from nucleic acids, these nanotubes generally are resistant to detergents, and can be constructed, for example, to mimic the shape and size of filamentous phage particles.

It is an object of the invention to provide a composition comprising nucleic acid nanotubes having uniform length. Each nanotube comprises a plurality of linked double-stranded nucleic acid helices, and each nanotube is formed from at least one single-stranded scaffold nucleic acid molecule and a plurality of staple oligonucleotides. The nucleic acid can be DNA. The nucleic acid nanotubes can form a liquid-crystalline phase in solution, and proteins solubilized in detergent can be aligned weakly using the nanotube liquid crystals.

A further object of the invention is to provide nucleic acid nanotubes in which the average length of the nucleic acid nanotubes is given by the length of the single-stranded scaffold nucleic acid divided by the number of double stranded nucleic acid helices comprising each nanotube. In some embodiments the length of the helices comprising the nucleic acid nanotubes varies by no more than 20% of the average length of the helices, and in certain embodiments by no more than 10% of the average length of the helices. The length of the nucleic acid nanotubes is greater than about 50 nanometers, and about 400 nanometers. The nanotubes comprise at least 3 adjacent double-stranded helices. In certain embodiments the nanotubes consist of 5, 6, or 7 adjacent helices. In other embodiments, DNA heterodimer nanotubes 800 nanometers in length can be constructed from 400 nanometer monomers of two types, one type of monomer self-assembling with the second type of monomer.

A further object of this invention is to provide a method of preparing nucleic acid nanotubes. The method comprises preparing a solution comprising a single-stranded scaffold nucleic acid and a plurality of staple oligonucleotides, heating the solution to denature the scaffold nucleic acid and staple oligonucleotides, and cooling the solution to room temperature. The nucleic acid nanotubes thus formed will have a uniform length.

A further object of this invention is to provide a method to perform liquid-crystal NMR spectroscopy of proteins using nucleic acid nanotubes. The method comprises suspending nucleic acid nanotubes in a solution, forming a liquid crystalline phase comprising the nucleic acid nanotubes, adding a protein to the solution, performing NMR spectroscopy on the protein and nucleic acid nanotube mixture. In some embodiments, the protein added to the solution is solubilized in detergent. In other embodiments, the protein is a membrane protein solubilized in detergent. In other embodiments, the protein is present at a concentration of at least 0.1 mM.

Further features and advantages of the invention and further embodiments will become more fully apparent in the following description of the embodiments and drawings thereof, and from the claims.

BRIEF DESCRIPTION OF THE DRAWINGS

FIG. 1a is a stylized 3-dimensional representation highlighting the 14 nm segment that forms the junction between the two 400 nm monomers.

FIG. 1b is a segment diagram in which each monomer consists of 28 segments of length 42 base pairs, as well as a head and tail segment on each end.

FIG. 1c is a schematic of the two scaffold strands of each monomer (without the complementary staple oligonucleotides), each monomer consisting of a modified M13 bacteriophage single-stranded DNA genome of length 7308 bases.

FIG. 1d is a cross-sectional schematic view of the DNA nanotube shown in

FIG. 1a.

FIG. 1e is a schematic of the 14 nm junction between the linked nanotube monomers, showing the 42 base pair link between the two scaffold strands and their complementary staple strands.

FIG. 1f is a schematic of a typical 42 base pair segment of the completed nanotube, showing that a crossover pattern consisting of six staple strands repeats itself every 42 base pair segment along the length of the nanotube.

FIGS. 3a and 3b show, respectively the "capped" scaffold-plus-staples head, and the unpaired scaffold and staple strands of the tail of the front monomer.

FIGS. 3c and 3d show, respectively, the unpaired scaffold and staples of the head, and the "capped" scaffold-plus-staples tail of the rear monomer.

FIG. 3e shows the inter-monomer junction of a DNA heterodimer nanotube, in which the unpaired scaffold and staples of the front monomer are complementary to and join with the unpaired staples and scaffold of the rear monomer.

FIGS. 4A-4D shows a Python computer program script for the sequence determination of the components of six-helix bundle DNA nanotubes.

FIGS. 5A-5B is the Python computer program script used to generate front monomer core oligonucleotides and head caps.

FIGS. 6A-6B is the Python computer program script used to generate rear monomer core oligonucleotides and tail caps.

FIGS. 7A-7B is the Python computer program script used to generate front monomer tail connector oligonucleotides and rear head connector oligonucleotides.

FIG. 8 shows the sequences used in the example for front monomer head cap staples of a six-helix bundle DNA nanotube (SEQ ID NOS 1-3, respectively, in order or appearance).

FIG. 9 shows the sequences used in the example for front monomer tail connector staples of a six-helix bundle DNA nanotube (SEQ ID NOS 4-6, respectively, in order or appearance).

FIG. 10 shows the sequences used in the example for rear monomer head connector staples of a six-helix bundle DNA nanotube (SEQ ID NOS 7-9, respectively, in order or appearance).

FIG. 11 shows the sequences used in the example for rear monomer tail cap staples of a six-helix bundle DNA nanotube (SEQ ID NOS 10-13, respectively, in order or appearance).

FIGS. 12A-C is the sequence of the M13 mp 18 derived single stranded DNA scaffold used in the DNA nanotube of FIG. 2 (SEQ ID NO: 14).

FIGS. 13A-D lists the sequences of each of the staple oligonucleotides that build to the scaffold DNA used in the DNA nanotube of FIG. 2 (SEQ ID NOS 15-195, respectively, in order or appearance).

FIG. 14 shows a computer-generated random 59-base sequence inserted into M13 mp 18 at insert position 6258 to generate recombinant M13 filamentous bacteriophage (SEQ ID NO: 196).

FIG. 15 shows the sequences that were used in the example to construct the M13 mp 18 insert fragment of FIG. 14, together with flanking regions (109 base pairs total) (SEQ ID NOS 197-202, respectively, in order or appearance).

FIGS. 16A-C show the recombinant M13 filamentous bacteriophage genome sequence used in the example that serves as the input to all Python scripts to generate the scaffold strand of the DNA nanotubes (SEQ ID NO: 14).

FIGS. 17A-D list the sequences used in the example for front monomer core staples of a six-helix bundle DNA nanotube (SEQ ID NOS 15-182, respectively, in order or appearance).

FIGS. 18A-D list the sequences used in the example for rear monomer core staples of a six-helix bundle DNA nanotube (SEQ ID NOS 203-370, respectively, in order or appearance).

FIG. 21 shows analysis of DNA nanotubes.

FIGS. 22 a-f show negative-stain electron micrographs of DNA monomers and heterodimers.

DETAILED DESCRIPTION

Definitions

Figure 1:
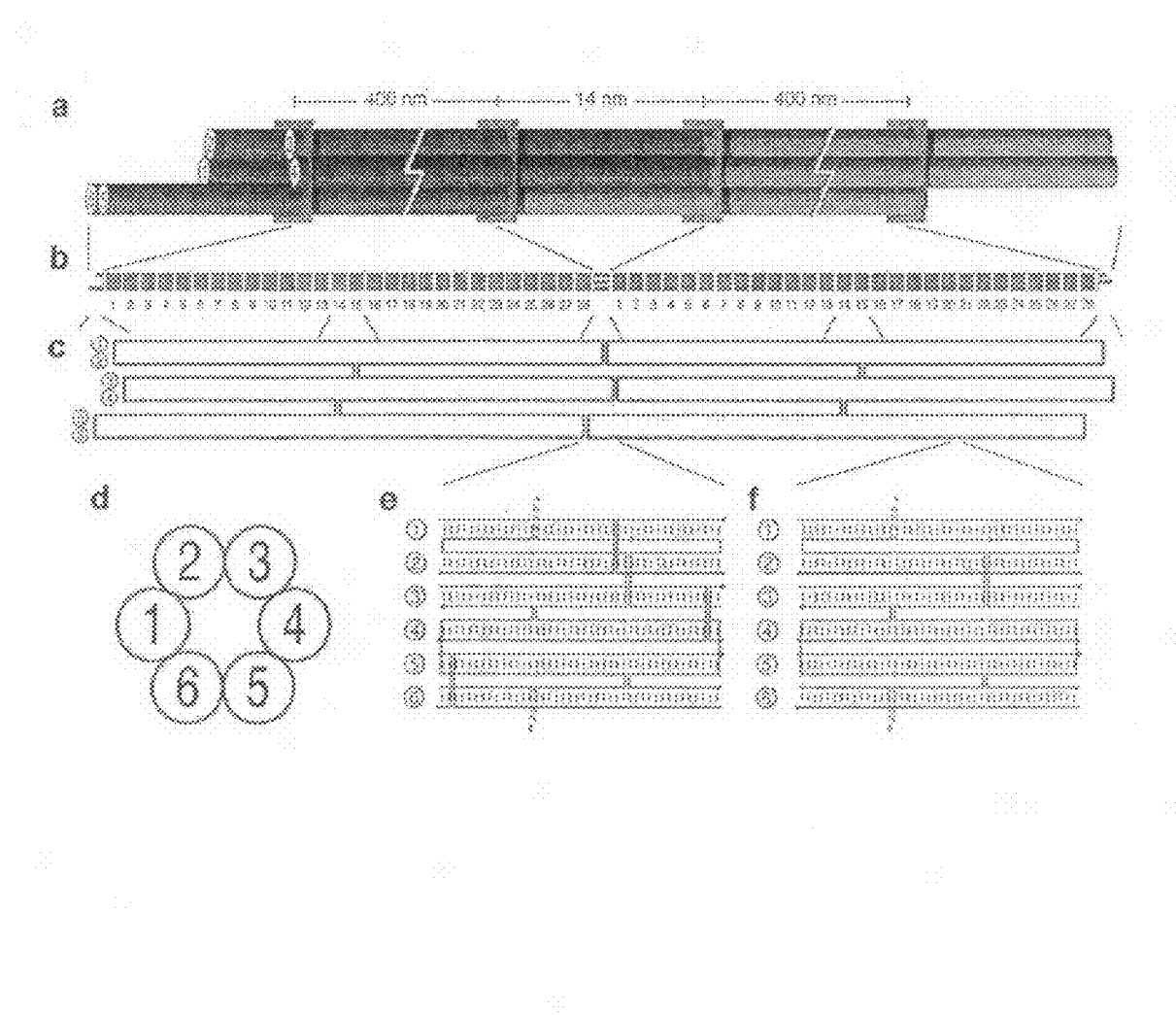
FIG. 1 shows various representations of a 800 nm DNA nanotube heterodimer.

The term "nanotube" as used herein refers to a cylindrical arrangement of nucleic acid helices aligned in parallel and linked to one another, forming a tubular structure with approximate radial symmetry around a central axis.

The term "scaffold nucleic acid" as used herein refers to a single-stranded nucleic acid that is able to fold into various conformations through the complementary binding of shorter single-stranded nucleic acids (staple oligonucleotides) to non-contiguous segments of the longer nucleic acid.

The term "staple oligonucleotide" as used herein refers to a single-stranded oligonucleotide with successive segments that are complementary to non-contiguous segments of a scaffold, each scaffold segment forming part of a different helix in a nucleic acid nanotube. As used herein, the term "staple" refers to staple oligonucleotide.

The term "crossover" as used herein refers to the point at which a staple oligonucleotide crosses over from a binding site on one helix to a binding site on an adjacent helix in a nucleic acid nanotube. A crossover comprises either a covalent bond joining atoms in adjacent helices or a chemical group which is covalently linked to atoms in adjacent helices. The chemical group can be, for example, a phosphate group which forms part of the nucleic acid backbone of a staple oligonucleotide.

The term "seam" as used herein refers to the point at which a scaffold nucleic acid crosses from one helix to an adjacent helix. A seam comprises either a covalent bond joining atoms in adjacent helices or a chemical group which is covalently linked to atoms in adjacent helices. The chemical group can be, for example, a phosphate group which forms part of the nucleic acid backbone of a scaffold nucleic acid.

DESCRIPTION

The inventors have discovered how to make nucleic acid nanotubes of a uniform length that will self-assemble into liquid crystals. A solution comprising liquid crystalline nucleic acid nanotubes is resistant to detergent and enables liquid-crystal NMR spectroscopy of membrane proteins solubilized in detergent. Rod-like molecules are more likely to self-assemble into liquid crystals if they have large aspect ratios (length-to-cross-section diameter) and if they are homogeneous in length.

Nucleic acid nanotubes have been prepared using DNA origami techniques. These nanotubes can form detergent-resistant liquid crystals that make possible the accurate measurement of NMR residual dipolar couplings (RDC's) for a wide array of detergent-solubilized proteins. Acquisition of RDC's, which encode global orientation constraints, facilitates the de novo NMR structure determination of polytopic alpha-helical membrane protein monomers larger than 15 kDa in size. The previous size limit for solution-NMR-based de novo structure determination of membrane proteins can be extended by employing liquid-crystalline nucleic acid nanotubes to facilitate the accurate measurement of residual dipolar couplings, from which global orientation information can be derived. Thus these nanotube liquid crystals have made feasible the structure determination of a wide range of biomedically important targets that currently are very difficult to characterize.

Multi-helix bundle nucleic acid nanotubes were prepared by adapting the scaffolded DNA origami technique described by Rothemund (Rothemund, P. W., J. Biomol. Struct. Dyns. 22, addendum, 2005; and Rothemund, P. W., Nature 440, 297-302, 2006; both hereby incorporated by reference in their entireties). In one embodiment, the origami technique was used to create a six-helix bundle DNA-nanotube architecture similar to that described by Mathieu et. al (Nano Lett. 5, 661-5, 2005). The scaffold DNA used to construct the multibundle DNA nanotubes can be one or more long single-stranded DNA molecules of known sequence. To the scaffold are added many short staple oligonucleotides with complementarity to at least two sections of the scaffold DNA, the staple oligonucleotides force the scaffold into the shape of an array of parallel double helices. This construction technique permits the construction of bundles comprising various numbers of helices, and of predictable lengths. The length of a bundle is determined by the length of the scaffold DNA, which is folded using the staple oligonucleotides into approximately equal smaller lengths of DNA helices that are linked to one another. The average length of the nanotubes is given by the length of the single-stranded scaffold strand divided by the number of double-stranded helices present in each nanotube. Each helix is linked to an adjacent helix by at least two of the staple oligonucleotides which cross over to an adjacent helix. The bundles are linked together in this manner to form a closed tube-like structure. In a preferred embodiment of this invention, six-helix bundle DNA nanotubes were assembled by combining a single-stranded scaffold DNA with a plurality of oligonucleotides complementary to segments of the scaffold, in a manner that causes the length of the DNA nanotube to be one-sixth of the length of a DNA double helix comprising the scaffold as one strand. Thus, adapting the DNA origami technique to the preparation of DNA nanotubes results in nanotubes of predictable and uniform length and aspect ratio.

The nanotubes of the present invention are particularly well-suited to forming liquid crystals useful in a variety of applications. Moreover, the efficiency of producing a liquid crystal nanotube solution is substantially improved with the present methods. Competition for binding to the scaffold is likely to select for those oligonucleotides with fewer defects, thus mitigating somewhat complications from using chemically-synthesized oligonucleotides. This strategy allows for flexibility in the length of each double helix in the array, as well as in the angle of curvature between any three parallel helices. The result is a robust and facile method. This method does not require any sequence design for the scaffold, nor does it require purification of the oligonucleotides. Thus the amount of labor required for assembly of such structures is reduced greatly compared to previous methods, and the material costs are relatively low.

Sequence Structure of the Nucleic Acid Nanotubes

The basic strategy of preparing DNA origami structures is described by Rothemund (Rothemund, P. W., J. Biomol. Struct. Dyns. 22, addendum, 2005; and Rothemund, P. W., Nature 440, 297-302, 2006; both hereby incorporated by reference in their entireties). According to the invention, one or more scaffold nucleic acids are combined with a plurality of staple oligonucleotides whose sequences are chosen to form complementary base pairings with the scaffold strand(s), thereby causing the scaffold to fold into a framework which, together with the base-paired staple oligonucleotides, forms three or more double helices linked side to side (i.e., a multi-helix bundle) to form a nanotube.

The double helices comprising each component of a multi-helix bundle can be rendered as a sketch drawing, followed by conversion of the general structure into an Adobe Illustrator file that indicates the details of the spacing between scaffold crossovers and oligonucleotide crossovers. The minimum distance between scaffold crossovers and oligonucleotide crossovers on adjacent lines is about 10 base pairs. In a preferred embodiment, the DNA nanotube structure mimics the shape and size of Pfl, a rod-like viral particle that is 6 nm in diameter and 2 μm in length. Its structural rigidity and negative-charge surface density allow it to form a stable and useful liquid crystal at low concentrations. To achieve a Pfl-like DNA structure, a six-helix bundle DNA-nanotube architecture can be adopted. This design resembles a parallel array of six double helices for which every set of three adjacent helices frames a dihedral angle of 120 degrees (FIGS. 1a and 1d). Adjacent double helices are held together by Holliday-junction crossovers that occur every 42 base pairs (FIG. 1f). For each monomer, a 7308-base, M13-derived single-stranded circle of DNA (New England Biolabs) is employed as a "scaffold" and 168 single strands of DNA of length 42 bases, programmed with complementarity to three separate 14-base regions of the scaffold, are employed as staple oligonucleotides ("staples") (FIG. 1f). The distance between scaffold crossovers and oligonucleotide crossovers on adjacent lines is 42 base pairs, which results in good scaffold folding kinetics and thermodynamics. The staples self-assemble with the scaffold into the shape of six parallel double helices curled into a tube.

Each pair of adjacent helices should have at least two crossovers in order to enforce parallelism between the helices. The distance between oligonucleotide crossovers along a given line must be an even number of half-turns, usually 32, 42 or 52 base pairs, leading to a pitch spacing of 10.7 base pairs, 10.5 base pairs, or 10.4 base pairs, respectively. The distance between scaffold and oligonucleotide crossovers must be an odd number of half-turns. For the 32 base pair spacing, this corresponds to distances of 16+16 and 5+27 base pairs. For the 42 base pair spacing, this corresponds to distances of 16+26 and 5+37 base pairs. For the 52 base pair spacing, this corresponds to distances of 26+26, 16+36, and 5+47 base pairs. In one embodiment, a five-helix bundle structure requires a 108 degree angle between any three adjacent helices. At 10.8 base pairs per turn, 14 base pairs yields 1.30 turns, yielding a rotation along the helix of 360+108 degrees. In another embodiment, a seven-helix bundle structure requires a 128.5 degree angle between any three adjacent helices. At 10.33 base pairs per turn, 14 base pairs yields 1.1355 turns, which is a rotation along the helix of 360+128 degrees.

In a preferred embodiment, a six-helix bundle requires a 120 degree angle between any three adjacent helices. With 42 base pairs between crossovers, the average twist of the helix is 10.5 base pairs per turn. At 10.5 base pairs per turn, 14 base pairs yields 1.33 turns, which is a rotation along the helix of 360+120 degrees. There are 42 base pairs between colinear crossovers (crossovers to the same adjacent helix), and either 14 or 28 crossovers along any helix to either adjacent helix. This implementation of the six-helix bundle uses oligonucleotides that are all 42 bases long, and whose ends line up with the positions of oligonucleotide crossovers on adjacent lines.

This positioning is favorable in that chemical moieties added to the ends of the oligonucleotides will extend out from the helix orthogonal to the convex surface of the six-helix bundle.

Figure 2:
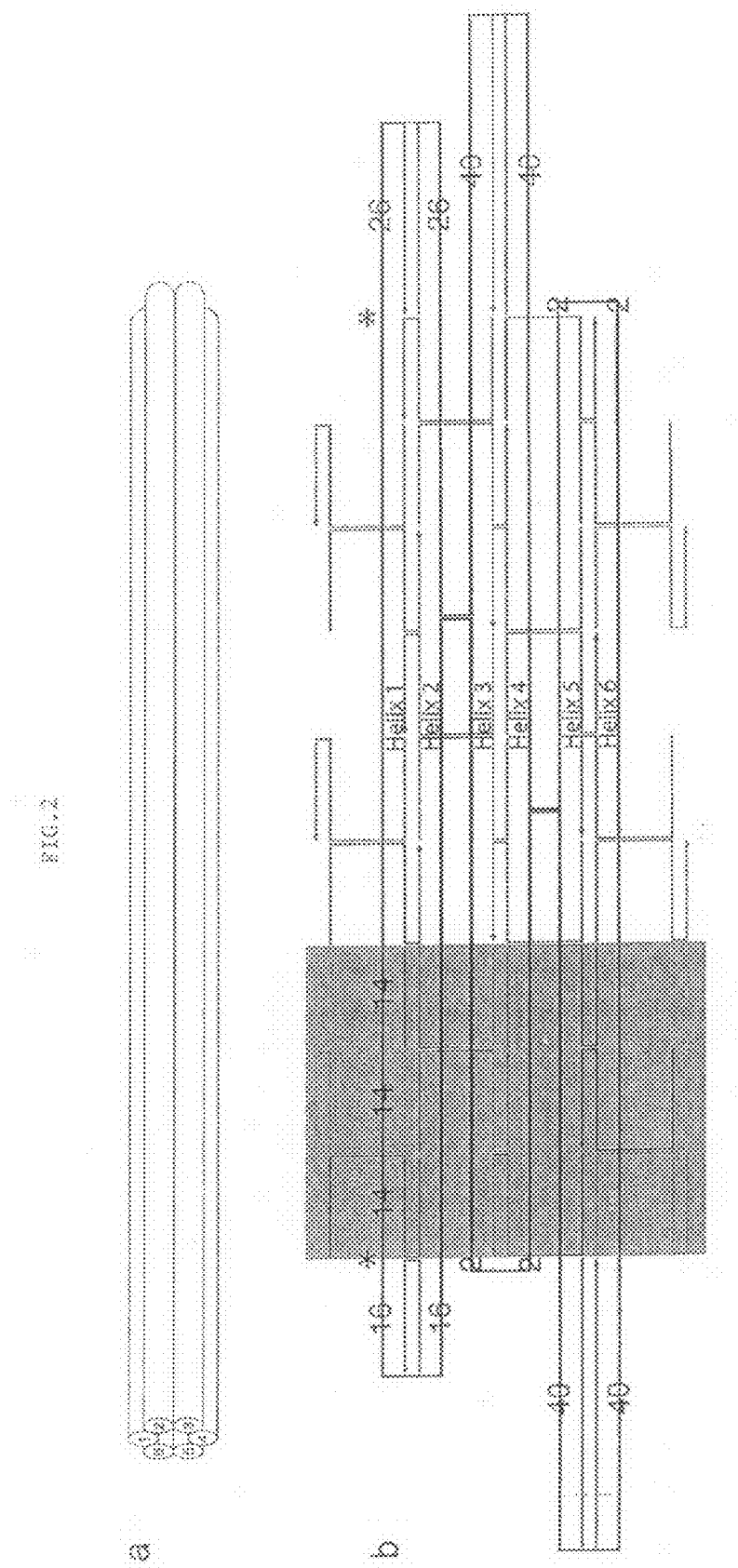
FIG. 2A is a schematic representation of a six-helix bundle DNA nanotube.
FIG. 2B is a representation of the arrangement of scaffold strand and staple oligonucleotides of the six-helix DNA nanotube of FIG. 2A. The dark line represents the uninterrupted scaffold DNA, folded into a six-strand arrangement, with a seam formed between helix 2 and helix 3, and another seam between helix 4 and helix 5. The staple oligonucleotides are generally 42 bases long, each contributing three 14-base segments, one to each of three adjacent portions of the scaffold DNA.

In a six-bundle DNA nanotube, there are six DNA helices, and the scaffold is divided into six virtual strands. The top and bottom virtual strands depicted in FIG. 2A are continuous fragments of the scaffold. The middle four virtual strands each are composed of two pieces of the scaffold strand, separated by the strand seam. A 7308 base scaffold DNA strand results in virtual strands that are 7308/6 or 1218 bases long. Using a 42 base pair structure for the oligonucleotides, there are 29 pseudo-repeats of the basic staple oligonucleotide structure. The scaffold structure in the preferred embodiment is as follows, with the numbers representing the relative values of the base pair positions:

0-1217: virtual strand 1
  1218-1829: upstream component of virtual strand 2
  1830-2455: downstream component of virtual strand 3
  2456-3109: upstream component of virtual strand 4
  3110-3725: downstream component of virtual strand 5
  3726-4943: virtual strand 6
  4944-5545: upstream component of virtual strand 5
  5546-6109: downstream component of virtual strand 4
  6110-6701: upstream component of virtual strand 3
  6702-7303: downstream component of virtual strand 2

For helix 1, the first oligonucleotide strand attachment starts at position 16 from the 5' end of the virtual strand 1 at the proximal end of the nanotube, and binds a 14-base section of virtual strand 1 with a 14-base section of virtual strand 2 and a 14-base section of virtual strand 6. For helix 2, the first oligonucleotide strand attachment starts at position 26 from the 5' end of virtual strand 2 at the distal end of the nanotube, and binds a 14-base section of virtual strand 1 to a 14-base section of virtual strand 2 and a 14 base section of virtual strand 3. For helix 3, the first oligonucleotide strand attachment starts at position 2 from the 5' end of virtual strand 3 at the proximal end of the nanotube, and binds a 14-base section of virtual strand 3 to a 14-base section of virtual strand 4 and a 14-base section of virtual strand 5. For helix 4, the first oligonucleotide strand attachment starts at position 40 from the 5' end of virtual strand 4 at the distal end of the nanotube, and binds a 14-base section of virtual strand 4 to a 14-base section of virtual strand 5 and a 14-base section of virtual strand 6. Most of the staple oligonucleotides in this embodiment are 42 base pairs long and attach to three non-contiguous sections of the scaffold DNA to produce the appropriate folding to generate the six-helix bundle nanotube.

A monomer can be conceptualized as a series of 28 pseudo-repeat segments, each consisting of six parallel double helices that are 42 base pairs long, flanked by jagged overhangs on either end of the object (FIG. 1b). Each segment can be conceptualized as a series of three subsegments, for which every double helix is 14 base pairs long (FIG. 1f). Six of the twelve strands of a subsegment are provided by the scaffold strand, three are provided by one staple strand, and three by another staple strand. Adjacent subsegments are related by 120-degree screw pseudosymmetry. The scaffold generally does not cross over between helices, except for four times in the middle of each monomer to produce a "seam", and three times on each monomer end (FIG. 1c).

DNA nanotube monomers can be multimerized using the appropriate design parameters. The inclusion of a seam in the design allows for the linkage of monomers in a head-to-tail fashion instead of in a head-to-head fashion, as is evident from consideration of the polarity of the scaffold strand within each double helix (FIG. 3e). Three extra staple strands block the head of the front monomer, and four extra staple strands block the tail of the rear monomer (FIGS. 3a and 3d). To facilitate heterodimerization, three extra staple strands with unpaired bases decorate the tail of the front monomer, and three extra staple strands with unpaired bases decorate the head of the rear monomer (FIGS. 3b and 3c).

The model is then converted into DNA sequences; this can be accomplished, for example, by coding performed by a Python program. An example is provided in FIGS. 4A-4D. The program performs the following tasks: (1) input the scaffold strand sequence; (2) break the scaffold strand sequence into virtual strands corresponding to each parallel double helix; (3) break each virtual strand into complementary sequence tokens; and (4) generate the oligonucleotide sequences as catenated tokens.

For nanotube heterodimerization, a computer program can be written to generate staple strand sequences given the sequence of the scaffold (See Figures S3a-c). A first Python script can be used to generate front monomer core oligonucleotides and head caps (FIGS. 5A-5B). A second Python script can be used to generate rear monomer core oligonucleotides and tail caps (FIGS. 6A-6B). A third Python script can be used to generate front monomer tail connector oligonucleotides and rear head connector oligonucleotides (FIGS. 7A-7B). Using two cyclic permutations of the scaffold sequence as input to the program can generate independent sets of staple-strand sequences for folding two different monomer nanotubes. Therefore copies of the same scaffold molecule can be used to generate two chemically-distinct species.

It is understood that many possible sequence combinations exist which can give rise to a given nanotube structure. The initial choice of scaffold strand sequence will determine the sequences of the staple oligonucleotides. However, once a particular scaffold strand is chosen, any given point along the sequence of the scaffold strand can be chosen as a starting point to build the nanotube structure. The choice of scaffold sequence and starting point, together with the nanotube geometry and the number and position of crossovers and seams, will determine the sequences of the staple oligonucleotides. Furthermore, the sequences of staple oligonucleotides can be optimized in order to avoid unintended binding that can give rise to defective structures or poor assembly kinetics.

Length of the DNA Nanotubes

The length of the DNA nanotubes is 50 nm or more. In one embodiment of the invention, the length of the DNA nanotubes is 200 nm or more. In a preferred embodiment, the length of the DNA nanotubes is about 400 nm. A length of 400 nm can be achieved, for example, with a scaffold DNA strand 7308 bases long folded into six strands to which complementary staple oligonucleotides are bound, forming six-helix bundles. Preferably, the length of the nanotubes varies by no more than 20% of the average length of the nanotubes, and more preferably by no more than 10% of the average length of the nanotubes. If a nanotube comprises helices of different lengths, then the length of the longest helix is considered the length of the nanotube.

The lengths of the nanotubes formed using this technique can also be modified through end-to-end multimerization of the bundle structures. In a preferred embodiment of the invention, head-to-head and tail-to-tail multimerization of the bundles can be generated from a scaffold DNA configuration in which the bends of the scaffold occur only at the ends of the bundles. In a more preferred embodiment of the invention, head-to-tail multimerization of the DNA bundles can be generated from a scaffold configuration in which some of the scaffold bends occur within the length of the DNA bundles, forming a seam across which the scaffold DNA does not cross.

In a preferred embodiment, the virtual strands are connected to each other by the staple oligonucleotides in a staggered manner. Virtual strands 1 and 2 (see FIG. 2B) each have 16 base pairs available for multimerization on the proximal end of the nanotube, and 26 base pairs available for multimerization on the distal end. Virtual strands 3 and 4 each have 2 base pairs available for multimerization on the proximal end of the nanotube, and 40 base pairs available for multimerization on the distal end. Virtual strands 5 and 6 each have 40 base pairs available for multimerization on the proximal end of the nanotube, and 2 base pairs available for multimerization on the distal end. Thus the connecting region for each multimerized strand is 42 bases long, maintaining a constant staple oligonucleotide length and allowing for head-to-tail multimerization of the DNA nanotubes.

Figure 3:
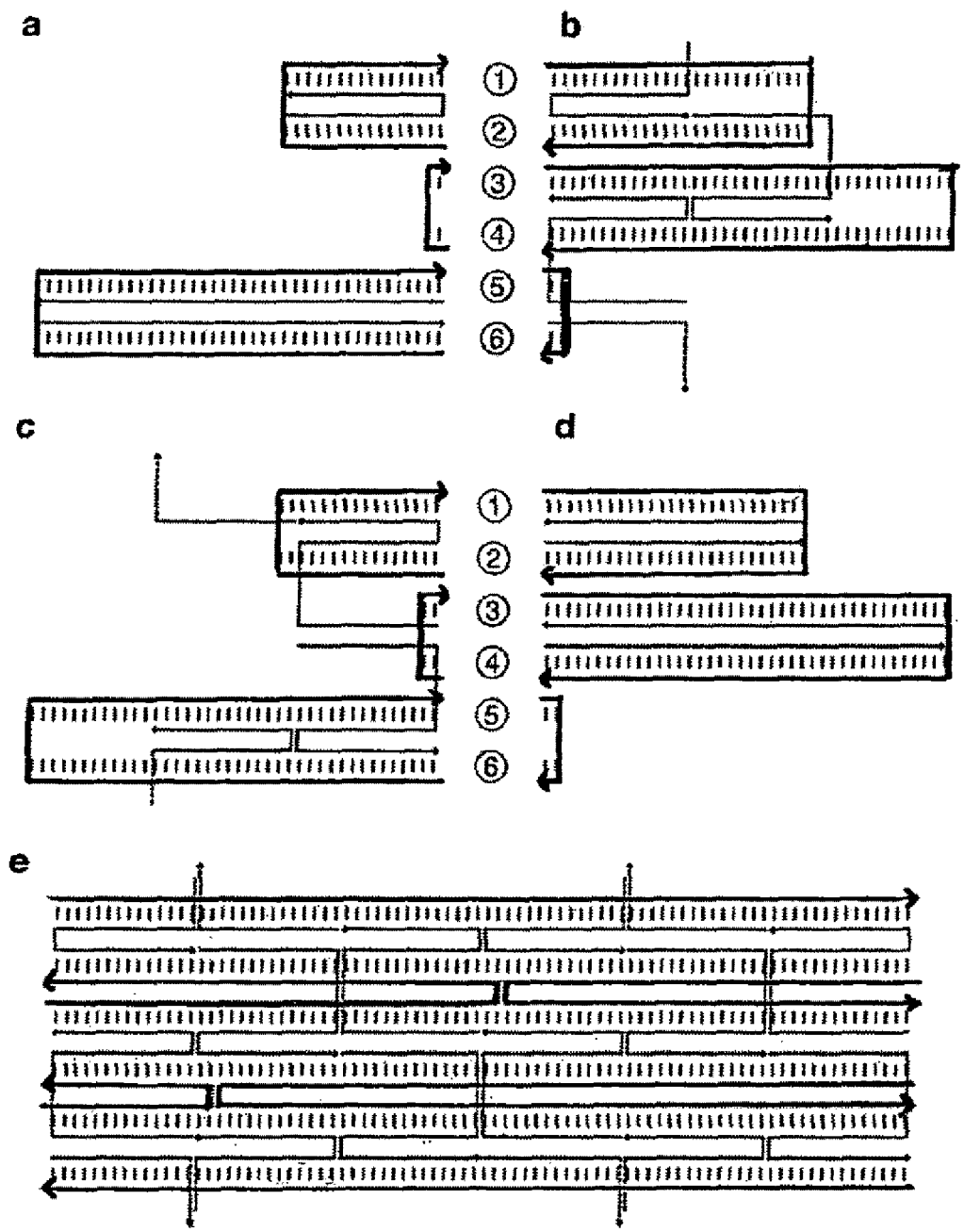
FIG. 3 shows schematic representations of the front and rear overhangs of the pre-dimerization monomers that combine to form DNA heterodimer nanotubes

Dimerization of the DNA nanotubes can be achieved, for example, as shown in 3. FIG. 3 shows schematic views of the pre-dimerization monomers that can combine to form heterodimer DNA nanotubes. Specifically, FIGS. 3a-3d show the scaffold-plus-staples schematic views of the front and rear overhangs of the monomers. One strand of each double helix can be contributed by the scaffold (darker lines in FIGS. 3a-3e), and the other strand can be contributed by a staple oligonucleotide. Base pairs in the Figure are depicted as short vertical lines between the paired strands. Helices 1-6 are labeled in the center of FIGS. 3a-b and 3c-d. FIG. 3a shows the front monomer head segment. Three staple strands can serve to cap the front monomer head (see DNA sequences, FIG. 8). FIG. 3b shows the front monomer tail segment, which has three staple strands (see DNA sequences, FIG. 9) with a total of 26 unpaired bases decorating the tail (2 bases in helix 2, 12 bases each in helices 5 and 6). The scaffold strand in this region is unpaired for 36 bases (12 bases each in helix 1, 3, and 4). FIG. 3c shows the rear monomer head segment. Three staple strands (see DNA sequences, FIG. 10) on this portion of the monomer have a total of 36 unpaired bases decorating the head. These unpaired regions are complementary to the corresponding 36 unpaired bases of the front monomer tail scaffold strand. The 26 unpaired bases in the rear monomer head scaffold strand can be complementary to the 26 unpaired bases of the three staple strands that decorate the front monomer tail. In the DNA nanotube heterodimer, these unpaired regions can match up to form the complete intermonomer junction, as shown in FIG. 3e. FIG. 3d shows the rear monomer tail segment. Four staple strands can serve to cap the rear monomer tail (see DNA sequences, FIG. 11). FIG. 3e shows the junction between the head and tail monomers forming the assembled heterodimer. The scaffold crossovers (darker vertical lines) that form an internal seam for each monomer occur at segments 14 and 15, as shown in FIGS. 1b and c.

In the nucleic acid nanotubes of the inventions, the scaffold strand is arranged with base pair sequences optimized to avoid unintended binding events between staple strands and the scaffold strand, or between different sections of the scaffold strand. The scaffold strand can be derived from a natural source whose base pair sequences have been completely characterized. In one embodiment, the scaffold strand is derived from the M13 mp 18 viral genome, which is well-characterized and relatively inexpensive to generate in large quantities. It is also amenable to recombinant approaches to insert or delete sequences. The scaffold strand can also be an entirely artificial sequence, a modified natural sequence, or any combination of natural and artificial sequences.

In another embodiment, plasmids based on the pBluescript vector can be used where a shorter, exact number of bases is desired. This avoids having extra unscaffolded material that may interfere with folding of the scaffold. With pBluescript, there is more flexibility with inserting DNA's that are many kilobases in size, without concern about plasmid instability. To facilitate the excision of a single-strand DNA target insert from the generic vector, inverted repeat restriction sites can be introduced into the vector. Inverted repeat EcoR I sites separated by 20 base pairs can be added upstream of the target sequence. Inverted repeat Hind III sites separated by 20 base pairs can also be added downstream of the target sequence. In the single-stranded DNA, the repeated sites fold up to form double-stranded sites that are recognizable by the appropriate restriction enzyme.

Assembly of the Nanotubes

The nucleic acid nanotubes of the present invention are self assembling. The scaffold strand and a molar excess of staple oligonucleotides are added to a desired buffer, which preferably contains $MgCl_2$. The solution is heated to a temperature sufficient to denature all the nucleic acids contained therein (e.g., 90° C.), and then slowly allowed to cool. The step of cooling should be such that the solution returns to a temperature, e.g., room temperature, which permits assembly of the nanotubes over approximately 1 hour to 24 hours, e.g., over 2 hours or 20 hours.

Example 1

Preparation of DNA Nanotubes

M13 single stranded scaffold DNA (sequence shown in FIGS. 12A-C) was obtained from phage produced from infected F+bacteria grown in 2×YT media. Purified single-stranded DNA was extracted from the phage using a Qiagen Gigaprep ion-exchange column. Six-helix bundle DNA nanotubes were folded directly from the eluate of a Qiagen Gigaprep ion-exchange column, eluted at 50 mM Tris pH 8.5 (Fisher Scientific), 1.6 M NaCl (Fisher Scientific), 15% isopropanol. In the folding reaction, the buffer was diluted to 1 M NaCl, 9% isopropanol, along with 50 nM of the organic chemical buffer HEPES (4-2-hydroxyethyl-1-piperazineethanesulfonic acid) pH 7.5 (Sigma), 10 mM $MgCl_2$ (Fisher Scientific). The scaffold concentration was at 6 nanomolar and the staple oligonucleotide (sequences shown in FIG. 13A-D) concentrations were at 36 nM each. The isopropanol did not interfere with the folding. Folding was performed by heating the suspension in 100 mL Pyrex bottles in 2 L boiling water baths to 90° C., then covering the lid and allowing to cool to room temperature over the course of 20 hours.

The folded six-helix bundle DNA nanotubes thus formed were separated from the excess oligonucleotides by precipitation with 40% ethanol. The DNA nanotubes survived desalting with a 75% ethanol wash followed by dehydration in a speedvac. After drying, the DNA nanotubes were resuspended in a desired volume of buffer, without evidence of aggregation or other misfolding.

Example 2

Recombinant M13 Bacteriophage Plasmid (p7308) Construction

Recombinant M13 filamentous bacteriophage was prepared by replacement of the BamHI-XbaI segment of M13 mp18 by a polymerase chain reaction-generated 59 base pair (bp) fragment encoding a randomly-selected sequence (FIG. 14), flanked by positions −25 to +25 of the middle of the XbaI cut site (T^CTAGA, or base 6258). A list of oligodeoxyribonucleotides that were used to construct the insert with flanking regions (109 by total) is shown in FIG. 15. Double-stranded (replicative form) bacteriophage M13 DNA bearing the 59 base insert was prepared as described in Sambrook, J. & Russell, D. *Molecular cloning: A Laboratory Manual* (Cold Spring Harbor Laboratory Press, Cold Spring Harbor, 2001). The 59.bp insert was verified by a double restriction digest with BainHI and XbaI, followed by sequencing. The result was a modified bacteriophage M13 genome, 7308 bases in length. The full sequence is shown in FIG. 16.

Example 3

Nanomole-Scale Production of M13 Bacteriophage Single-Stranded DNA

Recombinant M13 bacteriophage RF dsDNA was transformed into JM101 cells and grown overnight at 37° C. on an LB-agar plate (BD Diagnostics). A single, well-isolated plaque was used to inoculate 2 ml of 2×YT medium in a 14 mL sterile culture tube and agitated for 8 hours at 37° C. Bacterial cells were pelleted by centrifugation and phage was recovered from the supernatant by polyethylene glycol fractionation (incubation on ice for 30 minutes using a final concentration of 4% PEG8000, 0.5 M NaCl) followed by centrifugation. The phage was resuspended in 1000, of 10 mM Tris.Cl pH 8.5 (Fisher Scientific) and labelled "pre-inoculation phage." *E Coli* JM109 cells were grown overnight in 3 mL of 2×YT medium at 37° C. The 3 mL of JM109 culture was added to a 2 L flask containing 300 mL 2×YT medium supplemented with $MgCl_2$ to 5 mM final concentration and incubated at 37° C. on a shaker at 300 rpm. When the bacterial culture reached $A_{600}$=0.5, 50 μL of the "pre-inoculation phage" stock was added. The infected culture was grown at 37° C., shaking at 300 rpm for an additional 4 hours. Phage was recovered as described above, and resuspended in 3 mL 10 mM Tris.Cl pH 8.5 and labelled "inoculation phage." Titer of "inoculation phage" was measured by plating out serial dilutions using saturated JM109 culture and LB-top agar plates. Titer of JM109 cells at A600=0.5 was measured by plating out serial dilutions on LB-agar plates. For nanomole-scale production of phage, twelve 2 L flasks each containing 300 mL 2×YT medium supplemented with 5 mM $MgCl_2$, were inoculated with 3 mL overnight JM109 culture and incubated at 37° C. shaking at 300 rpm. When density reached $A_{600}$=0.5, each flask was infected with "inoculation phage" at an MOI=1. Phage was harvested as described, and resuspended in 0.5% of the original culture volume in 10 mM Tris.Cl pH 8.5. Single-stranded DNA was isolated from phage by alkaline/detergent denaturation as follows: Two volumes of lysis buffer (0.2 M NaOH, 1% SDS) were added to the resuspended phage, followed by 1.5 volumes neutralization buffer (3 M KOAc pH 5.5). Lysed phage was centrifuged for 10 minutes at 16000 ref. The supernatant was combined with one volume of 200 proof ethanol and centrifuged for 10 minutes at 16000 ref. Pelleted ssDNA was washed twice with 75% ethanol, centrifuged, and resuspended in 5% of the original culture volume in 10 mM Tris.Cl pH 8.5. The concentration of the recovered ssDNA was estimated on a UV/visible spectrophotometer (Beckman coulter) using an extinction coefficient=37.5 μg/mL for $A_{260}$=1.

Example 4

Preparation of 800 Nm DNA Nanotube Heterodimers

A detergent-resistant liquid crystal of 0.8 μm-long DNA nanotubes has been designed and constructed, and has been shown to induce weak alignment of membrane proteins. The nanotubes are heterodimers of 0.4-μm-long six-helix bundles each self-assembled from a 7.3-kilobase scaffold strand and over 170 short oligonucleotide staple strands. Desalted DNA oligonucleotides, normalized by concentrations to 150 μM, were purchased from Invitrogen (see DNA sequences of FIGS. 8-11, 17, 18). Equal volumes of each staple oligonucleotide were pooled into groups: front monomer staple stock (DNA sequences of FIGS. 8, 9, 17) and rear monomer staple stock (DNA sequences of FIG. 10, 11, 18). The front monomer staple stock includes front head cap staples (DNA sequences of FIG. 8), front core staples (DNA sequences of FIG. 17), and front tail connector staples (DNA sequences of FIG. 9). The rear monomer staple stock includes rear head connector staples (DNA sequences of FIG. 10), rear core staples (DNA sequences of FIG. 18), and rear tail cap staples (DNA sequences of FIG. 11). Concentrations of the pooled staple stocks were estimated on a UV/visible spectrophotometer using an extinction coefficient=33 μg/mL for $A_{260}$=1.

Front and rear monomers were prepared with their respective staple stocks, but otherwise using an identical protocol. The front monomer folding mixture was prepared by combining p7308 ssDNA (30 nM), front monomer staple stock (300 nM each staple strand), 50 mM HEPES pH 7.5, 50 mM NaCl, and 30 mM $MgCl_2$ in a final volume of 76.8 mL. The folding mixture was aliquoted into four 96-well plates (Molecular BioProducts) (200 μl, per well), and folded on a thermal cycler (MJ Research Tetrad) with the following program:

1. 80° C. for 5:00
2. 80° C. for 2:00 (−1° C. per cycle)
3. Go to 2, 60 times
4. End Folded material was pooled into a 250 mL polypropylene centrifuge bottle. Folded nanotubes were separated from excess staple strands via PEG fractionation as follows: 19.2 mL of 20% PEG8000 (Fisher Scientific), 2.5 M NaCl was added to mixture, which was then centrifuged at 15000 rcf for 15 minutes. The supernatant was discarded, and the nanotube pellet was resuspended in 38.4 mL 50 mM HEPES pH 7.5, 50 mM NaCl, and 30 mM $MgCl_2$. A second PEG fractionation was carried out as follows: 9.6 mL of 20% PEG8000, 2.5 M NaCl was added to mixture, which was then centrifuged at 15000 rcf for 15 minutes. The supernatant was discarded, and the nanotube pellet was resuspended in 38.4 mL 50 mM HEPES pH 7.5, 50 mM NaCl, and 30 mM $MgCl_2$.

Nanotube heterodimers were formed by combining front and rear monomer mixtures together and incubating at 37° C. for 2 hours. Two volumes of equilibration buffer (750 mM NaCl, 50 mM MOPS, pH 7.0, 15% isopropanol, 0.15% Triton X-100 (v/v)) were added to the mixture. Heterodimers were loaded on a Qiagen-Tip 10000 gravity-flow ion-exchange column equilibrated with 75 mL equilibration buffer. The column was washed with six 100 mL volumes of 1 M NaCl, 50 mM MOPS, pH 7.0, 15% isopropanol (v/v). Then the nanotubes were precipitated by addition of one volume 200 proof ethanol, centrifuged at 15000 rcf for 15 minutes, washed twice with 75% ethanol, and resuspended in 3 mL 1 mM $NaH_2PO_4$ pH 7.0, 1 mM $MgCl_2$. The nanotube concentration was estimated via UV absorbance at 260 nM assuming an extinction coefficient of $A_{260}$=1 for 50 μg/ml. The nanotube heterodimer mixture was then concentrated by Speedvac vacuum centrifugation to a final volume of 3004. Front and rear monomers were folded in separate chambers via heat denaturation followed by cooling for renaturation.

The front and rear monomers were mixed to self-assemble heterodimers (FIGS. 1*a-c*, and 1*e*). The joining of the tail of the front monomer to the head of the rear monomer should generate a 42-base-pair pseudo-repeat segment (FIG. 1e). In this segment, all six staple strands bridge the two scaffolds, although by varying numbers of base pairs. In total, a net 62 base pairs must be broken to sever the linkage between successfully heterodimerized monomers.

Example 5

Demonstration of the Liquid Crystallinity of DNA Nanotubes

Six helix bundle DNA nanotubes from Example 1 were incubated in 25% ethanol, causing selective precipitation of the nanotubes, and leaving behind the excess unbound staple oligonucleotides. Nine milligrams of the DNA nanotubes were resuspended in a volume of 6 mL 2.5 mM HEPES pH 7.5, 2.5 mM NaCl, 0.5 mM $MgCl_2$, and then dehydrated in a Savant speedvac concentration system to achieve a final concentration of 30 mg/ml (300 μL of a 3% suspension) and final buffer concentrations of 50 mM HEPES pH 7.5, 50 mM NaCl, and 10 mM $MgCl_2$.

Figure 19:
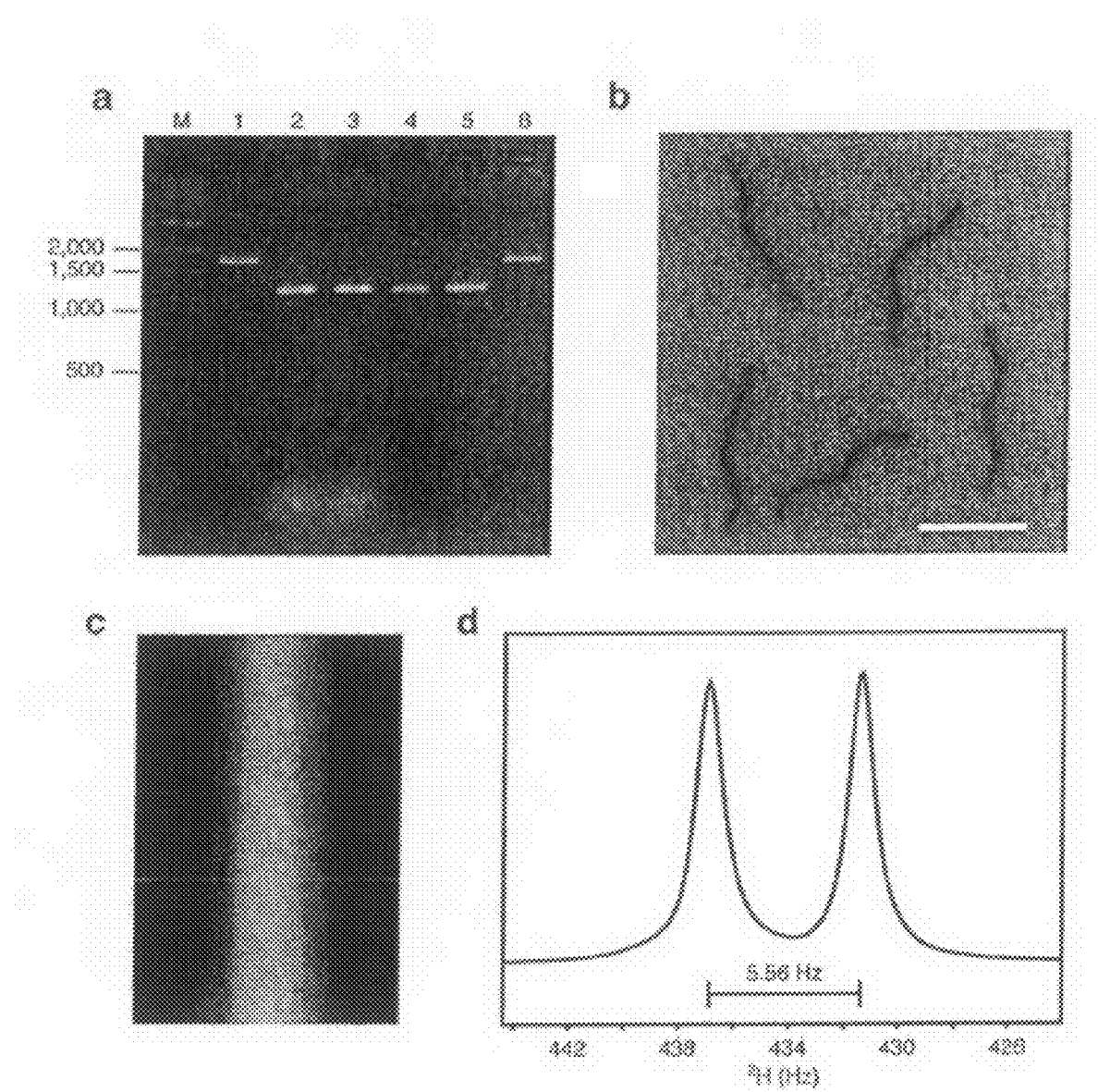
FIG. 19a shows a gel-shift analysis of folding and heterodimerization of DNA nanotubes.
FIG. 19b shows a negative-stain electron micrograph of DNA nanotube heterodimers.
FIG. 19c shows a photograph of the birefringence exhibited between crossed polarizers by DNA nanotube dimmers at 28 mg/mL in a glass NMR tube.
FIG. 19d shows the NMR spectrum of a 90% $H_2O$/10% $D_2O$ sample containing 28 mg/mL DNA nanotube heterodimers.

The liquid crystallinity of the DNA nanotube suspension in an NMR tube was verified by observation of birefringence under crossed polarizers. A low-salt, aqueous suspension of DNA-nanotube heterodimers at a concentration of 28 mg $mL^{-1}$ forms a stable liquid crystal, as indicated by strong birefringence observed through crossed polarizers, as shown in FIG. 19c. (FIG. 19c). The liquid crystals were diluted by 10% with deuterated water, and were aligned for three hours in a 600 MHz NMR spectrometer. Strong birefringence was observed when the sample tube was placed at 45 degrees to the crossed polarizers.

Figure 20:
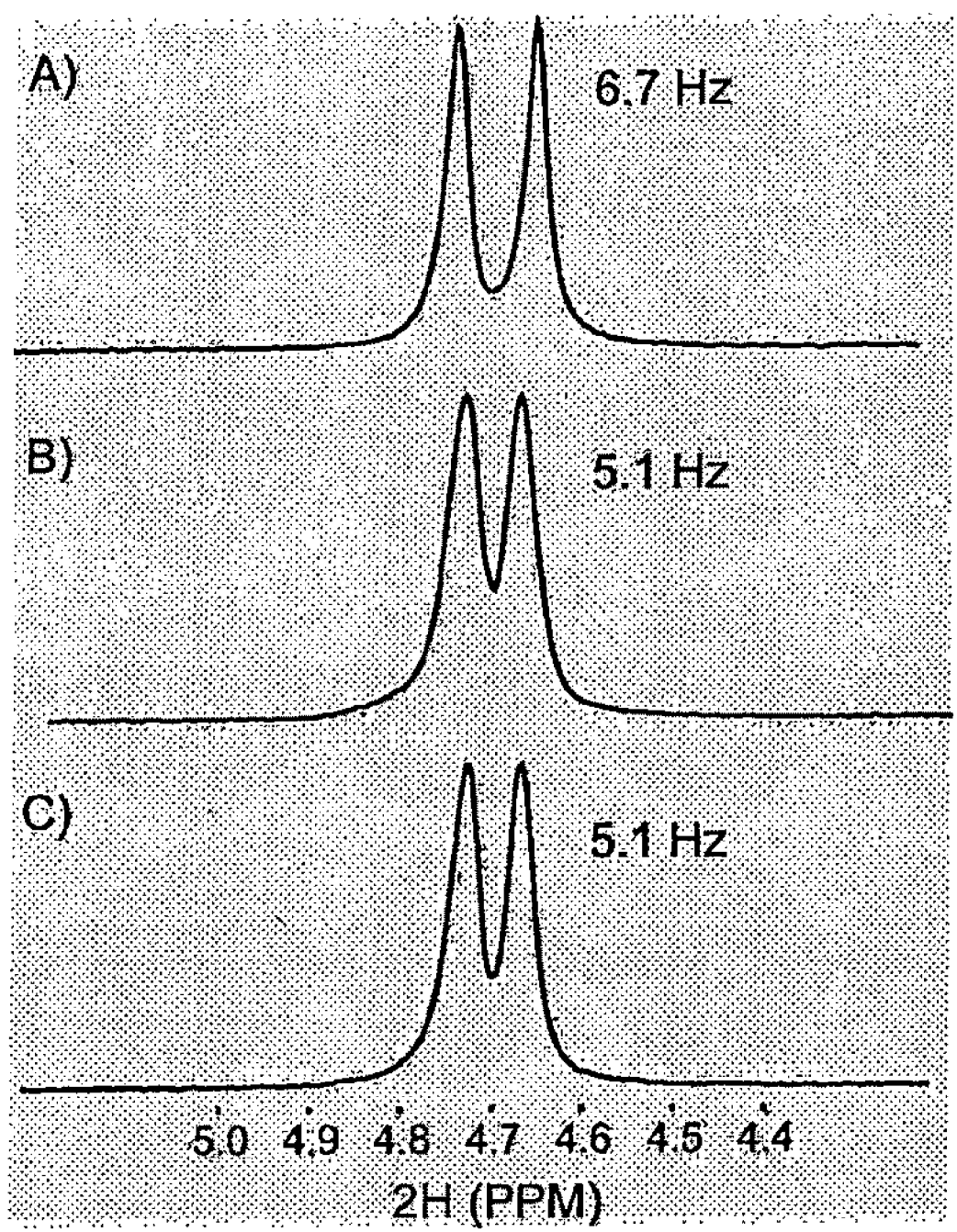
FIG. 20 shows the $^2H$ NMR spectra of $D_2O$ in liquid crystalline DNA nanotubes recorded at 30 degrees C. and $^1H$ frequency of 500 MHz. In panel (A), the $^2H$ quadrupolar coupling constant was 6.7 Hz for liquid-crystalline DNA nanotube at a concentration of 30 mg/ml in 50 mM HEPES, 50 mM NaCl, 10 mM $MgCl_2$, pH 7.5. In panel (B), 100 mM LMPG detergent was added, yielding a coupling constant of 5.1 Hz (consistent with mere dilution of the $D_2O$). Panel (C) shows that no change in the coupling constant was observed 24 hours after addition of the detergent.

Further evidence for liquid crystallinity of the DNA nanotube monomers was obtained by NMR spectroscopy, measuring quadrupolar splitting of the deuterium, where a coupling constant of 6.7 Hz was observed (FIG. 20A). Next, 1-myristoyl-2-hydroxy-sn-glycero-3-[phospho-RAC-(1-glycerol)] (LMPG) detergent was added to 100 mM. After addition of the detergent, the coupling constant dropped to 5.1 Hz, which is consistent with the 16% dilution of $D_2O$ in the sample upon addition of the detergent suspension. The liquid crystals remain stable over at least 24 hours in the presence of the detergent (FIG. 20C).

When the suspension of 800 nanometer heterodimers is aligned in an 11.4 Tesla magnetic field in the presence of 10% $D_2O$, the weakly-oriented HDO yields $^2H$ quadrupolar splitting of 5.56 Hz (FIG. 19d). The 1D $^2H$ spectrum shown in FIG. 19d was obtained from a 10 mM $NaH_2PO_4$, 10 mM $MgCl_2$, 90% $H_2O$/10% $D_2O$ sample containing 28 mg/mL DNA nanotube heterodimers. NMR spectra were processed and analyzed using NMRPipe. Fitting of the dipolar couplings to the known ζ-ζ homodimer structure was done by singular value decomposition (SVD), using the program PALES. The goodness of fit was assessed by both Pearson correlation coefficient (r) and the quality factor (Q).

Example 6

Characterization of DNA Nanotubes

Figure 21A:
FIG. 21a shows native agarose gel electrophoresis. I, 1 kb ladder; II, naked 7308 base scaffold; III, folded DNA nanotube.

Folded DNA nanotubes were analyzed using agarose gel electrophoresis and negative-stain electron microscopy using uranyl formate (Pfaltz & Bauer) as the stain. Gel electrophoresis experiments indicated that the majority of scaffold molecules are folded as monomers, as they produced a single band upon agarose gel electrophoresis in the presence of 10 mM $MgCl_2$ (FIG. 21a). Further analysis of folding and heterodimerization of DNA nanotubes was conducted via electrophoresis in a 2% agarose gel containing 11 mM $MgCl_2$, 0.5 μG/mL ethidium bromide, 45 mM Tris base, 45 mM boric acid, and 1 mM EDTA (pH 8.0), and is shown in FIG. 19a. The majority of DNA objects migrate as a single band in agarose-gel electrophoresis (FIG. 19a). This population presumably represents well-formed nanotube monomers, while slower migrating species apparent on the gel presumably represent misfolded or multimerized structures. Lane M is the marker lane with DNA size standards denoted by number of base pairs shown to the left of the lane. Lane 1 shows the M13-derived single-stranded DNA scaffold. Lanes 2 and 3 show the front and rear DNA monomers (including scaffold plus staples). Lanes 4 and 5 show the front and rear monomers after PEG fractionation. Agarose-gel electrophoresis of heterodimers assembled from the two monomers indicates that the majority of DNA objects migrate as a single band (FIG. 19a, Lane 6), although some misfolded objects are evident, as are a small population of monomeric nanotubes. Lane 6 shows the heterodimers after a two-hour incubation of mixed monomers at 37° C.

Figure 21B:
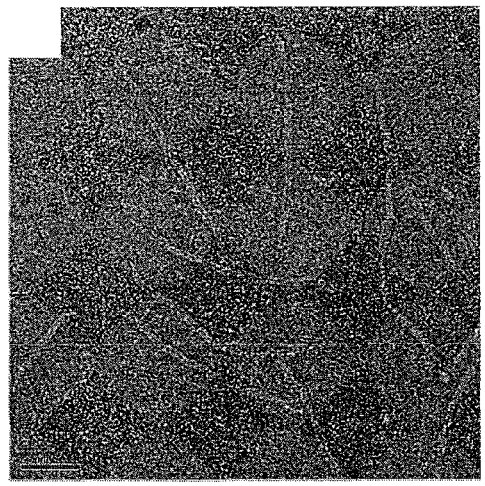
FIG. 21b shows negative-stain electron micrograph of 200 nm DNA nanotube; scale bar is 50 nm.
Figure 21C:
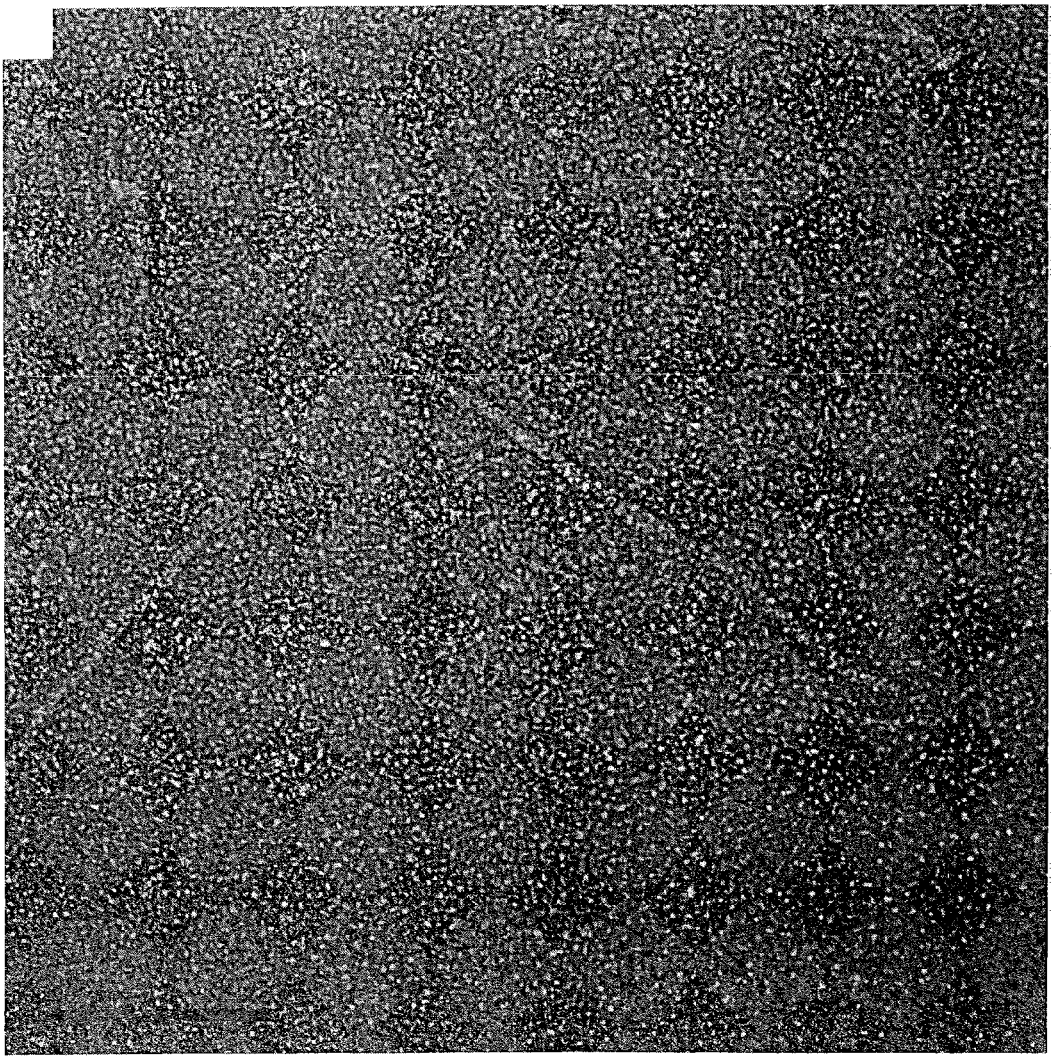
FIG. 21c show negative-stain electron micrograph of 400 nm DNA nanotube, scale bar is 200 nm.
Figure 22A:
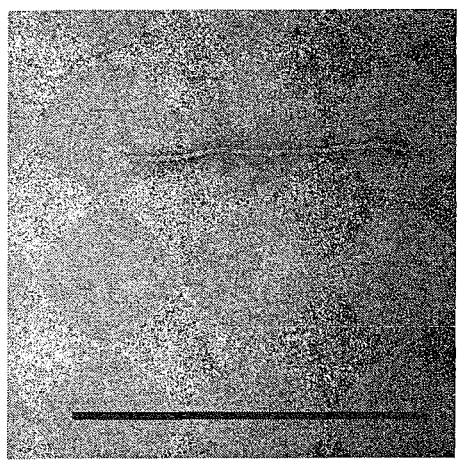
FIG. 22a shows a DNA front monomer at 68000× magnification.
Figure 22B:
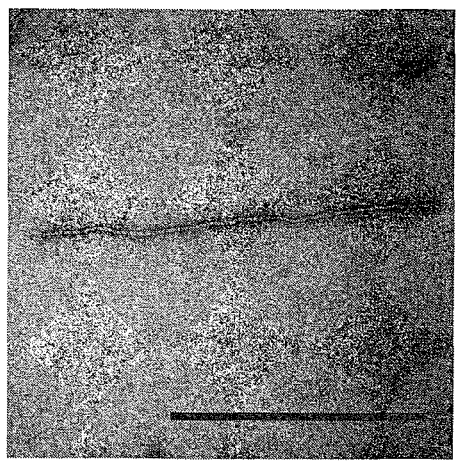
FIG. 22b shows a DNA nanotube heterodimer at 49000× magnification.
Figure 22C:
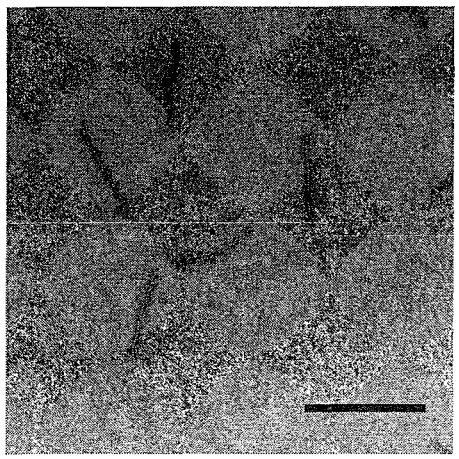
FIG. 22c shows DNA nanotube front monomers at 23000× magnification.
Figure 22D:
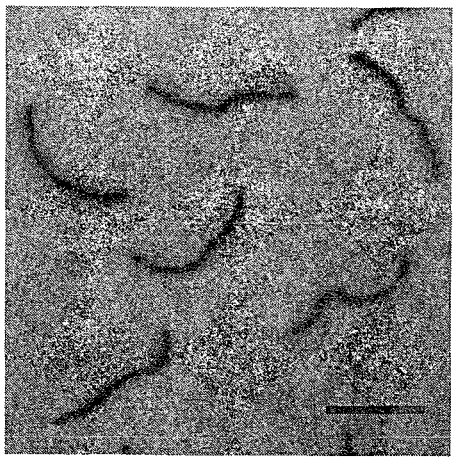
FIG. 22d shows DNA nanotube heterodimers at 18500× magnification.
Figure 22E:
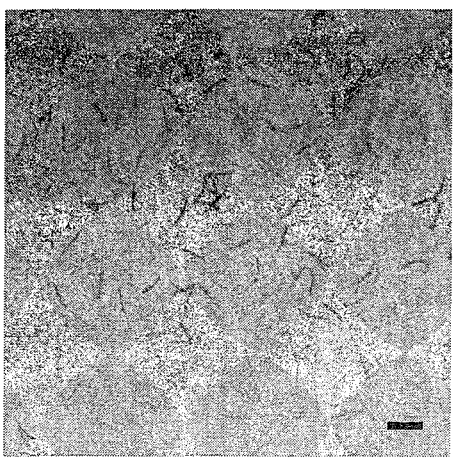
FIG. 22e shows DNA nanotube front monomers at 6800× magnification.
Figure 22F:
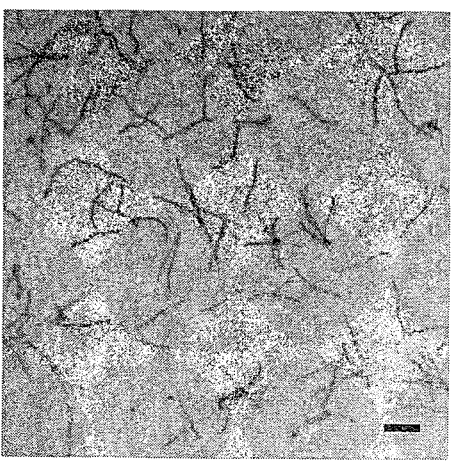
FIG. 22f shows DNA nanotube heterodimers at 6800× magnification.

Electron micrograph analysis was carried out using Image SXM. The lengths of 20 well-isolated DNA nanotube monomers and 20 well-isolated DNA nanotube dimers in several separate electron micrographs were measured manually using the segmented-line tool. Following the dimerization step, DNA nanotube dimers were diluted to 1 nM concentration and prepared for imaging by negative stain with 0.7% uranyl formate (Pfaltz & Bauer) as previously described. (Ohi, M., Cheng, Y., Walz, T. *Biol. Proc. Online* 6, 23-24 (2004)). Gilder Fine BarGrids, 400 mesh, 3.05 mm O.D. (Ted Pella) were used. Imaging was performed on a Tecnai $G^2$ Spirit BioTWIN. Electron microscopy experiments (FIG. 21b, 21c) showed that the DNA nanotubes are much more rigid than double helices. If double helices are assumed to be 2 nm wide and 0.34 nm per basepair, then the predicted width would be 6 nm, and the predicted length would be either 200 nm or 414 nm. The length and width of the imaged objects approximately matched the predicted dimensions. The DNA nanotube heterodimer mixture was also analyzed using negative-stain electron microscopy, and the results are consistent with a large fraction of intact nanotubes of length 402±6 nanometers (Figures S2, a, c, and e). This measured length is in good agreement with the predicted length of 400 nanometres for 28 segments that are 42 base pairs long, assuming a rise of 0.34 nanometers per base pair. Negative-stain electron microscopy also revealed nanotubes of length 813±9 nanometers, as shown in FIG. 19b (scale bar=500 nanometers) and Figures S2, b, d, and f). This measured length agrees well with the predicted length of 814 nanometers for 57 segments that are 42 base pairs long.

Example 7

Solution NMR Methodology for Membrane-Protein Structural Determination

Membrane proteins play important roles in cell biology and medicine. For example, over half of hormones and neurotransmitters studied to date transduce signals through members of the G-Protein Coupled Receptor (GPCR) family of membrane proteins. Similarly, over half of all commercial drugs target GPCR's. Despite their importance, structures of only ~100 membranes proteins have been solved to date blanco.biomol.uci.edu/Membrane_Proteins_xtal.html holds a tally that is updated regularly). The slow rate of membrane-protein structure determination represents a significant bottleneck for both basic and applied bioscience discovery. This bottleneck largely derives from difficulties in forming well-ordered three-dimensional crystals of membrane proteins (Caffey M, Membrane protein crystallization, J. Struct. Biol. 142, 108-132, 2003). Solution NMR presents a potentially-attractive alternative for the study of many membrane proteins, as high-resolution structural information can be obtained for systems up to 80 kD in size without the need for crystallization.

Solution NMR has advanced to the point where structure determination of 30-kD water-soluble proteins has become routine. This has not been the case, however, for membrane proteins. For solution NMR, macromolecules must be solubilized in water to facilitate fast tumbling; the faster the tumbling, the better the spectra. To promote water solubility, membrane proteins must be complexed with detergent micelles. The micelle-protein complex is considerably larger than the protein alone, and tumbling is relatively slow as a result. This increase in effective size is especially problematic for a-helical membrane proteins greater than 15 kDa in size, where resonance peaks are closely spaced and become unresolvable with the fast coherence relaxation of the slowly-tumbling macromolecules. Some of the larger alpha-helical membrane proteins whose structures has been solved by solution NMR include the Mistic membrane-surface-associating protein (13 kDa) (Roosild T P, Greenwald J, Vega M, Castronovo S, Riek R, Choe S, NMR structure of Mistic, a membrane-integrating protein for membrane protein expression, Science 307, 1317-1321, 2005) and subunit c of the ATP synthase (7 kDa) (Girvin M E, Rastogi V K, Abildgaard F, Markley J L, Fillingame R H, Solution structure of the transmembrane H+-transporting subunit c of the FIFO ATP synthase, Biochemistry 37, 8817-8824, 1998). Recently, our collaborators in Dr. Chou's laboratory have used solution NMR for the de novo structure determination of the phospholamban pentamer, a 30-kD channel-like protein that spans the sarcoplasmic reticulum membrane (Oxenoid K, Chou J J, The structure of phospholamban pentamer reveals a channel-like architecture in membranes, Proc Nat'l Acad Sci USA 102, 10870-10875, 2005). In that case, however, the NMR spectra were simplified because of the five-fold rotational symmetry in the complex.

For conventional NMR spectroscopy, the Nuclear Overhauser Effect (NOE) provides the only experimentally-measurable distance restraint for tertiary structure determination. Successful structure determination requires the correct assignment of most of the proton resonances, a demand that can be almost impossible to meet for poorly-resolved spectra such as those recorded for a-helical membrane proteins. Furthermore, NOE's only are detectable for distances shorter than five angstroms, thus determination of the global shape of extended proteins is subject to compounded errors.

RDC's encode global orientational constraints that enable structure determination with only limited NOE assignments required. If a large number of accurate RDC's can be measured, then a full analysis of the NOESY spectra—which may in practice be unobtainable—becomes unnecessary. In this case, it will be sufficient to measure NOE's after selective labeling of amino acids, which simplifies the spectrum, or to measure semi-quantitative distance constraints from paramagnetic-broadening techniques.

Residual dipolar coupling leads to informative resonance frequency splitting. In the presence of an external field B that points in the z-direction, the z-component of the magnetic field from nucleus S will change the magnetic field at I such that the resonance frequency of I will shift by a quantity that depends on the internuclear distance and on the internuclear angle with respect to the z-axis. If the protein is undergoing rapid isotropic tumbling, then the average perturbation averages to zero.

In order to obtain information about the internuclear angles, then, each protein must be made to tumble in a weakly-ordered regime. Too much ordering and dipolar couplings become so strong that peaks are unresolvable, while too little ordering leads to undetectable levels of dipolar coupling. The appropriate weak ordering, about 0.1%, can be achieved by dissolving the protein in the right concentration of a suitable alignment material. For example, water-soluble proteins can be aligned weakly by the required amount with ~1.5-2% Pfl filamentous phage, which forms a liquid crystal at that concentration.

Membrane proteins can be weakly aligned. The easiest method for weak-alignment of proteins is through mixing the protein with a liquid-crystalline medium, such as Pfl filamentous phage, DMPC/DHPC bicelles, C12E5 polyethylene glycol, or cellulose crystallites. However, none of these media are compatible with detergent-solubilized membrane proteins. The only method currently available for weak alignment of membrane proteins involves the use of radially-compressed polyacrylamide gels (Oxenoid K, Chou J J, The structure of phospholamban pentamer reveals a channel-like architecture in membranes, Proc Nat'l Acad Sci USA 102, 10870-10875, 2005; Chou J J, Gaemers S, Howder B, Louis J M, Bax A, A simple apparatus for generating stretched polyacrylamide gels, yielding uniform alignment of proteins and detergent micelles, J Biomol NMR 21, 377-382, 2001; Chou J J, Kaufman J D, Stahl S J, Wingfield P T, Bax A, Micelle-induced curvature in a water-insoluble HIV-1 Env peptide revealed by NMR dipolar coupling measurement in stretched polyacrylamide gel, J Am Chem. Soc 20, 2450-2451, 2002; Tycko R, Solid-state NMR as a probe of amyloid fibril structure, Curr Opin Chem. Biol 4, 500-506, 2000). A technical problem encountered during the weak alignment of phospholamban was that the maximum protein concentration obtainable in the gel was ~0.2 mM, despite soaking in a solution with a protein concentration of 1-2 mM. Because of the low concentration, the signal-to-noise ratio of the NMR signals was low. Long data acquisition times were required, and the resultant RDC measurements were of limited accuracy. The difficulty in soaking detergent-solubilized membrane proteins into polyacrylamide gels is a well-known problem in the NMR community.

The six-helix bundle DNA nanotubes described herein represent a detergent-resistant shape mimetic of the Pfl filamentous phage. These DNA nanotubes have similar liquid-crystalline behavior as Pfl, but are completely resistant to strong detergents such as SDS.

Example 8

Use of DNA Nanotube Liquid Crystal to Measure Backbone RDC's for the Transmembrane Domain of the T-Cell Receptor All NMR experiments were performed on Bruker spectrometers equipped with cryogenic TXI probes at 30° C. The RDC's were obtained from subtracting J or J+D couplings of the aligned sample from that of unaligned sample. The $^{1}H$-$^{15}N$ RDC's were obtained from $^{1}J_{NH}/2$ and $(1J_{NH}+^{1}D_{NH})/2$, which were measured at 600 MHz (1H frequency) by interleaving a regular gradient-enhanced HSQC and a gradient-selected TROSY, both acquired with 80 ms of $^{15}N$ evolution. The $^{15}H_{\alpha}$-$^{13}C_{\alpha}$ RDC's ($1D_{C\alpha H\alpha}$) were measured at 500 MHz (1H frequency) using a 2D CACONH quantitative $^1J_{C\alpha H\alpha}$ experiment with interleaved spectra recorded at $^1J_{C\alpha H\alpha}$ modulation times of 1.83, 3.63, and 7.12 ms. This experiment was modified from the 3D CBCACONH quantitative $J_{CH}$ experiment[30] used primarily for measuring protein side-chain $^1H_\beta$-$^{13}C_\beta$ RDC's. The CACONH was optimized for measuring the backbone $^1H_\alpha$-$^{13}C_\alpha$ RDC's only. Since the ζ-ζ transmembrane (TM) domain is a homodimer obeying two-fold rotational symmetry, the same RDC's are assigned to both subunits. The frequency labeled dimensions in this experiment are $^1H^N$ (direct) and $^{15}N$ (indirect).

Figure 23:
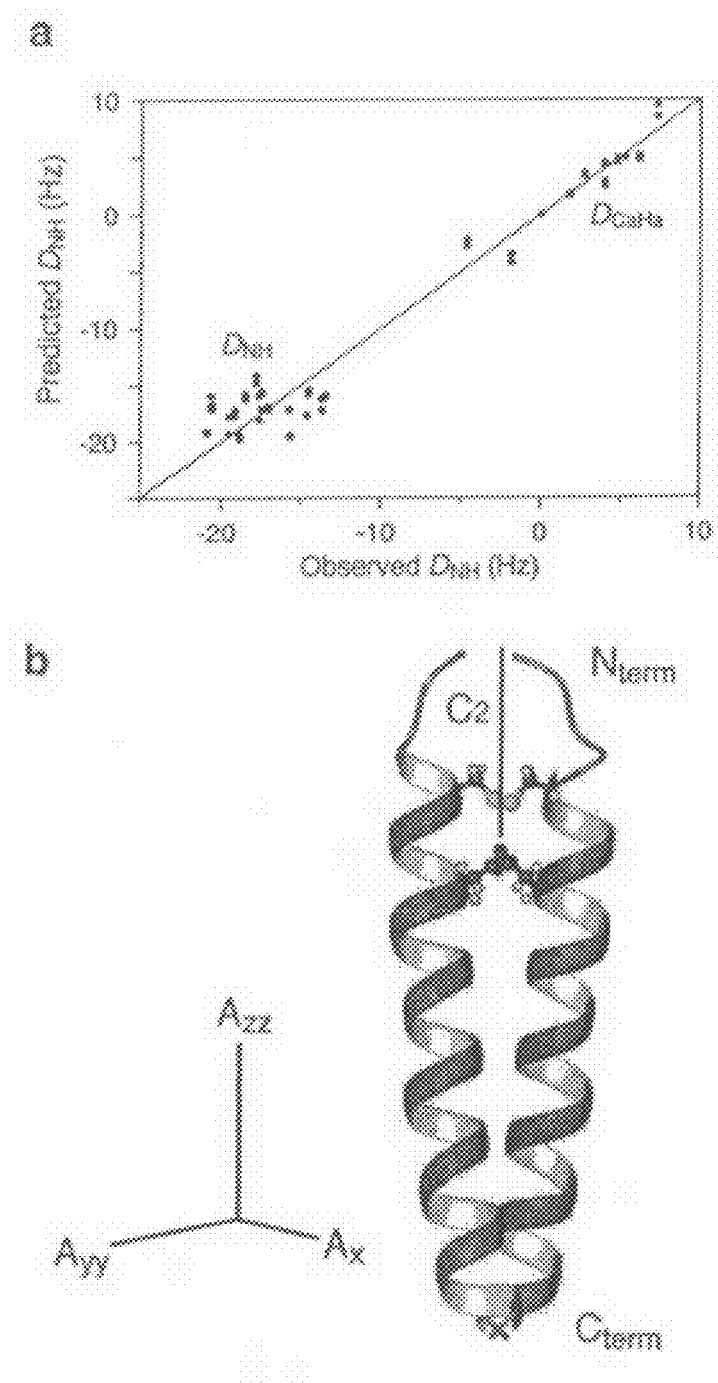
FIG. 23a shows an analysis of the residual dipolar couplings (RDC's) measured for the detergent-reconstituted transmembrane domain of the ζ chain of the T-cell receptor complex, weakly aligned in a 28 mg/mL DNA nanotube mixture. Shown is a 0.98 correlation coefficient between the observed backbone RDC's and the RDC's predicted for the known NMR structure of the ζ-ζ transmembrane domain (2HAC) obtained from the Protein Data Bank.
FIG. 23b shows the principal axes of the alignment tensor relative to 2HAC, the ζ-ζ dimer of the T cell receptor.

The DNA-nanotube liquid crystal enables the accurate measurement of backbone $N_H$ and $C_\alpha H_\alpha$ RDC's for the detergent-reconstituted ζ-ζ transmembrane domain of the T-cell receptor. The measured RDC's validate the high-resolution structure of this transmembrane dimer. The DNA heterodimer nanotubes were tested for weak alignment of the transmembrane (TM) domain (residue 7-39) of the ζ-ζ chain of the T-cell receptor complex reconstituted in mixed dodecylphosphocholine (DPC)/sodium dodecyl sulfate (SDS) detergent micelles. The measured $^1$H-15N and $^1H_\alpha$-$^{13}C_\alpha$ RDC's agree very well with the known NMR structure of the ζ-ζ TM domain, with a correlation coefficient of the Singular Value Decomposition (SVD) fit, $R_{SVD}$, of 0.98, or a free quality factor, $Q_{free}$ 16% (FIG. 23a). The magnitude of the alignment tensor, $D_a$, is −9.9 Hz (normalized to $D_{NH}$), which is ideal for RDC measurement and structure calculation. In addition, the axis of $C_2$ rotational symmetry of ζ-ζ is parallel to the largest principal axis, $A_{zz}$, of the alignment tensor (FIG. 23b). This result is expected from the rotational averaging of the dimeric complex around its $C_2$ axis in the aligned medium.

The invention claimed is:

1. A method of performing NMR spectroscopy of membrane proteins using nucleic acid nanotubes comprising the steps of:
(a) suspending nucleic acid nanotubes in a solution that comprises a detergent;
(b) forming a liquid crystalline phase comprising the nucleic acid nanotubes;
(c) adding a membrane protein to the solution; and
(d) performing NMR spectroscopy on the protein and nucleic acid nanotube mixture.

2. The method of claim 1, wherein the membrane protein is present at a concentration of at least 0.1 mM.

* * * * *

SEQUENCE LISTING

```
<160> NUMBER OF SEQ ID NOS: 370

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aggatccccg ggtaccggct agtacccgta ta                                32

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atattttagt taatttcatc ttctgaccta aatttaatgg                        40

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttgaaatac cgaccgtgtg ataaataagg cgttaaataa                        40

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggatgtaaat gctgttccat ataacagttt aaatatgcaa ct                     42

<210> SEQ ID NO 5
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttatataact atgaacgcat aaccgataca ccctcagcag cg                            42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaagtacggt gtactttgc gggatcgtta ttcggtcgct ga                             42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgctggaagt ttcaatgcaa atccaatccg gcttaggttg gg                            42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggcttgcagg gacgaccttt ttaacctcgc aagacaaaga ac                            42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagttaaagg ccgcggccag tgccaagcac gacgttgtaa aa                            42

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cttttgataa gaggtcattt ttgcgg                                              26

<210> SEQ ID NO 11
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
ggattagaga gtacctttaa ttgctc                                          26

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgaatttctt aaacagcttg ataccgatag ttgcgccgac                           40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gagcctttaa ttgtatcggt ttatcagctt gctttcgagg                           40

<210> SEQ ID NO 14
<211> LENGTH: 7308
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 14
aatgctacta ctattagtag aattgatgcc acctttcag ctcgcgcccc aaatgaaaat      60
atagctaaac aggttattga ccatttgcga aatgtatcta atggtcaaac taaatctact    120
cgttcgcaga attgggaatc aactgttata tggaatgaaa cttccagaca ccgtacttta    180
gttgcatatt taaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tcttttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600 ggttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttcccctt atgattgacc   1080
```

```
gtctgcgcct cgttccggct aagtaacatg gagcaggtcg cggatttcga cacaatttat    1140
caggcgatga tacaaatctc cgttgtactt tgtttcgcgc ttggtataat cgctgggggt    1200
caaagatgag tgttttagtg tattcttttg cctctttcgt tttaggttgg tgccttcgta    1260
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct taactcccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
ttttggagat tttcaacgtg aaaaaattat tattcgcaat tcctttagtt gttccttttct   1620 attctcactc cgctgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag gtggcggtt     1860 ctgagggtgg cggttctgag gtggcggta ctaaacctcc tgagtacggt gatacaccta     1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcagggggg cattaactgt ttatacgggc actgttactc   2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataagggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccaccct tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttgga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
```

```
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc tttttctagt aattatgatt    3840
ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaatgaataa attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg ctctaatct attagttgtt    4740 agtgctccta aagatatttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttttaatgg cgatgtttta    4980 gggctatcag ttcgcgcatt aaagactaat agccattcaa aaatattgtc tgtgccacgt    5040
attcttacgc tttcaggtca gaagggttct atctctgttg gccagaatgt cccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt cccgtcaag ctctaaatcg    5640 ggggctcct ttagggttcc gatttagtgc tttacggcac ctcgacccca aaaaacttga    5700
tttgggtgat ggttcacgta gtgggccatc gccctgatag acggttttc gccctttgac    5760 gttgagtcc acgttcttta atagtggact cttgttccaa actggaacaa cactcaaccc    5820
tatctcgggc tattcttttg atttataagg gattttgccg atttcggaac caccatcaaa    5880
```

```
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga agcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatccttat acgggtacta gccatgcgta tacggtcgct agcggacttg    6300
cctcgctatc aaaggtctag agtcgacctg caggcatgca agcttggcac tggccgtcgt    6360
tttacaacgt cgtgactggg aaaaccctgg cgttacccaa cttaatcgcc ttgcagcaca    6420 tcccccttttc gccagctggc gtaatagcga agaggcccgc accgatcgcc cttcccaaca    6480
gttgcgcagc ctgaatggcg aatggcgctt tgcctggttt ccggcaccag aagcggtgcc    6540
ggaaagctgg ctggagtgcg atcttcctga ggccgatact gtcgtcgtcc cctcaaactg    6600
gcagatgcac ggttacgatg cgcccatcta caccaacgtg acctatccca ttacggtcaa    6660
tccgccgttt gttcccacgg agaatccgac ggggttgttac tcgctcacat ttaatgttga    6720
tgaaagctgg ctacaggaag gccagacgcg aattatttt gatggcgttc ctattggtta    6780
aaaaatgagc tgatttaaca aaaatttaat gcgaatttta acaaaatatt aacgtttaca    6840
atttaaatat ttgcttatac aatcttcctg tttttggggc ttttctgatt atcaaccggg    6900
gtacatatga ttgacatgct agttttacga ttaccgttca tcgattctct tgtttgctcc    6960
agactctcag gcaatgacct gatagccttt gtagatctct caaaaatagc taccctctcc    7020
ggcattaatt tatcagctag aacgttgaa atcatattg atggtgattt gactgtctcc    7080
ggcctttctc acccttttga atctttacct acacattact caggcattgc atttaaaata    7140
tatgagggtt ctaaaaattt ttatccttgc gttgaaataa aggcttctcc cgcaaaagta    7200
ttacagggtc ataatgtttt tggtacaacc gatttagctt tatgctctga ggctttattg    7260
cttaattttg ctaattcttt gccttgcctg tatgatttat tggatgtt                7308
```

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtaataaaa gggactgttt cctgtgtgcc tttgatagcg ag                          42

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaatggatta tttaaacata cgagccggac ggccagtgcc aa                          42

<210> SEQ ID NO 17
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 17
aacgctcatg gaaataatga gtgagctatg ggtaacgcca gg                              42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatatccaga acaacccgct ttccagtccg ccagctggcg aa                              42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acttgcctga gtagtgaatc ggccaacgaa ctgttgggaa gg                              42

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
attaaccgtt gtagcgccag ggtggtttgc cggaaaccag gc                              42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atcagtgagg ccacctgatt gcccttcagg aagatcgcac tc                              42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agacaggaac ggtagcggtc cacgctggtg catctgccag tt                              42

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 23
atcagagcgg gagcgatggt ggttccgaat gggataggtc ac                              42

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggttgctttg acgagaatag cccgagatcc cgtcggattc tc                              42

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acacccgccg cgctaagagt ccactatttg tagccagctt tc                              42

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agggcgctgg caagcgaaaa accgtctacc aataggaacg cc                              42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtggcgagaa aggatcaccc aaatcaagaa aattcgcatt aa                              42

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggagccccc gattctaaat cggaaccctg tataagcaaa ta                              42

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 29
aagaactggc tcatcggaac aacattatta ccccggttga ta                              42

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
taatttcaac tttatttagg aataccacat cgatgaacgg ta                              42

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gagaaacacc agaaaaagga attacgaggg ctatcaggtc at                              42

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgtaacaaag ctgcctcgtt taccagacat taatgccgga ga                              42

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gagtaatctt gacattttgc aaaagaagca aatcaccatc aa                              42

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cggtgtacag accatttaga ctggatagtg taggtaaaga tt                              42

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
```
taagggaacc gaacattcat tgaatccctt tagaaccctc at                        42

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctccatgtta cttacgagaa tgaccatatt ttgcgggaga ag                        42

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttgtatcatc gcctattata gtcagaagag ctaaatcggt tg                        42

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cccagcgatt atacaggaag cccgaaagca aagaattagc aa                        42

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgaaagaggc aaaattcaaa gcgaaccaaa tagtagtagc at                        42

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gggtaaaata cgtaattaga gagtaccttt catttggggc gc                        42

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttgaggacta aagattttgc ggatggctag atacatttcg ca                        42

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaagacagca tcggtagctc aacatgtttg attcccaatt ct                             42

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttaccagcgc caaattagtt tgaccattta gagcttaatt gc                             42

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aataagttta tttttgttta gctatatttt aattgctcct tt                             42

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ataaaggtgg caacgcatca attctactga ccggaagcaa ac                             42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tccttattac gcagtcatac aggcaaggac ttcaaatatc gc                             42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caataataac ggaagcctca gagcataaca aagcggattg ca                             42

<210> SEQ ID NO 48

```
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cagatagccg aacatgaccc tgtaatacaa tcaaaaatca gg                              42

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agcaatagct atctcaagga taaaaattcc tcaaatgctt ta                              42

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aattgagtta agccatgcct gagtaatgcg tccaatactg cg                              42

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agagggtaat tgagaggccg gagacagttt ttgccagagg gg                              42

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgcattagac gggagttcta gctgataaga cgataaaaac ca                              42

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aatagcagcc tttagagaga tctacaaagc atagtaagag ca                              42

<210> SEQ ID NO 54
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 54
atccaaataa gaaagagcaa acaagagaat tcaactaatg ca                              42

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aatttgccag ttacatgtca atcatatgta caggtagaaa ga                              42

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcctgaatct taccaaaaac aggaagatta aaatctacgt ta                              42

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaatcaagat tagtgttaat attttgtttt ttttggggtc ga                              42

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gttttagcga acctagctca tttttttaatc agggcgatgg cc                             42

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tcagatatag aagggcgtct ggccttccaa agaacgtgga ct                              42

<210> SEQ ID NO 60
<211> LENGTH: 42
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 60
ttttcatcgt aggatgagcg agtaacaaag ggttgagtgt tg                            42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 61
aaccaagtac cgcagcggat tgaccgtaaa tcggcaaaat cc                            42

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 62
ataatcggct gtctgcgcat cgtaaccgtt tgccccagca gg                            42

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 63
ataatatccc atcccagtat cggcctcacc gcctggccct ga                            42

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 64
cgcgcctgtt tatcgcaccg cttctggttt cttttcacca gt                            42

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 65
tccagacgac gacacattca ggctgcgccg cggggagagg cg                            42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

```
<400> SEQUENCE: 66
ataagagaat ataacctctt cgctattagg gaaacctgtc gt                            42

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
acgccaacat gtaacaaggc gattaagtac tcacattaat tg                            42

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cgctcaacag tagggacgtt gtaaaacgaa gcataaagtg ta                            42

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gtatcatatg cgttaggtcg actctagaaa attgttatcc gc                            42

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaataaacac cggagaccgt atacgcatga gctcgaattc gt                            42

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71 aaacttttc aaatcctgaa agcgtaagga gatagaaccc tt                             42

<210> SEQ ID NO 72
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
```
aaatgctgat gcaatggcta ttagtcttcc agtcacacga cc                        42

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 cttttttaacc tccgtcgcca ttaaaaatcg ctcaatcgtc tg                        42

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtcaatagtg aattacagag gtgaggcgat tgcaacagga aa                        42

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cttgaaaaca tagcccacgc tgagagcctc ggccttgctg gt                        42

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cttctgtaaa tcgtccttgc tgaacctctt agtaataaca tc                        42

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggaaacagta catatcagtt ggcaaatctg tccatcacgc aa                        42

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ttaattacat ttaatctaaa atatctttga agtgttttta ta                        42

<210> SEQ ID NO 79
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgagcaaaag aagaccgtca atagataaat taaagggatt tt                    42

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gttacaaaat cgcgtttaca aacaattcct ttcctcgtta ga                    42

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggagaaacaa taacacgtta ttaattttag ggcgcgtact at                    42

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttaacgtcag atgaggaaca aagaaacctg cgcgtaacca cc                    42

<210> SEQ ID NO 83
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcacgtaaaa cagatcctga ttatcagaaa ggagcgggcg ct                    42

<210> SEQ ID NO 84
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tgaataatgg aaggttgttt ggattataga aagccggcga ac                    42

```
<210> SEQ ID NO 85
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agtaacagtg cccggaaagt attaagagcg ttgggaagaa aa                              42

<210> SEQ ID NO 86
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aggagtgtac tggtattagc ggggttttcc ttatgcgatt tt                              42

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tttaccgttc cagtgagagg gttgatatgg cttgagatgg tt                              42

<210> SEQ ID NO 88
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
taaatcctca ttaagtactc aggaggttag gcttgccctg ac                              42

<210> SEQ ID NO 89
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttgaggcagg tcagctcaga accgccacat tacccaaatc aa                              42

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
accagaacca ccacgatagc aagcccaact gaccttcatc aa                              42

<210> SEQ ID NO 91
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctcagaaccg ccacttcgtc accagtacag aggacagatg aa                           42

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
accagagcca ccacacagcc ctcatagtca gacggtcaat ca                           42

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cttattagcg tttgtttcca gacgttagaa atccgcgacc tg                           42

<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agactgtagc gcgttaaaca actttcaaag tacaacggag at                           42

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
accgtaatca gtagaacaac taaaggaaac tcatctttga cc                           42

<210> SEQ ID NO 96
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
agcaaggccg gaaaatctc caaaaaagc accaacctaa aa                             42

<210> SEQ ID NO 97
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 97
ggaattagag ccagcggttt atcagcttag tttccattaa ac                        42

<210> SEQ ID NO 98
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cattaaaggt gaattgatac cgatagttcg gctacagagg ct                        42

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgaatataat gctgaacgag ggtagcaagc gccgacaatg ac                        42

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgataagagg tcatcttttt catgaggagc tttcgaggtg aa                        42

<210> SEQ ID NO 101
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tccaacaggt caggatgcca ctacgaagag gctccaaaag ga                        42

<210> SEQ ID NO 102
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gttttaattc gagcgaatac actaaaactt gcgaataata at                        42

<210> SEQ ID NO 103
<211> LENGTH: 42
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 103
tcaaaaagat taagcaagcg cgaaacaaca gtttcagcgg ag                            42

<210> SEQ ID NO 104
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tctttaccct gactgataaa ttgtgtcgta aatgaatttt ct                            42

<210> SEQ ID NO 105
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aacagttcag aaaagccgga acgaggcgta gcgtaacgat ct                            42

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gaatcgtcat aaattgacca actttgaaaa actacaacgc ct                            42

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtaatagtaa aatgggcgca taggctggta ggaacccatg ta                            42

<210> SEQ ID NO 108
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaatagcgag aggcagaacc ggatattccc tcagagccac ca                            42

<210> SEQ ID NO 109
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 109
acactatcat aacctcattc agtgaatata gtaccgccac cc                         42

<210> SEQ ID NO 110
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gatacataac gccacgagta gtaaattgaa gtatagcccg ga                         42

<210> SEQ ID NO 111
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ttcatcagtt gagaatcatt gtgaattagc tcagtaccag gc                         42

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ataaaacgaa ctaatatacc agtcaggagc tgagactcct ca                         42

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggtgccgtaa agcatagagc ttgacgggct tttcggaacc ta                         42

<210> SEQ ID NO 114
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cactacgtga accaagggaa gaaagcgatg atggcaattc at                         42

<210> SEQ ID NO 115
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
```

```
ccaacgtcaa agggtgtagc ggtcacgcac cagaaggagc gg            42
```

<210> SEQ ID NO 116
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
ttccagtttg aactaatgc gccgctacaa aagtttgagt aa             42
```

<210> SEQ ID NO 117
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
cttataaatc aaaagcacgt ataacgtgga caactcgtat ta            42
```

<210> SEQ ID NO 118
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
cgaaaatcct gttttaaaca ggaggccgta catttgagga tt            42
```

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
gagagttgca gcaacgccag aatcctgaag gagcactaac aa            42
```

<210> SEQ ID NO 120
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
gagacgggca acagcgagta aaagagtcaa cagttgaaag ga            42
```

<210> SEQ ID NO 121
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

```
gtttgcgtat tgggcaatac ttctttgaaa atatcaaacc ct            42
```

```
<210> SEQ ID NO 122
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gccagctgca ttaaaagaac tcaaactaag cagcaaatga aa                          42

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgttgcgctc actgtattac cgccagccgt cagtattaac ac                          42

<210> SEQ ID NO 124
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aagcctgggg tgcctaccta cattttgaac cgaacgaacc ac                          42

<210> SEQ ID NO 125
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tcacaattcc acaccattgg cagattcata atgcgcgaac tg                          42

<210> SEQ ID NO 126
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aatcatggtc atagcattct ggccaacaaa tacgtggcac ag                          42

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gcaagtccgc tagcatcata attactagca aagaacgcga ga                          42

<210> SEQ ID NO 128
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcttgcatgc ctgcatacaa attcttacat ataactatat gt                              42

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gttttcccag tcacgcttaa ttgagaatgt ctgagagact ac                              42

<210> SEQ ID NO 130
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130 aggggatgt gctgtttagg cagaggcaag acgctgagaa ga                               42

<210> SEQ ID NO 131
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcgatcggtg cgggagtacc gacaaaagtt tcccttagaa tc                              42

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aaagcgccat tcgcataaac aacatgttag tgaataacct tg                              42

<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cagccagctt tccgaacaat agataagttt accttttta at                               42

<210> SEQ ID NO 134
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 134
tgaggggacg acgataattt acgagcattc aagaaaacaa aa                          42

<210> SEQ ID NO 135
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gttggtgtag atggttcctt atcattcctc atttcaatta cc                          42

<210> SEQ ID NO 136
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cgtgggaaca aacgctcatc gagaacaagc tttgaatacc aa                          42

<210> SEQ ID NO 137
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
atcaacatta aatgatcatt accgcgccta cctttacat cg                           42

<210> SEQ ID NO 138
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
atcaaaaata attccttatc cggtattcgt agattttcag gt                          42

<210> SEQ ID NO 139
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atttttgtta aatccccgac ttgcgggata tcaaaattat tt                          42

<210> SEQ ID NO 140
<211> LENGTH: 42
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 140
tttaaattgt aaactgctat tttgcaccgc cccctgccta tc                          42

<210> SEQ ID NO 141
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atcagaaaag ccccaacgct aacgagcggg gtcagtgcct tg                          42

<210> SEQ ID NO 142
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
atcgtaaaac tagcaaaata aacagccagc ttttgatgat ac                          42

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tgcctgagag tctgcgattt tttgtttagc gcagtctctg aa                          42

<210> SEQ ID NO 144
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gggtagctat ttttcagaga gaataacata ttcacaaaca aa                          42

<210> SEQ ID NO 145
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tatgatattc aaccgaatta actgaacagc attgacagga gg                          42

<210> SEQ ID NO 146
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
caaaagggtg agaacgctaa tatcagagcc ctcagagccg cc					42

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
atattttaaa tgcacaataa taagagcatc agagccgcca cc					42

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
cctttatttc aacgtaccga agccctttc aaaatcaccg ga					42

<210> SEQ ID NO 149
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
taccaaaaac attaaagtta ccagaaggtc ggtcatagcc cc					42

<210> SEQ ID NO 150
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
aattaagcaa taaataccca aaagaacttt gcctttagcg tc					42

<210> SEQ ID NO 151
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
taacatccaa taaatatgtt agcaaacgcc atcgatagca gc					42

<210> SEQ ID NO 152
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gagctgaaaa ggtgatataa agaaacggc accattacca tt                         42

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
aatggtcaat aaccgtcaca atcaatagac ttgagccatt tg                         42

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcgaacgagt agatgacaaa agggcgactg acggaaatta tt                         42

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aacaaccatc gcccgggaag gtaaatatat tcaaccgatt ga                         42

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tttcttaaac agcttatcac cgtcaccgaa aattcatatg gt                         42

<210> SEQ ID NO 157
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gcctttaatt gtatcaaaat caccagtaca aagacaccac gg                         42

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tttttcacgt tgaacgtcac caatgaaata gaaaatacat ac                         42

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgagaataga aaggcgacag aatcaagtgg catgattaag ac                     42

<210> SEQ ID NO 160
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gtatgggatt ttgctttcat cggcatttaa accgaggaaa cg                     42

<210> SEQ ID NO 161
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aaagttttgt cgtcccatct tttcataatt aagaaaagta ag                     42

<210> SEQ ID NO 162
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gtagcattcc acagcggaac cgcctcccag aaacaatgaa at                     42

<210> SEQ ID NO 163
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccgtaacact gagtcctcag agccaccaag ataacccaca ag                     42

<210> SEQ ID NO 164
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ccctcatttt caggcagagc cgccgccacc ctgaacaaag tc                     42

```
<210> SEQ ID NO 165
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tcagaaccgc caccacgatt ggccttgata aaacaggga ag                              42

<210> SEQ ID NO 166
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ataggtgtat caccagccag aatggaaaac gtcaaaatg aa                              42

<210> SEQ ID NO 167
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggataagtgc cgtcaagcgt catacatgta ttatttatcc ca                             42

<210> SEQ ID NO 168
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
agagaaggat taggaataag ttttaacgtc tttccagagc ct                             42

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ttattctgaa acattataaa cagttaatca gctacaattt ta                             42

<210> SEQ ID NO 170
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
caatataatc ctgagttaga acctaccagg ttttgaagcc tt                             42

<210> SEQ ID NO 171
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aattatcatc atataataaa gaaattgcta agaacgcgag gc                           42

<210> SEQ ID NO 172
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cattatcatt ttgcatatac agtaacagca atagcaagca aa                           42

<210> SEQ ID NO 173
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aatcctttgc ccgaggattc gcctgattgc aagccgtttt ta                           42

<210> SEQ ID NO 174
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tagaagtatt agaccagagg cgaattataa gaacgggtat ta                           42

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ctaatagatt agagtgatga acaaacagt agaaaccaat ca                            42

<210> SEQ ID NO 176
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
attgaggaag gttacaattt catttgaacc tgaacaagaa aa                           42

<210> SEQ ID NO 177
<211> LENGTH: 42
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 177
caatcaatat ctggaatcaa tatatgtgca gctaatgcag aa                          42

<210> SEQ ID NO 178
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aatctaaagc atcacgctat taattaatgt aaagtaattc tg                          42

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cgcctgcaac agtggatagc ttagattatt ttcgagccag ta                          42

<210> SEQ ID NO 180
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagcagaaga taaatatcaa aatcatagcg ccatatttaa ca                          42

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atagccctaa aacagcttag gttgggttca gtataaagcc aa                          42

<210> SEQ ID NO 182
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
acaatatttt tgaaatccaa tcgcaagaaa aaagcctgtt ta                          42

<210> SEQ ID NO 183
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
ctgttaaagg ccgcgatccc cgggtaccgg ctagtacccg ta                              42

<210> SEQ ID NO 184
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ggtttgaaat accgttccat ataacagttt aaatatgcaa ct                              42

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
taaatttaat gggaacgcat aaccgataca ccctcagcag cg                              42

<210> SEQ ID NO 186
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aaagtacggt gtagttttgc gggatcgtta ttcggtcgct ga                              42

<210> SEQ ID NO 187
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tactggaagt ttcaaccgtg tgataaattt catcttctga cc                              42

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ggcttgcagg gagaatattt tagttaataa ggcgttaaat aa                              42

<210> SEQ ID NO 189
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 189
aggatccccg ggtaccggct agtacccgta ta                          32

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
atattttagt taatttcatc ttctgaccta aatttaatgg                  40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tttgaaatac cgaccgtgtg ataaataagg cgttaaataa                  40

<210> SEQ ID NO 192
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ctggaagttt cattccatat aacagt                                 26

<210> SEQ ID NO 193
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ttaaatatgc aactaaagta cggtgt                                 26

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gttaaaggcc gcttttgcgg gatcgtcacc ctcagcagcg                  40

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
```
acgcataacc gatatattcg gtcgctgagg cttgcaggga 40

<210> SEQ ID NO 196
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tatacgggta ctagccatgc gtatacggtc gctagcggac ttgcctcgct atcaaaggt 59

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tcgagctcgg tacccgggga tccttatacg 30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cgcatggcta gtacccgtat aaggatcccc 30

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggtactagcc atgcgtatac ggtcgctagc 30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tagcgaggca agtccgctag cgaccgtata 30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ggacttgcct cgctatcaaa ggtctagagt 30

```
<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
catgcctgca ggtcgactct agacctttga                                          30

<210> SEQ ID NO 203
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ccattgcaac aggatttgat agcgaggctg caaggcgatt aa                             42

<210> SEQ ID NO 204
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tatcggcctt gctgctagta cccgtatagg cctcttcgct at                             42

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gattagtaat aacagtaatc atggtcatgc cattcaggct gc                             42

<210> SEQ ID NO 206
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tctgtccatc acgcgctcac aattccaccg gcaccgcttc tg                             42

<210> SEQ ID NO 207
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gagaagtgtt tttataaagc ctggggtgga cagtatcggc ct                             42

<210> SEQ ID NO 208
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cgattaaagg gatttgcgtt gcgctcacgg gcgcatcgta ac                              42

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgctttcctc gttagtgcca gctgcattcg gcggattgac cg                              42

<210> SEQ ID NO 210
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
acagggcgcg tactcggttt gcgtattgtg tgagcgagta ac                              42

<210> SEQ ID NO 211
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gctgcgcgta accagtgaga cgggcaactc gcgtctggcc tt                              42

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gaaaggagcg ggcggagaga gttgcagctc agctcatttt tt                              42

<210> SEQ ID NO 213
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gggaaagccg gcgaggcgaa aatcctgtac gttaatattt tg                              42

<210> SEQ ID NO 214
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 214
aaatcggaac cctacccttta taaatcaacc aaaaacagga ag                         42

<210> SEQ ID NO 215
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
acccaaatca gtttgttcc agtttggagc atgtcaatca ta                          42

<210> SEQ ID NO 216
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
aaaaaccgtc tatcctccaa cgtcaaagtg gagcaaacaa ga                         42

<210> SEQ ID NO 217
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
taaggcttgc cctgacttta atcattgttt gagagatcta ca                         42

<210> SEQ ID NO 218
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tcattaccca aatcgctcat tataccagcc gttctagctg at                         42

<210> SEQ ID NO 219
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219 ggctgaccttt catctaataa aacgaactaa aggccggaga ca                        42

<210> SEQ ID NO 220
<211> LENGTH: 42
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 220
aaagaggaca gatggattca tcagttgaca atgcctgagt aa                              42

<210> SEQ ID NO 221
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cgcagacggt caatcagata cataacgccg caaggataaa aa                              42

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cgaaatccgc gacccaacac tatcataata tgaccctgta at                              42

<210> SEQ ID NO 223
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaagtacaac ggagcaaaat agcgagagaa gcctcagagc at                              42

<210> SEQ ID NO 224
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
acactcatct ttgagggtaa tagtaaaaaa tcatacaggc aa                              42

<210> SEQ ID NO 225
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aggcaccaac ctaacggaat cgtcataatg gcatcaattc ta                              42

<210> SEQ ID NO 226
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 226
gaagtttcca ttaataaaca gttcagaacc tgtttagcta ta                              42

<210> SEQ ID NO 227
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
aacggctaca gagggtctt taccctgaat ttagtttgac ca                               42

<210> SEQ ID NO 228
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtcaccctca gcagcatcaa aaagattaca ttccatataa ca                              42

<210> SEQ ID NO 229
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cgctgaggct tgcagcgttt taattcgaca tgttttaaat at                              42

<210> SEQ ID NO 230
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
aatgacaaca accaactcca acaggtcaat ggcttagagc tt                              42

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cgtagaaaat acatatgctg tagctcaagc ttcaaagcga ac                              42

<210> SEQ ID NO 232
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
```
ctggcatgat taaggtgtct ggaagtttag aggaagcccg aa    42

<210> SEQ ID NO 233
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggaaaccgag gaaactgcga acgagtagct attatagtca ga    42

<210> SEQ ID NO 234
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttttaagaaa agtacaaatg gtcaataaaa cgagaatgac ca    42

<210> SEQ ID NO 235
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
caagaaacaa tgaagcgagc tgaaaaggat attcattgaa tc    42

<210> SEQ ID NO 236
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
agagataacc cacaattaac atccaatatg tttagactgg at    42

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
caccctgaac aaagaaaatt aagcaatagc ttttgcaaaa ga    42

<210> SEQ ID NO 238
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cataaaaaca gggatgtacc aaaaacatcc ctcgtttacc ag    42

<210> SEQ ID NO 239
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
taacgtcaaa aatgagcctt tatttcaaca aaaggaatta cg                              42

<210> SEQ ID NO 240
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
catattattt atccatatat tttaaatgga tttaggaata cc                              42

<210> SEQ ID NO 241
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cgtctttcca gagcttcaaa agggtgagaa cggaacaaca tt                              42

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
cccagctaca atttaatatg atattcaatc aggacgttgg ga                              42

<210> SEQ ID NO 243
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gaggttttga agccgagggt agctatttga attaccttat gc                              42

<210> SEQ ID NO 244
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tctaagaacg cgagattgcc tgagagtcgg attgggcttg ag                              42

-continued

<210> SEQ ID NO 245
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cccaatagca agcataatcg taaaactaac aagagtccac ta                42

<210> SEQ ID NO 246
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aagcaagccg tttttaatca gaaaagccaa gaatagcccg ag                42

<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ccaagaacgg gtattattta aattgtaatt gatggtggtt cc                42

<210> SEQ ID NO 248
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
atgtagaaac caataaattt ttgttaaaaa gcggtccacg ct                42

<210> SEQ ID NO 249
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gtcctgaaca agaaccatca aaaataatag ctgattgccc tt                42

<210> SEQ ID NO 250
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ttcagctaat gcagtcatca acattaaagg cgccagggtg gt                42

<210> SEQ ID NO 251
<211> LENGTH: 42

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aggtaaagta attctccgtg ggaacaaaaa tgaatcggcc aa                         42

<210> SEQ ID NO 252
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cattttcgag ccagacgttg gtgtagattg cccgctttcc ag                         42

<210> SEQ ID NO 253
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
atcgccatat ttaatttgag gggacgaccc taatgagtga gc                         42

<210> SEQ ID NO 254
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
accagtataa agcctccagc cagctttcac aacatacgag cc                         42

<210> SEQ ID NO 255
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
agaaaaagcc tgttgcaaag cgccattcag ctgtttcctg tg                         42

<210> SEQ ID NO 256
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ataaggcgtt aaatgggcga tcggtgcgag gatccccggg ta                         42

<210> SEQ ID NO 257
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 257
ctgacctaaa tttaaaaggg ggatgtgcaa gtccgctagc ga                              42

<210> SEQ ID NO 258
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gcgagaaaac ttttgggttt tcccagtctt gcatgcctgc ag                              42

<210> SEQ ID NO 259
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aggtctgaga gactctcaat cgtctgaaaa tacctacatt tt                              42

<210> SEQ ID NO 260
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
taagacgctg agaaagtcac acgaccagaa tattaccgcc ag                              42

<210> SEQ ID NO 261
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
attttcccct agaagataga acccttctag aagaactcaa ac                              42

<210> SEQ ID NO 262
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tgagtgaata acctagacaa tatttttgag caatacttct tt                              42

<210> SEQ ID NO 263
<211> LENGTH: 42
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 263
aattaccttt tttatgatag ccctaaaaac cgagtaaaag ag                              42

<210> SEQ ID NO 264
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
catcaagaaa acaaaccagc agaagatata cgccagaatc ct                              42

<210> SEQ ID NO 265
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
attcatttca attaaccgcc tgcaacaggc taaacaggag gc                              42

<210> SEQ ID NO 266
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ttgctttgaa taccaaaatc taaagcatga gcacgtataa cg                              42

<210> SEQ ID NO 267
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267 agtaccttt acatctcaat caatatctct taatgcgccg ct                              42

<210> SEQ ID NO 268
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gcgtagattt tcaggaattg aggaaggtag tgtagcggtc ac                              42

<210> SEQ ID NO 269
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
catatcaaaa ttataactaa tagattagga agggaagaaa gc                              42

<210> SEQ ID NO 270
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gtttggatta tacttttaga agtattagtt tagagcttga cg                              42

<210> SEQ ID NO 271
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ctgattatca gatgtaaatc ctttgccctg ccgtaaagca ct                              42

<210> SEQ ID NO 272
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
aacaaagaaa ccacaacatt atcattttct acgtgaacca tc                              42

<210> SEQ ID NO 273
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aagcgcagtc tctgactggt aataagttaa cgagtagtaa cg                              42

<210> SEQ ID NO 274
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gatattcaca aacatgcccg tataaacagc tcattcagtg aa                              42

<210> SEQ ID NO 275
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
cagcattgac aggatattat tctgaaacca agaaccggat at                              42

<210> SEQ ID NO 276
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
caccctcaga gccgcaagag aaggattaca ggcgcatagg ct                              42

<210> SEQ ID NO 277
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cctcagagcc gccagcggat aagtgccgac tgaccaactt tg                              42

<210> SEQ ID NO 278
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
aatcaaaatc accggaatag gtgtatcata gccggaacga gg                              42

<210> SEQ ID NO 279
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tttcggtcat agcccctcag aaccgccact gataaattgt gt                              42

<210> SEQ ID NO 280
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtttgccttt agcgcaccct cattttcaac caagcgcgaa ac                              42

<210> SEQ ID NO 281
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
aaccatcgat agcataccgt aacactgaaa gaatacacta aa                              42

<210> SEQ ID NO 282
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 282
tagcaccatt accactgtag cattccacta atgccactac ga                               42

<210> SEQ ID NO 283
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 283
cgacttgagc cattctaaag ttttgtcgga cttttcatg ag                                42

<210> SEQ ID NO 284
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
attgacggaa attactgtat gggattttgg aacgagggta gc                               42

<210> SEQ ID NO 285
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
caaaagggcg acatagtgag aatagaaagc ttttgcggga tc                               42

<210> SEQ ID NO 286
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 286
cacaatcaat agaaattttt tcacgttgcc gatatattcg gt                               42

<210> SEQ ID NO 287
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 287
cagaccggaa gcaatcgccc acgcataaaa aatctccaaa aa                               42

<210> SEQ ID NO 288

-continued

<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
agacttcaaa tatcgggagt taaaggccgg aacaactaaa gg                42

<210> SEQ ID NO 289
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
agcaaagcgg attgcgaaag acagcatcgc taaacaactt tc                42

<210> SEQ ID NO 290
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
taaatcaaaa atcactttga ggactaaatc tttccagacg tt                42

<210> SEQ ID NO 291
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
cccctcaaat gcttacgggt aaaatacgag acagccctca ta                42

<210> SEQ ID NO 292
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
agcgtccaat actgaacgaa agaggcaagt ttcgtcacca gt                42

<210> SEQ ID NO 293
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
agttttgcca gaggccccca gcgattatgg gatagcaagc cc                42

<210> SEQ ID NO 294
<211> LENGTH: 42
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 294
acgacgataa aaacatttgt atcatcgccc ctcagaaccg cc                           42

<210> SEQ ID NO 295
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
aggcatagta agagtgctcc atgttactcc gtactcagga gg                           42

<210> SEQ ID NO 296
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
acattcaact aatgcataag ggaaccgatc gagagggttg at                           42

<210> SEQ ID NO 297
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
attacaggta gaaaaacggt gtacagacgg attagcgggg tt                           42

<210> SEQ ID NO 298
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
agaaaaatct acgtaagagt aatcttgaat gaaagtatta ag                           42

<210> SEQ ID NO 299
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gattttaaga actgaacgta acaaagctgt taatgccccc tg                           42

<210> SEQ ID NO 300
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 300
atggtttaat ttcaacgaga aacaccagtt aacggggtca gt                              42

<210> SEQ ID NO 301
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ttaaagaacg tggaagggcg atggcccagc catggctttt ga                              42

<210> SEQ ID NO 302
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
atagggttga gtgtttttgg ggtcgaggga acgttattaa tt                              42

<210> SEQ ID NO 303
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gaaatcggca aaataaggga gcccccgaac tttacaaaca at                              42

<210> SEQ ID NO 304
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ggtttgcccc agcaacgtgg cgagaaagag ccgtcaatag at                              42

<210> SEQ ID NO 305
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
caccgcctgg ccctctaggg cgctggcata tctaaaatat ct                              42

<210> SEQ ID NO 306
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 306 ttttctttc accaccacac ccgccgcggg tcagttggca aa                                42

<210> SEQ ID NO 307
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cgcgcgggga gaggatggtt gctttgacca ccttgctgaa cc                               42

<210> SEQ ID NO 308
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tcgggaaacc tgtcgaatca gagcgggatg ccacgctgag ag                               42

<210> SEQ ID NO 309
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
taactcacat taatttagac aggaacggaa acagaggtga gg                               42

<210> SEQ ID NO 310
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ggaagcataa agtgtaatca gtgaggccca tcgccattaa aa                               42

<210> SEQ ID NO 311
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tgaaattgtt atccaaatta accgttgtaa tggctattag tc                               42

<210> SEQ ID NO 312
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ccgagctcga attctcactt gcctgagtga cctgaaagcg ta                        42

<210> SEQ ID NO 313
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ccgtatacgc atgggtaata tccagaacta ataaaaggga ca                        42

<210> SEQ ID NO 314
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gtcgactcta gaccaaaacg ctcatggaat ggattattta ca                        42

<210> SEQ ID NO 315
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gttgggtaac gccatcaaat atattttatt tatcaaaatc at                        42

<210> SEQ ID NO 316
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tacgccagct ggcgatggtt tgaaatacgc gatagcttag at                        42

<210> SEQ ID NO 317
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gcaactgttg ggaaaagaat aaacaccggt cgctattaat ta                        42

<210> SEQ ID NO 318
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gtgccggaaa ccagtagtat catatgcgta aatcaatata tg                        42

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
caggaagatc gcacaacgct caacagtaaa caatttcatt tg                           42

<210> SEQ ID NO 320
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cgtgcatctg ccagcaacgc caacatgtga tgatgaaaca aa                           42

<210> SEQ ID NO 321
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
taatgggata ggtctaataa gagaatatcg cagaggcgaa tt                           42

<210> SEQ ID NO 322
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
aacccgtcgg attctgtcca gacgacgaac ggattcgcct ga                           42

<210> SEQ ID NO 323
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
cctgtagcca gcttaacgcg cctgtttaga atatacagta ac                           42

<210> SEQ ID NO 324
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
aaccaatagg aacgaaataa tatcccatga aataagaaa tt                            42

```
<210> SEQ ID NO 325
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ttaaaattcg cattcaataa tcggctgtgg gttagaacct ac                              42

<210> SEQ ID NO 326
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
attgtataag caaataaacc aagtaccgat ataatcctga tt                              42

<210> SEQ ID NO 327
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
tgtaccccgg ttgatatttt catcgtagtt atcatcatat tc                              42

<210> SEQ ID NO 328
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gaatcgatga acggaatcag atatagaagt aagcgtcata gg                              42

<210> SEQ ID NO 329
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
aaggctatca ggtcgcgttt tagcgaacaa agccagaatg ga                              42

<210> SEQ ID NO 330
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
aaattaatgc cggattaaat caagattaag acgattggcc tt                              42

<210> SEQ ID NO 331
<211> LENGTH: 42
```

```
<210> SEQ ID NO 331
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gtcaaatcac catctatcct gaatcttaac cagagccgcc gc                    42

<210> SEQ ID NO 332
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tgtgtaggta aagactaatt tgccagttac cctcagagcc ac                    42

<210> SEQ ID NO 333
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tttttagaac cctccaatcc aaataagaac cggaaccgcc tc                    42

<210> SEQ ID NO 334
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
acttttgcgg gagaaaaata gcagcctttg ccatcttttc at                    42

<210> SEQ ID NO 335
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
aaagctaaat cggtagcgca ttagacgggt tttcatcggc at                    42

<210> SEQ ID NO 336
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ggcaaagaat tagctcagag ggtaattgag cgacagaatc aa                    42

<210> SEQ ID NO 337
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 337
ctaatagtag tagcagaatt gagttaagaa cgtcaccaat ga                              42

<210> SEQ ID NO 338
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
ttttcatttg gggcatagca atagctatag caaaatcacc ag                              42

<210> SEQ ID NO 339
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
ttagatacat ttcgagcaga tagccgaaat tatcaccgtc ac                              42

<210> SEQ ID NO 340
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gttgattccc aattcgcaat aataacggga gggaaggtaa at                              42

<210> SEQ ID NO 341
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gcaactaaag tacgactcct tattacgcac cagcgccaaa ga                              42

<210> SEQ ID NO 342
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
aattgctgaa tataacataa aggtggcata agtttatttt gt                              42

<210> SEQ ID NO 343
<211> LENGTH: 42
<212> TYPE: DNA
<213> ORGANISM: Artificial Sequence
<220> FEATURE:
<223> OTHER INFORMATION: Description of Artificial Sequence: Synthetic
```

-continued

<400> SEQUENCE: 343
aaaggctcca aagaagaca ccacggaaac atataaaga aa                42

<210> SEQ ID NO 344
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
aattgcgaat aataaattca tatggtttag tatgttagca aa                42

<210> SEQ ID NO 345
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
aacagtttca gcggtcaacc gattgaggaa tacccaaaag aa                42

<210> SEQ ID NO 346
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
agtaaatgaa tttttcatt aaaggtgaca aagttaccag aa                42

<210> SEQ ID NO 347
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gttagcgtaa cgattgggaa ttagagccct taccgaagcc ct                42

<210> SEQ ID NO 348
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
acaaactaca acgcttagca aggccggacc caataataag ag                42

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 349
aataggaacc catggcaccg taatcagtag cgctaatatc ag                              42

<210> SEQ ID NO 350
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
accctcagag ccactcagac tgtagcgcga gaattaactg aa                              42

<210> SEQ ID NO 351
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tttagtaccg ccacccctta ttagcgttta cagagagaat aa                              42

<210> SEQ ID NO 352
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ataagtatag cccggaacca gagccaccaa cgattttttg tt                              42

<210> SEQ ID NO 353
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ttgctcagta ccagccctca gaaccgccac aaaataaaca gc                              42

<210> SEQ ID NO 354
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aggctgagac tcctccacca gaaccacccc aacgctaacg ag                              42

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
```

```
cctatttcgg aaccggttga ggcaggtcgt tgctattttg ca                          42
```

<210> SEQ ID NO 356
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356

```
gccttgagta acagaataaa tcctcattct cccgacttgc gg                          42
```

<210> SEQ ID NO 357
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357

```
tgatacagga gtgtaattta ccgttccagg cttatccggt at                          42
```

<210> SEQ ID NO 358
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358

```
ttaaaagttt gagtcagaag gagcggaaga atcattaccg cg                          42
```

<210> SEQ ID NO 359
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359

```
tcgacaactc gtatatggca attcatcaca ctcatcgaga ac                          42
```

<210> SEQ ID NO 360
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360

```
aatacatttg aggatctgaa taatggaact ttccttatca tt                          42
```

<210> SEQ ID NO 361
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361

```
ttaggagcac taacttgcac gtaaaacacc taatttacga gc                          42
```

<210> SEQ ID NO 362
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tcaacagttg aaaggtttaa cgtcagattc aacaatagat aa                              42

<210> SEQ ID NO 363
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
tcaaatatca aacccgggag aaacaataca ataaacaaca tg                              42

<210> SEQ ID NO 364
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ccagcagcaa atgaaagtta caaaatcgaa agtaccgaca aa                              42

<210> SEQ ID NO 365
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
cggtcagtat taaccctgag caaaagaaaa tttaggcaga gg                              42

<210> SEQ ID NO 366
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
ataccgaacg aaccaattaa ttacatttgg gcttaattga ga                              42

<210> SEQ ID NO 367
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tttaatgcgc gaacatggaa acagtacatt atacaaattc tt                              42

<210> SEQ ID NO 368

```
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
agaatacgtg gcactgcttc tgtaaatcga atcataatta ct                             42

<210> SEQ ID NO 369
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ttctggccaa cagatccttg aaaacatacg accgtgtgat aa                             42

<210> SEQ ID NO 370
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ttggcagatt caccgagtca atagtgaagt taatttcatc tt                             42
```